(12) United States Patent
Erickson et al.

(10) Patent No.: US 9,296,711 B2
(45) Date of Patent: Mar. 29, 2016

(54) SUBSTITUTED ISOXAZOLE AMIDE COMPOUNDS AS INHIBITORS OF STEAROYL-COA DESATURASE 1 (SCD1)

(71) Applicant: Hoffman-La Roche Inc., Nutley, NJ (US)

(72) Inventors: Shawn David Erickson, Leonia, NJ (US); Paul Gillespie, Westfield, NY (US); Eric Mertz, Fair Lawn, NJ (US)

(73) Assignee: HOFFMAN-LA ROCHE INC., Nutley, NJ (US)

( * ) Notice: Subject to any disclaimer, the term of this patent is extended or adjusted under 35 U.S.C. 154(b) by 0 days.

(21) Appl. No.: 14/443,823

(22) PCT Filed: Dec. 2, 2013

(86) PCT No.: PCT/EP2013/075219
§ 371 (c)(1),
(2) Date: May 19, 2015

(87) PCT Pub. No.: WO2014/086704
PCT Pub. Date: Jun. 12, 2014

(65) Prior Publication Data
US 2015/0307463 A1    Oct. 29, 2015

Related U.S. Application Data

(60) Provisional application No. 61/732,466, filed on Dec. 3, 2012.

(51) Int. Cl.
*C07D 261/18* (2006.01)
*C07D 413/12* (2006.01)
*C07D 413/10* (2006.01)
*C07D 413/04* (2006.01)

(52) U.S. Cl.
CPC ............ *C07D 261/18* (2013.01); *C07D 413/04* (2013.01); *C07D 413/10* (2013.01); *C07D 413/12* (2013.01)

(58) Field of Classification Search
None
See application file for complete search history.

(56) References Cited

U.S. PATENT DOCUMENTS

2010/0249192 A1* 9/2010 Li .................. C07D 401/04
514/340

* cited by examiner

Primary Examiner — Timothy R Rozof

(57) ABSTRACT

The invention is concerned with a compound of formula (I) and pharmaceutically acceptable salts thereof. In addition, the present invention relates to methods of manufacturing and using the compound of formula (I) as well as pharmaceutical compositions containing such compounds. The compound of formula (I) are SCD1 inhibitors and may be useful in treating cancer.

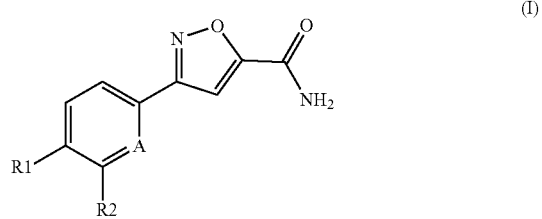

13 Claims, No Drawings

SUBSTITUTED ISOXAZOLE AMIDE COMPOUNDS AS INHIBITORS OF STEAROYL-COA DESATURASE 1 (SCD1)

This application is a National Stage Application of PCT/EP2013/075219 filed Dec. 2, 2013, which claims priority from U.S. Provisional Patent Application No. 61/732,466, filed on Dec. 3, 2012. The priority of both said PCT and U.S. Provisional Patent Application are claimed. Each of the prior mentioned applications is hereby incorporated by reference herein in its entirety.

The present invention relates to organic compounds useful as inhibitors of Stearoyl-CoA desaturase 1 (SCD1) for the treatment of diseases such as, for example, cancer. In particular, the invention relates to substituted isoxazole amide compounds, their manufacture, pharmaceutical compositions containing them and methods of use.

The invention relates in particular to a compound of formula (I)

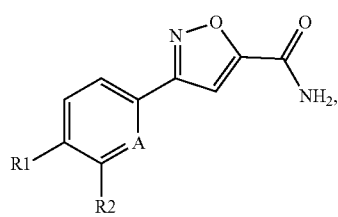

wherein:

A is —CH— or nitrogen;
R1 is —O—CH$_2$—R3, —CH$_2$—O—R3 or —CH$_2$—R4;
R2 is hydrogen or halogen;
R3 is -phenyl, optionally mono- or bi-substituted independently with lower alkyl, alkoxy, halogen, —CN, —CF$_3$, —OCF$_3$, —SCF$_3$, —S(=O)CF$_3$ or —SO$_2$CH$_3$, or
-pyridinyl, optionally substituted with lower alkyl or halogen; and
R4 is indolyl, dihydroindolyl, isoindolyl, dihydroisoindolyl, benzotriazolyl, benzoimidazolyl, indazolyl, tetrahydroquinolinyl, methyldihydroindolyl or methylindolyl;

or a pharmaceutically acceptable salt thereof.

Cancer is a broad range of diseases, all of which are defined by unregulated growth and spread of abnormal cells. In cancer, cells divide and grow uncontrollably, forming malignant tumors, and invade nearby parts of the body. In the United States alone in 2012, approximately 600,000 deaths will result from cancer. [American Cancer Society. *Cancer Facts & Figures*. 2012. Atlanta: American Cancer Society; 2012.]

The fate of the cell is the function of highly regulated activation and deactivation of both biosynthetic and energy-generating metabolic pathways. In mammals, cell growth, proliferation and survival require the formation of new cell membranes, which, in turn, entails the production of the appropriate lipids for a fully functional cell membrane. Saturated fatty acids (SFAs) and monounsaturated fatty acids (MUFAs) are the major fatty acid species in mammalian cellular lipids. As building blocks of phospholipids, diacylglycerols, triacylglycerols and cholesteryl esters, SFAs and MUFAs are fundamental building blocks of membrane structures and are critical mediators/regulators of myriad cellular activities. Because changes in the balance of SFA and MUFA in lipids can influence this wide array of cellular functions, the composition and distribution of SFA and MUFA within cells must be tightly regulated. Cellular lipids, including mono-unsaturated fatty acids and saturated fatty acids, have been linked to tumor cell proliferation and tumor cell survival due to their dual roles as 1) sources of metabolic energy and 2) mediators of cell signaling pathways. One key regulator of the fatty acid composition of cellular lipids is stearoyl-CoA desaturase 1 (SCD1) which catalyzes the introduction of the first double bond in the cis-delta-9 position of several saturated fatty acyl-CoAs, principally palmitoyl-CoA and stearoyl-CoA, to yield palmitoleoyl- and oleoyl-CoA, respectively. [R. A. Igal *Carcinogenesis* 2010, 31, 1509-1515].

The human SCD1 gene is ubiquitously expressed, with highest levels in brain, liver, heart and lung. SCD1 is highly expressed in oncogene-transformed lung fibroblasts and in cancer cells. SCD1 has been identified as an enzyme in the fatty acid synthesis pathway that is essential for cancer cell viability [Mason P, Liang B, Li L, Fremgen T, Murphy E, et al. PLoS ONE 2012, 7(3): e33823]. As an important regulator of the composition of cellular lipids, SCD1 has been proposed as a target for cancer therapies.

It has been demonstrated that SCD1 mRNA levels are elevated in tumors and that inhibition of SCD1 with siRNA or a small molecule inhibitor results in strong induction of apoptosis and growth inhibition. [U. V. Roongta et al. *Molecular Cancer Research* 2011, 9, 1551-1561]. It would be useful, therefore, to provide small molecule inhibitors of SCD1 for the treatment of cancer.

The invention also provides for pharmaceutical compositions comprising the compounds of the invention, methods of using the compounds of the invention and methods of preparing the compounds of the invention.

Unless otherwise indicated, the following specific terms and phrases used in the description and claims are defined as follows:

The term "moiety" refers to an atom or group of chemically bonded atoms that is attached to another atom or molecule by one or more chemical bonds thereby forming part of a molecule. For example, the R variables of formula (I) refer to moieties that are attached to the core structure of formula (I) by a covalent bond.

In reference to a particular moiety with one or more hydrogen atoms, the term "substituted" refers to the fact that at least one of the hydrogen atoms of that moiety is replaced by another substituent or moiety. For example, the term "lower alkyl substituted by halogen" means that one or more hydrogen atoms of a lower alkyl (as defined below) is replaced by one or more halogen atoms (e.g., trifluoromethyl, difluoromethyl, fluoromethyl, chloromethyl, etc.).

The term "alkyl" refers to an aliphatic straight-chain or branched-chain saturated hydrocarbon moiety having 1 to 20 carbon atoms. In particular embodiments the alkyl has 1 to 10 carbon atoms.

The term "lower alkyl" refers to an alkyl moiety having 1 to 7 carbon atoms. In particular embodiments the lower alkyl has 1 to 4 carbon atoms and in other particular embodiments the lower alkyl has 1 to 3 carbon atoms. Examples of lower alkyls include methyl, ethyl, propyl, isopropyl, butyl, isobutyl, sec-butyl and tert-butyl. Particular "lower alkyl" are methyl, ethyl, isopropyl and tert.-butyl.

The term "alkoxy" denotes a group of the formula —O—R', wherein R' is an alkyl group. Examples of alkoxy moieties include methoxy, ethoxy, isopropoxy, and tert-butoxy. A particular "lower alkoxy" is methoxy.

"Aryl" means a monovalent cyclic aromatic hydrocarbon moiety having a mono-, bi- or tricyclic aromatic ring. The aryl group can be optionally substituted as defined herein.

Examples of aryl moieties include, but are not limited to, phenyl, naphthyl, phenanthryl, fluorenyl, indenyl, pentalenyl, azulenyl, oxydiphenyl, biphenyl, methylenediphenyl, aminodiphenyl, diphenylsulfanyl, diphenylsulfonyl, diphenylisopropylidenyl, benzodioxanyl, benzofuranyl, benzodioxylyl, benzopyranyl, benzoxazinyl, benzoxazinonyl, benzopiperidinyl, benzopiperazinyl, benzopyrrolidinyl, benzomorpholinyl, methylenedioxyphenyl, ethylenedioxyphenyl, and the like, including partially hydrogenated derivatives thereof, each being optionally substituted.

The terms "halo", "halogen" and "halide", which may be used interchangeably, refer to a substituent fluoro, chloro, bromo or iodo.

Unless otherwise indicated, the term "hydrogen" or "hydro" refers to the moiety of a hydrogen atom (—H) and not $H_2$.

Unless otherwise indicated, the term "a compound of the formula" or "a compound of formula" or "compounds of the formula" or "compounds of formula" refers to any compound selected from the genus of compounds as defined by the formula (including any pharmaceutically acceptable salt or ester of any such compound if not otherwise noted).

The term "pharmaceutically acceptable salts" refers to those salts which retain the biological effectiveness and properties of the free bases or free acids, which are not biologically or otherwise undesirable. Salts may be formed with inorganic acids such as hydrochloric acid, hydrobromic acid, sulfuric acid, nitric acid, phosphoric acid and the like, preferably hydrochloric acid, and organic acids such as acetic acid, propionic acid, glycolic acid, pyruvic acid, oxalic acid, maleic acid, malonic acid, salicylic acid, succinic acid, fumaric acid, tartaric acid, citric acid, benzoic acid, cinnamic acid, mandelic acid, methanesulfonic acid, ethanesulfonic acid, p-toluenesulfonic acid, N-acetylcystein and the like. In addition, salts may be prepared by the addition of an inorganic base or an organic base to the free acid. Salts derived from an inorganic base include, but are not limited to, the sodium, potassium, lithium, ammonium, calcium, and magnesium salts and the like. Salts derived from organic bases include, but are not limited to salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, lysine, arginine, N-ethylpiperidine, piperidine, polyamine resins and the like.

The compounds of the present invention can be present in the form of pharmaceutically acceptable salts. The compounds of the present invention can also be present in the form of pharmaceutically acceptable esters (i.e., the methyl and ethyl esters of the acids of formula (I) to be used as prodrugs). The compounds of the present invention can also be solvated, i.e. hydrated. The solvation can be effected in the course of the manufacturing process or can take place i.e. as a consequence of hygroscopic properties of an initially anhydrous compound of formula (I) (hydration).

Compounds that have the same molecular formula but differ in the nature or sequence of bonding of their atoms or the arrangement of their atoms in space are termed "isomers" and fall within the scope of the invention. Isomers that differ in the arrangement of their atoms in space are termed "stereoisomers." Diastereomers are stereoisomers with opposite configuration at one or more chiral centers which are not enantiomers. Stereoisomers bearing one or more asymmetric centers that are non-superimposable mirror images of each other are termed "enantiomers." When a compound has an asymmetric center, for example, if a carbon atom is bonded to four different groups, a pair of enantiomers is possible. An enantiomer can be characterized by the absolute configuration of its asymmetric center or centers and is described by the R- and S-sequencing rules of Cahn, Ingold and Prelog, or by the manner in which the molecule rotates the plane of polarized light and designated as dextrorotatory or levorotatory (i.e., as (+) or (−)-isomers respectively). A chiral compound can exist as either individual enantiomer or as a mixture thereof. A mixture containing equal proportions of the enantiomers is called a "racemic mixture".

The term "a therapeutically effective amount" of a compound means an amount of compound that is effective to prevent, alleviate or ameliorate symptoms of disease or prolong the survival of the subject being treated. Determination of a therapeutically effective amount is within the skill in the art. The therapeutically effective amount or dosage of a compound according to this invention can vary within wide limits and may be determined in a manner known in the art. Such dosage will be adjusted to the individual requirements in each particular case including the specific compound(s) being administered, the route of administration, the condition being treated, as well as the patient being treated. In general, in the case of oral or parenteral administration to adult humans weighing approximately 70 Kg, a daily dosage of about 0.1 mg to about 5,000 mg, 1 mg to about 1,000 mg, or 1 mg to 100 mg may be appropriate, although the lower and upper limits may be exceeded when indicated. The daily dosage can be administered as a single dose or in divided doses, or for parenteral administration, it may be given as continuous infusion.

The term "pharmaceutically acceptable carrier" is intended to include any and all material compatible with pharmaceutical administration including solvents, dispersion media, coatings, antibacterial and antifungal agents, isotonic and absorption delaying agents, and other materials and compounds compatible with pharmaceutical administration. Except insofar as any conventional media or agent is incompatible with the active compound, use thereof in the compositions of the invention is contemplated. Supplementary active compounds can also be incorporated into the compositions.

Useful pharmaceutical carriers for the preparation of the compositions hereof, can be solids, liquids or gases; thus, the compositions can take the form of tablets, pills, capsules, suppositories, powders, enterically coated or other protected formulations (e.g. binding on ion-exchange resins or packaging in lipid-protein vesicles), sustained release formulations, solutions, suspensions, elixirs, aerosols, and the like. The carrier can be selected from the various oils including those of petroleum, animal, vegetable or synthetic origin, e.g., peanut oil, soybean oil, mineral oil, sesame oil, and the like. Water, saline, aqueous dextrose, and glycols are preferred liquid carriers, particularly (when isotonic with the blood) for injectable solutions. For example, formulations for intravenous administration comprise sterile aqueous solutions of the active ingredient(s) which are prepared by dissolving solid active ingredient(s) in water to produce an aqueous solution, and rendering the solution sterile. Suitable pharmaceutical excipients include starch, cellulose, talc, glucose, lactose, gelatin, malt, rice, flour, chalk, silica, magnesium stearate, sodium stearate, glycerol monostearate, sodium chloride, dried skim milk, glycerol, propylene glycol, water, ethanol, and the like. The compositions may be subjected to conventional pharmaceutical additives such as preservatives, stabilizing agents, wetting or emulsifying agents, salts for adjusting osmotic pressure, buffers and the like. Suitable pharmaceutical carriers and their formulation are described in Remington's Pharmaceutical Sciences by E. W. Martin. Such compositions will, in any event, contain an effective amount of the active compound together with a suitable carrier so as to prepare the proper dosage form for proper administration to the recipient.

In the practice of the method of the present invention, an effective amount of any one of the compounds of this invention or a combination of any of the compounds of this invention or a pharmaceutically acceptable salt or ester thereof, is administered via any of the usual and acceptable methods known in the art, either singly or in combination. The compounds or compositions can thus be administered orally (e.g., buccal cavity), sublingually, parenterally (e.g., intramuscularly, intravenously, or subcutaneously), rectally (e.g., by suppositories or washings), transdermally (e.g., skin electroporation) or by inhalation (e.g., by aerosol), and in the form of solid, liquid or gaseous dosages, including tablets and suspensions. The administration can be conducted in a single unit dosage form with continuous therapy or in a single dose therapy ad libitum. The therapeutic composition can also be in the form of an oil emulsion or dispersion in conjunction with a lipophilic salt such as pamoic acid, or in the form of a biodegradable sustained-release composition for subcutaneous or intramuscular administration.

In another embodiment, the present invention provides for a compound of formula (I) wherein A is —CH—.

In another embodiment, the present invention provides for a compound of formula (I) wherein R1 is —O—CH$_2$—R3.

In another embodiment, the present invention provides for a compound of formula (I) wherein R1 is —CH$_2$—O—R3.

In another embodiment, the present invention provides for a compound of formula (I) wherein R1 is —CH$_2$—R4.

In another embodiment, the present invention provides for a compound of formula (I) wherein R2 is hydrogen or chlorine.

In another embodiment, the present invention provides for a compound of formula (I) wherein R2 is hydrogen.

In another embodiment, the present invention provides for a compound of formula (I) wherein R2 is chlorine.

In another embodiment, the present invention provides for a compound of formula (I) wherein R3 is phenyl, mono- or bi-substituted independently with lower alkyl, alkoxy, halogen, —CN, —CF$_3$, —OCF$_3$, —SCF$_3$, —S(=O)CF$_3$, or —SO$_2$CH$_3$.

In another embodiment, the present invention provides for a compound of formula (I) wherein R3 is pyridinyl substituted with lower alkyl or halogen.

In another embodiment, the present invention provides for a compound of formula (I) wherein R4 is indolyl, dihydroindolyl, isoindolyl or dihydroisoindolyl.

In another embodiment, the present invention provides for a compound of formula (I) wherein R4 is benzotriazolyl, benzoimidazolyl, indazolyl, tetrahydroquinolinyl, methyldihydroindolyl or methylindolyl.

In another embodiment, the present invention provides for a compound of formula (I) wherein the compound is:

3-[4-(2-Trifluoromethylsulfanyl-benzyloxy)-phenyl]-isoxazole-5-carboxylic acid amide;
3-[4-(2-Trifluoromethanesulfinyl-benzyloxy)-phenyl]-isoxazole-5-carboxylic acid amide;
3-[4-(2-Methoxy-benzyloxy)-phenyl]-isoxazole-5-carboxylic acid amide;
3-[4-(3,4-Dimethyl-benzyloxy)-phenyl]-isoxazole-5-carboxylic acid amide;
3-[4-(2-Cyano-benzyloxy)-phenyl]-isoxazole-5-carboxylic acid amide;
3-[4-(2,6-Dichloro-benzyloxy)-phenyl]-isoxazole-5-carboxylic acid amide;
3-[4-(3,4-Difluoro-benzyloxy)-phenyl]-isoxazole-5-carboxylic acid amide;
3-[4-(2-Fluoro-benzyloxy)-phenyl]-isoxazole-5-carboxylic acid amide;
3-[4-(2-Methyl-benzyloxy)-phenyl]-isoxazole-5-carboxylic acid amide;
3-[4-(2-Trifluoromethoxy-benzyloxy)-phenyl]-isoxazole-5-carboxylic acid amide;
3-[4-(2-Iodo-benzyloxy)-phenyl]-isoxazole-5-carboxylic acid amide;
3-[4-(2-Chloro-6-fluoro-benzyloxy)-phenyl]-isoxazole-5-carboxylic acid amide;
3-[4-(2-Chloro-5-fluoro-benzyloxy)-phenyl]-isoxazole-5-carboxylic acid amide;
3-[5-(2-Chloro-benzyloxy)-pyridin-2-yl]-isoxazole-5-carboxylic acid amide;
3-[4-(2-Chloro-pyridin-3-ylmethoxy)-phenyl]-isoxazole-5-carboxylic acid amide;
3-[4-(3-Fluoro-benzyloxy)-phenyl]-isoxazole-5-carboxylic acid amide;
3-[4-(3-Trifluoromethyl-benzyloxy)-phenyl]-isoxazole-5-carboxylic acid amide;
3-[4-(3-Chloro-benzyloxy)-phenyl]-isoxazole-5-carboxylic acid amide;
3-[4-(2-Chloro-benzyloxy)-phenyl]-isoxazole-5-carboxylic acid amide;
3-[4-(2-Bromo-benzyloxy)-phenyl]-isoxazole-5-carboxylic acid amide;
3-[4-(2-Trifluoromethyl-benzyloxy)-phenyl]-isoxazole-5-carboxylic acid amide;
3-[4-(2-Methanesulfonyl-benzyloxy)-phenyl]-isoxazole-5-carboxylic acid amide;
3-[4-(2-Chloro-phenoxymethyl)-phenyl]-isoxazole-5-carboxylic acid amide;
3-[4-(3-Chloro-phenoxymethyl)-phenyl]-isoxazole-5-carboxylic acid amide;
3-[4-(4-Chloro-phenoxymethyl)-phenyl]-isoxazole-5-carboxylic acid amide;
3-(4-o-Tolyloxymethyl-phenyl)-isoxazole-5-carboxylic acid amide;
3-(4-m-Tolyloxymethyl-phenyl)-isoxazole-5-carboxylic acid amide;
3-[4-(2-Methoxy-phenoxymethyl)-phenyl]-isoxazole-5-carboxylic acid amide;
3-[4-(3-Methoxy-phenoxymethyl)-phenyl]-isoxazole-5-carboxylic acid amide;
3-[4-(4-Methoxy-phenoxymethyl)-phenyl]-isoxazole-5-carboxylic acid amide;
3-[4-(2,6-Dimethyl-phenoxymethyl)-phenyl]-isoxazole-5-carboxylic acid amide;
3-[4-(2-Isopropyl-phenoxymethyl)-phenyl]-isoxazole-5-carboxylic acid amide;
3-[4-(2-Trifluoromethoxy-phenoxymethyl)-phenyl]-isoxazole-5-carboxylic acid amide;
3-[4-(2-Ethyl-phenoxymethyl)-phenyl]-isoxazole-5-carboxylic acid amide;
3-[4-(2-tert-Butyl-phenoxymethyl)-phenyl]-isoxazole-5-carboxylic acid amide;
3-[4-(2-Trifluoromethyl-phenoxymethyl)-phenyl]-isoxazole-5-carboxylic acid amide;
3-[4-(2-Cyano-phenoxymethyl)-phenyl]-isoxazole-5-carboxylic acid amide;
3-[4-(3-Methyl-pyridin-2-yloxymethyl)-phenyl]-isoxazole-5-carboxylic acid amide;

3-[4-(2-Fluoro-phenoxymethyl)-phenyl]-isoxazole-5-carboxylic acid amide;

3-[4-(5-Chloro-2-methyl-phenoxymethyl)-phenyl]-isoxazole-5-carboxylic acid amide;

3-[4-(3-Chloro-2-methyl-phenoxymethyl)-phenyl]-isoxazole-5-carboxylic acid amide;

3-[4-(4-Fluoro-2-methyl-phenoxymethyl)-phenyl]-isoxazole-5-carboxylic acid amide;

3-[4-(5-Fluoro-2-methyl-phenoxymethyl)-phenyl]-isoxazole-5-carboxylic acid amide;

3-[4-(2-Methyl-pyridin-3-yloxymethyl)-phenyl]-isoxazole-5-carboxylic acid amide;

3-[4-(2,3-Dihydro-indol-1-ylmethyl)-phenyl]-isoxazole-5-carboxylic acid amide;

3-[4-(1,3-Dihydro-isoindol-2-ylmethyl)-phenyl]-isoxazole-5-carboxylic acid amide;

3-(4-Indol-1-ylmethyl-phenyl)-isoxazole-5-carboxylic acid amide;

3-(4-Benzotriazol-1-ylmethyl-phenyl)-isoxazole-5-carboxylic acid amide;

3-(4-Benzoimidazol-1-ylmethyl-phenyl)-isoxazole-5-carboxylic acid amide;

3-(4-Indazol-1-ylmethyl-phenyl)-isoxazole-5-carboxylic acid amide;

3-(4-Indazol-2-ylmethyl-phenyl)-isoxazole-5-carboxylic acid amide;

3-[4-(3,4-Dihydro-2H-quinolin-1-ylmethyl)-phenyl]-isoxazole-5-carboxylic acid amide;

3-[4-(2-Methyl-2,3-dihydro-indol-1-ylmethyl)-phenyl]-isoxazole-5-carboxylic acid amide;

3-[4-(4-Methyl-indol-1-ylmethyl)-phenyl]-isoxazole-5-carboxylic acid amide; or

3-[3-Chloro-4-(2-trifluoromethyl-benzyloxy)-phenyl]-isoxazole-5-carboxylic acid amide.

In another embodiment, the invention provides for a pharmaceutical composition, comprising a therapeutically effective amount of a compound according to formula (I) and a pharmaceutically acceptable carrier.

In another embodiment, the invention provides for a compound according to formula (I) for use as a therapeutically active substance.

In another embodiment, the invention provides for the use of a compound according to formula (I) for the treatment of cancer.

In another embodiment, the invention provides for the use of a compound according to formula (I) for the preparation of a medicament for the treatment of cancer.

In another embodiment, the invention provides for a compound according to formula (I) for use in the treatment of cancer.

In another embodiment, the invention provides for a method for treating cancer, comprising the step of administering a therapeutically effective amount of a compound according to formula (I) to a subject in need thereof.

In another embodiment, provided is an invention as hereinbefore described.

Compounds of the present invention can be prepared beginning with commercially available starting materials and utilizing general synthetic techniques and procedures known to those skilled in the art. Outlined below are reaction schemes suitable for preparing such compounds. Further exemplification is found in the specific examples listed below.

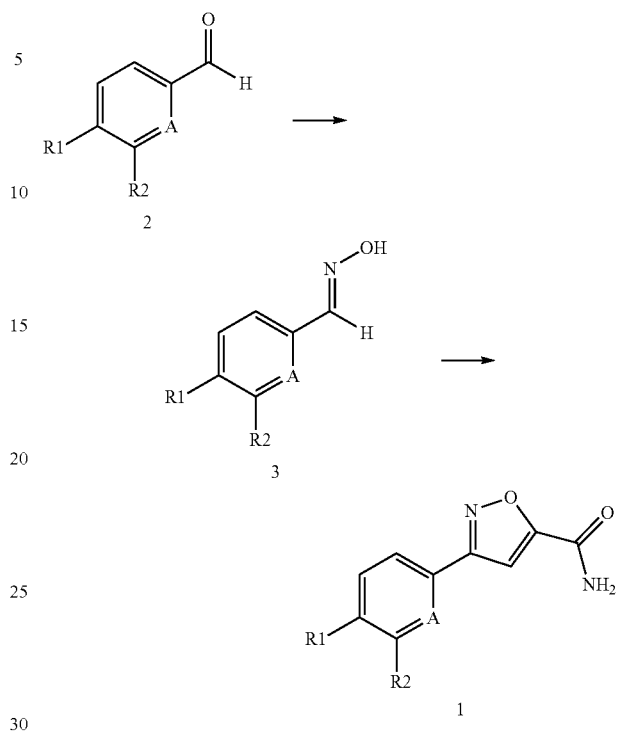

Scheme 1

Compounds of the invention may be made by any conventional means. For example, they may be made according to the process outlined in Scheme 1, where A, R1, and R2 are as described above. According to this process, an aldehyde of formula 2, is treated with hydroxylamine to form the oxime, which undergoes oxidation with N-chlorosuccinimide followed by a [2,3]-dipolar cycloaddition with propiolamide to give the compound of the invention of formula 1. The formation of the oxime of formula 3 can be conveniently effected by treating the aldehyde of formula 2 with hydroxylamine hydrochloride in the presence of an inorganic base such as sodium acetate or sodium hydroxide in an inert solvent such as an alcohol (e.g., methanol or ethanol or tert-butanol) or a mixture of such an alcohol and water at a temperature around the reflux temperature of the solvent(s), or in the presence of an organic base such as triethylamine or diisopropylethylamine in a solvent such as dichloromethane or in pyridine between about room temperature and about the reflux temperature of the solvent(s). Examples of conditions for such a reaction can be found in the literature, for example in Kao, Y. T. R. et al. US 20110212975; in Charrier, J.-D. et al. WO2011/143426; in Nakano, Y. et al. J. Med. Chem. 2006, 49, 2398-2406 Supporting information; and in Liu, K. C. et al. J. Org. Chem. 1980, 45, 3916-3918.

The reaction of an oxime of formula 3 to give an isoxazole of formula 1 can be carried out using a [2,3]-dipolar cycloaddition reaction. The oxime of formula 3 is first treated with an oxidizing agent such as sodium hypochlorite or N-chlorosuccinimide in an inert solvent such as DMF at about room temperature to form the oximinoyl chloride. This is then treated with propiolamide in the presence of a reducing agent such as sodium ascorbate, a copper salt such as copper(II) sulfate, and an inorganic base such as potassium hydrogen carbonate or sodium hydrogen carbonate. The reaction is conveniently carried out in a solvent such a 50:50 mixture of water and tert-butanol at a temperature around room temperature.

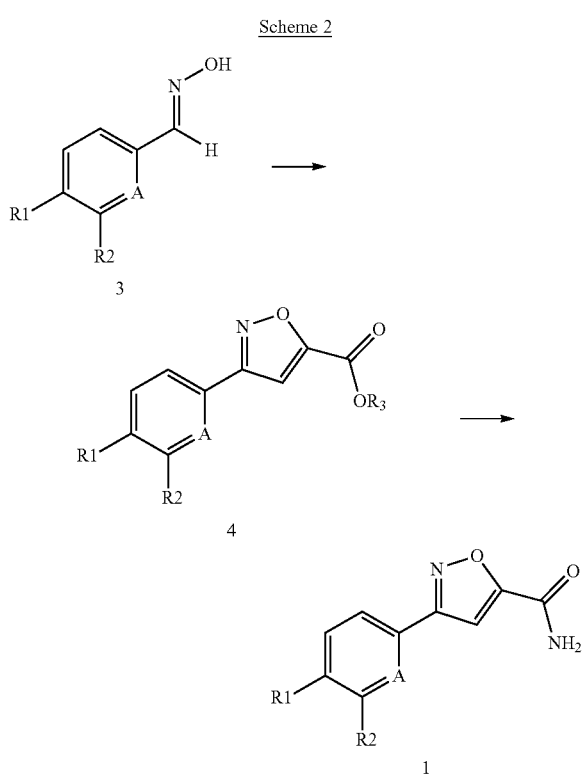

It will be apparent to one of ordinary skill in the art of organic synthesis that the oxime of formula 3 can also undergo a [2,3]-dipolar cycloaddition with a loweralkyl ester of propiolic acid such as the methyl or ethyl esters to give the compound of formula 4, as shown in Scheme 2. The ester of formula 4 can then be converted into the primary amide of formula 1 using one of a variety of approaches that are well known in the field of organic synthesis. For the preparation of the isoxazole derivative of formula 4, the oxime of formula 3 is first treated with an oxidizing agent such as sodium hypochlorite or N-chlorosuccinimide in an inert solvent such as DMF at about room temperature to form the oximinoyl chloride. This is then treated with methyl or ethyl propiolate in the presence of a reducing agent such as sodium ascorbate, a copper salt such as copper(II) sulfate, and an inorganic base such as potassium hydrogen carbonate or sodium hydrogen carbonate. The reaction is conveniently carried out in a solvent such a 50:50 mixture of water and tert-butanol at a temperature around room temperature. Alternatively, the [2,3]-dipolar cycloaddition may proceed using methyl or ethyl propiolate in the presence an amine base such as triethylamine and a convenient solvent such as DMF or THF at temperatures between room temperature and 80° C. Examples of these conditions can be found in the literature in Lee, C. K. Y. et al. *J. Chem. Soc. Perkin Trans.* 2, 2002, 12, 2031-2038. The resulting compound of formula 4 may then be treated with an ethanolic solution of ammonia, which may be purchased from a commercial source such as Aldrich Chemical Company, Inc., 1001 West Saint Paul Avenue, Milwaukee, Wis. 53233, USA or which may be prepared by bubbling ammonia gas through ethanol until the solution is saturated. The treatment of the ester of formula 4 with ethanolic ammonia is conveniently carried out at about room temperature. Alternatively, the ester of formula 4 may be hydrolyzed and then treated with ammonia or an acid addition salt thereof in the presence of a coupling agent. For example, the ester of formula 4 may be treated with an alkali metal hydroxide such as lithium hydroxide or sodium hydroxide in a solvent such as a mixture of water and tetrahydrofuran in the optional additional presence of methanol or ethanol at room temperature to give the corresponding carboxylic acid. The acid may then be treated with ammonium chloride in the presence of a coupling agent, many of which are known in the field of organic synthesis, in the optional additional presence of a catalyst such as 1-hydroxybenzotriazole or 1-hydroxy-7-azabenzotriazole, and in the presence of a base such as pyridine or triethylamine or diisopropylethylamine, in a solvent such as dichloromethane or tetrahydrofuran or dimethylformamide, to give the compound of the invention of formula 1. Examples of coupling agents that may be useful in the amide formation are: O-(benzotriazol-1-yl)-1,1,3,3-tetramethyluronium hexafluorophosphate (HBTU) or O-(7-azabenzotriazol-1-yl)-N,N,N',N'-tetramethyluronium hexafluorophosphate (HATU) or (O—(N-succinimidyl)-1,1,3,3-tetramethyluronium tetrafluoroborate) (TSTU) or benzotriazol-1-yl-oxy-tris-(dimethylamino)-phosphonium hexafluorophosphate or bis(2-oxo-3-oxazolidinyl)phosphinic chloride or N'-(3-dimethylaminopropyl)-N-ethylcarbodiimide hydrochloride.

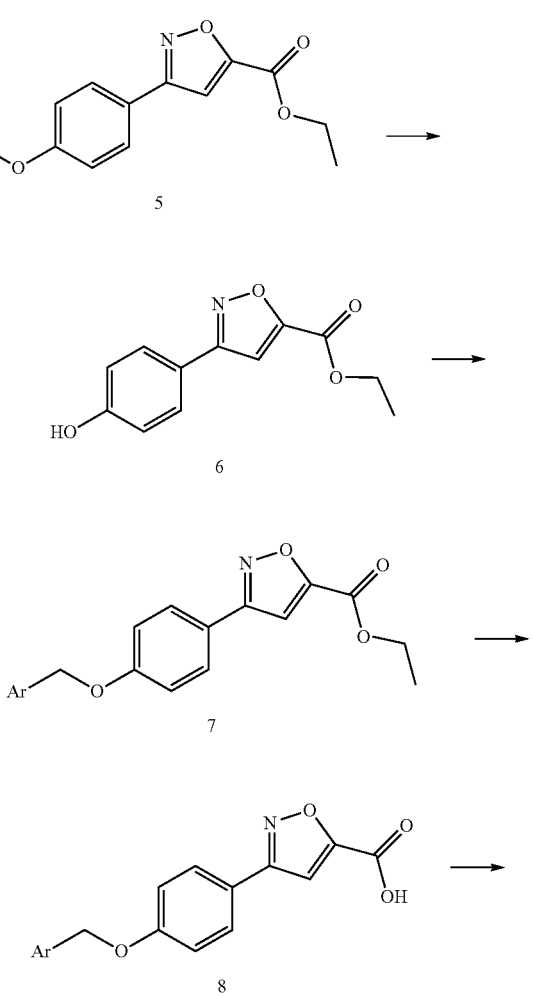

-continued

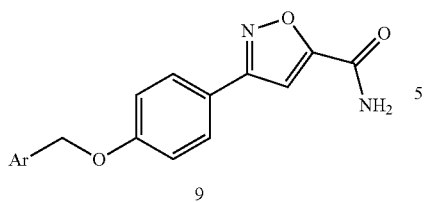

5

9

-continued

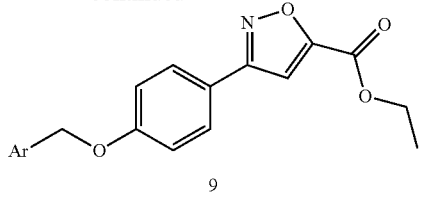

9

As shown in Scheme 3, certain compounds of the invention may be made starting from 3-(4-methoxy-phenyl)-isoxazole-5-carboxylic acid ethyl ester, the compound of formula 5, which is commercially available from vendors such as ChemDiv, Inc., 6605 Nancy Ridge Dr, San Diego, Calif., 92121, USA. The compound of formula 5 may be dealkylated by treating it with boron tribromide in dichloromethane at room temperature, to give the phenol of formula 6. The phenol can be alkylated using an arylmethyl bromide of formula $ArCH_2Br$ or an arylmethyl chloride of formula $ArCH_2Cl$. The reaction is conveniently carried out by treating the phenol of formula 6 with the arylmethyl chloride or aryl bromide in the presence of a base such as potassium carbonate and in the presence of a phase transfer catalyst such as tetrabutylammonium iodide in a solvent such as dimethylformamide or tetrahydrofuran at about room temperature. The product of this reaction, of formula 7, may then be converted to the primary carboxamide of the invention of formula 9 by hydrolysis of the ester followed by amidation with ammonium chloride using conditions similar to those described for the conversion of the compound of formula 4 to the compound of formula 1 in Scheme 2.

As shown in Scheme 4, compounds of the invention of formula 9 may also be prepared starting from 4-(tert-butyl-dimethyl-silanyloxy)-benzaldehyde oxime (which has formula 10), which may be prepared as described in the patent literature, in Kao, Y. T. R. et al. US 20110212975 page 17. The oxime of formula 10 may be converted to the isoxazole-carboxylic acid ethyl ester of formula 11 using reactions that are analogous to those described for the conversion of the oxime of formula 3 to the ester of formula 4 in Scheme 2. The intermediate of formula 11 may then be treated with a saturated solution of ammonia in ethanol at room temperature to give the primary carboxamide of formula 12. The intermediate of formula 12 may then be treated with an aryl bromide of formula $ArCH_2Br$ or an aryl chloride of formula $ArCH_2Cl$ in the presence of a base such as potassium carbonate; potassium fluoride; and 18-crown-6, in dimethylformamide at about room temperature to give the compound of the invention of formula 9.

Scheme 4

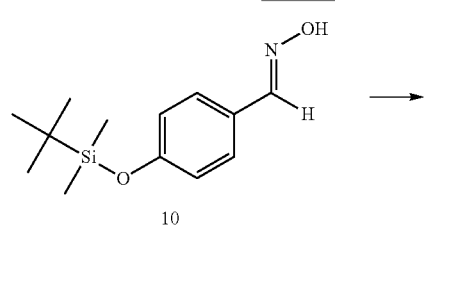

Scheme 5

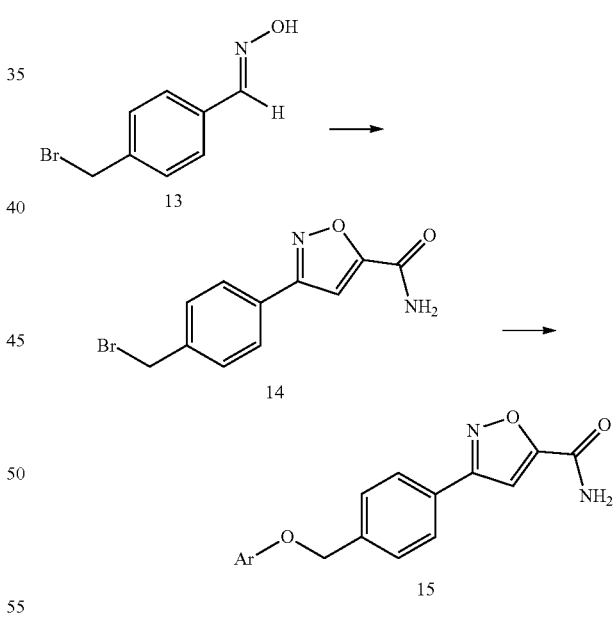

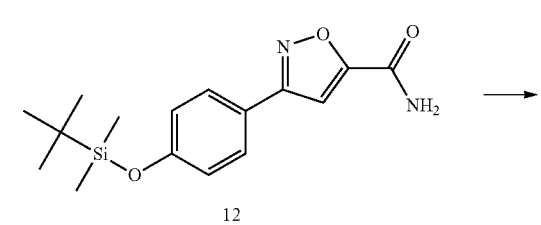

As shown in Scheme 5, compounds of the invention of formula 15 may also be prepared starting from 4-bromomethyl-benzaldehyde oxime (which has formula 13), which may be prepared as described in the patent literature, in Charrier, J.-D. et al. WO 2011143426 page 77. The oxime of formula 13 is first treated with an oxidizing agent such as sodium hypochlorite or N-chlorosuccinimide in an inert solvent such as DMF at about room temperature to form the oximinoyl chloride. This is then treated with propiolamide in the presence of a reducing agent such as sodium ascorbate, a copper salt such as copper(II) sulfate, and an inorganic base such as potassium hydrogen carbonate or sodium hydrogen carbonate. The reaction is conveniently carried out in a solvent such a 50:50 mixture of water and tert-butanol at a temperature around room temperature, and the product is the bromomethyl derivative of formula 14. The compound of formula 14 may then be treated with a hydroxyaromatic compound of formula ArOH in the presence of a base such as potassium carbonate in a solvent such as dimethylformamide or tetrahydrofuran at a temperature between about 50° C. and about 100° C. to give the compound of the invention of formula 15.

Scheme 6

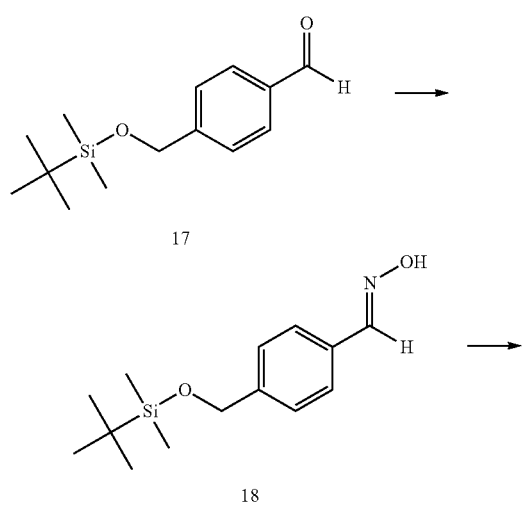

14

16

As shown in Scheme 6, compounds of the invention of formula 16, where Q represents a bicyclic heterocycle attached through a ring nitrogen atom, may be made by treating the heterocycle with sodium hydride in dimethylformamide at room temperature, followed by treatment with the bromomethyl derivative of formula 14, again at about room temperature. Alternatively, the reaction may be carried out by treating the bromomethyl derivative of formula 14 with the bicyclic heterocycle in the presence of a base such as potassium carbonate in a solvent such as acetonitrile or dimethylformamide at a temperature between about 50° C. and about 100° C.

Scheme 7

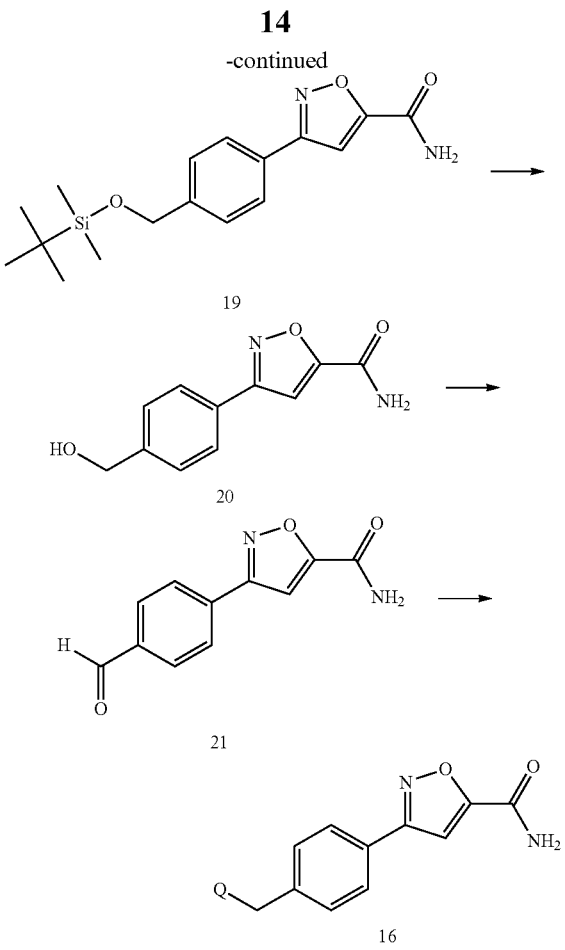

As shown in Scheme 7, compounds of the invention of formula 16, where Q represents a partially unsaturated bicyclic heterocycle attached through a nitrogen in the unsaturated ring, may be prepared starting from the aldehyde of formula 17, which may be prepared as described in the literature, in Barluenga, J. et al. *Synthesis* 1995, 1529-1533. According to this process, the aldehyde is converted to the oxime by treatment with hydroxylamine hydrochloride in the presence of an organic base such as triethylamine or diisopropylethylamine in a solvent such as dichloromethane or in pyridine between about room temperature and about 50° C. The product of this reaction, the oxime of formula 18 has been reported in the literature, but without a detailed description of its preparation (Yang, S. H. and Chang, S. *Org. Lett.* 2001, 3, 4209-4211). The oxime of formula 18 may then treated with an oxidizing agent such as sodium hypochlorite or N-chlorosuccinimide in an inert solvent such as DMF at about room temperature to form the oximinoyl chloride. This is then treated with propiolamide in the presence of a reducing agent such as sodium ascorbate, a copper salt such as copper(II) sulfate, and an inorganic base such as potassium hydrogen carbonate or sodium hydrogen carbonate. The reaction is conveniently carried out in a solvent such a 50:50 mixture of water and tert-butanol at a temperature around room temperature, and the product is the silyl ether derivative of formula 19. The intermediate of formula 19 is treated with HF/pyridine or tetrabutylammonium fluoride in tetrahydrofuran at about room temperature to give the alcohol of formula 20. The alcohol may be oxidized using one of a number of reagents that are familiar to one of average skill in the art of organic synthesis. For example, the alcohol of formula 20 may be treated with Des s-Martin periodinane in dimethylsulfoxide at room temperature to give the aldehyde of formula 21. The aldehyde may then be converted to the compound of the invention of formula 16 using a process called reductive amination. According to this process, the aldehyde is treated with the partially unsaturated bicyclic heterocycle in the presence of a reducing agent such as sodium borohydride, or preferably sodium cyanoborohydride or sodium triacetoxyborohydride, in 1,2-dichloroethane at about room temperature.

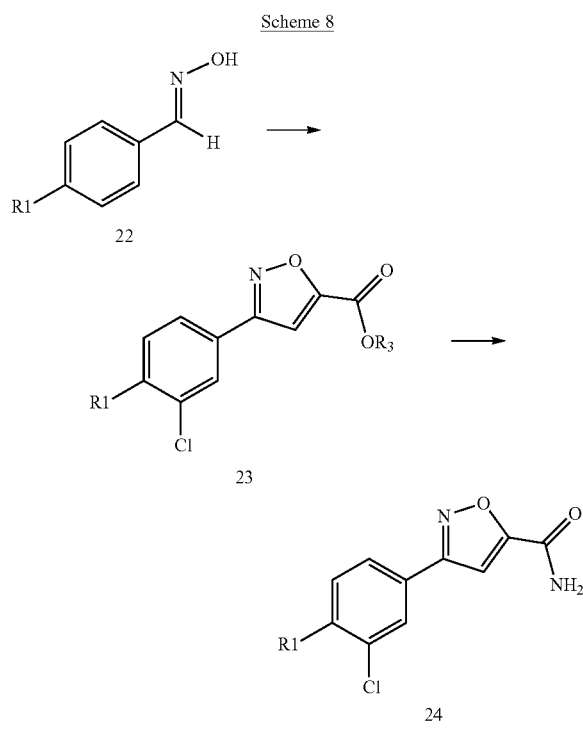

As shown in Scheme 8, an oxime of formula 22, which is an example of an oxime of formula 3 in which R2 represents hydrogen, may be treated with excess N-chlorosuccinimide or tert-butyl hypochloride in an inert solvent such as DMF at about room temperature. This is then treated with methyl or ethyl propiolate in the presence of a reducing agent such as sodium ascorbate, a copper salt such as copper(II) sulfate, and an inorganic base such as potassium hydrogen carbonate or sodium hydrogen carbonate. The reaction is conveniently carried out in a solvent such a 50:50 mixture of water and tert-butanol at a temperature around room temperature and gives the ester of formula 23 as the product. The intermediate of formula 23 may then be treated with a saturated solution of ammonia in ethanol at room temperature to give the primary carboxamide of formula 24.

Many compounds of formula 2 are commercially available and examples are shown below.

From Aldrich Chemical Company, Inc., 1001 West Saint Paul Avenue, Milwaukee, Wis. 53233, USA: 4-benzyloxy-benzaldehyde; 4-[(3,4-dichlorobenzyl)oxy]benzaldehyde; 4-[(2-chlorobenzyl)oxy]benzaldehyde; 4-(4-bromobenzyloxyl)benzaldehyde; 4-[(2-chloro-4-fluorobenzyl)oxy]benzaldehyde; and 4-([3-(trifluoromethyl)benzyl]oxy)benzaldehyde.

From Alfa Aesar, 26 Parkridge Road, Ward Hill, Mass. 01835, USA: 4-(4-nitrobenzyloxyl)benzaldehyde.

From Chem-Impex International, Inc., 935 Dillon Drive, Wood Dale, Ill. 60191, USA: 4-(2,6-difluoro-benzyloxy)-benzaldehyde.

From Combi-Blocks Inc., 7949 Silverton Avenue, Suite 915, San Diego, Calif. 92126, USA: 4-(3-fluoro-benzyloxy)-benzaldehyde and 4-(benzyloxy)-3-chlorobenzaldehyde.

From Matrix Scientific, P.O. Box 25067, Columbia, S.C. 29224-5067, USA: 4-(2-chloro-6-fluorobenzyloxy)benzaldehyde; 4-(4-fluorobenzyloxyl)benzaldehyde; 4-[(2,4-dichlorobenzyl)oxy]benzaldehyde; 4-[(4-methylbenzyl)oxy]benzaldehyde; 4-[(4-chlorobenzyl)oxy]benzaldehyde; 4-[(3-chlorobenzyl)oxy]benzenecarbaldehyde; 4-[(2-methylbenzyl)oxy]benzaldehyde; 4-[(3-methylbenzyl)oxy]benzaldehyde; 4-[(2,6-dichlorobenzyl)oxy]benzaldehyde; 4-[(3-methoxybenzyl)oxy]benzaldehyde; 4-[(2-bromobenzyl)oxy]benzaldehyde; and 4-[(3,4-difluorobenzyl)oxy]benzenecarbaldehyde.

From Oakwood Products, Inc., 1741 Old Dunbar Road, West Columbia, S.C. 29172, USA: 4-(2-fluorobenzyloxyl)benzaldehyde; 4-[(3-bromobenzyl)oxy]benzaldehyde; 4-(3,4-diethoxy-benzyloxy)-benzaldehyde; 4-(benzo[1,3]dioxol-5-ylmethoxy)-benzaldehyde; 3-chloro-4-[(4-fluorophenyl)methoxy]benzaldehyde; 2-(2-chloro-4-formylphenoxymethyl)benzonitrile; 3-chloro-4-[(2-fluorophenyl)methoxy]benzaldehyde; and 3-chloro-4-[(3-fluorophenyl)methoxy]benzaldehyde.

Many compounds of formula 2 that are not commercially available can be readily synthesized using reactions that are well known in the field of organic synthesis.

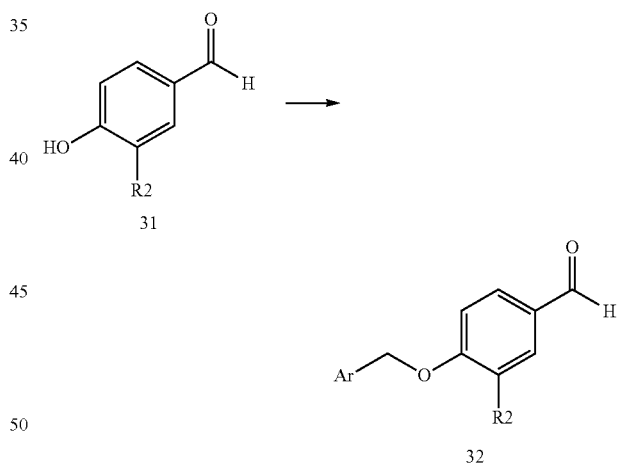

As shown in Scheme 9, aldehydes of formula 31 can be alkylated to give aldehydes of formula 32 (that is, compounds of formula 2 in which R1 represents ArCH$_2$O and A represents CH). The reaction is conveniently carried out by treating the phenol of formula 31 with an arylmethyl bromide of formula ArCH$_2$Br or an arylmethyl chloride of formula ArCH$_2$Cl in the presence of a base such as potassium carbonate or cesium carbonate and in the optional presence of a phase transfer catalyst such as tetrabutylammonium iodide in a solvent such as dimethylformamide or tetrahydrofuran at about room temperature. Examples of precise conditions to effect this reaction may be found in the literature, for example in Epple, R. et al. US 20090192203 page 18; in Akerman, M. et al. US 20060004012 page 31; in Hasuoka, A. et al. US 20120196864 page 38; in Woo, L. W. L. et al. *J. Med. Chem.* 2007, 50, 3540-3560; and in Dawson, M. I. et al. *J. Med. Chem.* 2007, 50, 2622-2639.

Scheme 10

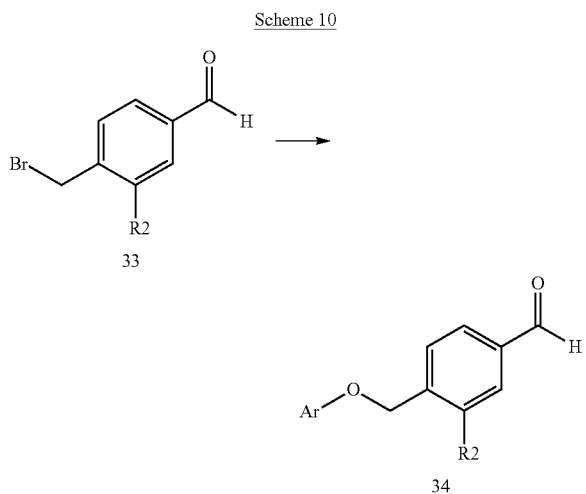

As shown in Scheme 10, aldehydes of formula 33 undergo reaction with hydroxy-substituted aromatics to give aldehydes of formula 34 (that is, compounds of formula 2 in which R1 represents —CH$_2$—O—Ar and A represents CH). The reaction is conveniently carried out by treating the bromomethyl derivative of formula 33 with a hydroxylated aromatic of formula ArOH in the presence of a base such as potassium carbonate or cesium carbonate and in the optional presence of a phase transfer catalyst such as tetrabutylammonium iodide in a solvent such as dimethylformamide or tetrahydrofuran at about room temperature. Examples of precise conditions to effect this reaction may be found in the literature, for example in Gutsmiedl, K. et al. *Chem. Eur. J.* 2010, 16, 6877-6883 Supporting Information page 8; and in Panetta, J. A. et al. U.S. Pat. No. 5,747,517 Column 10.

Scheme 11

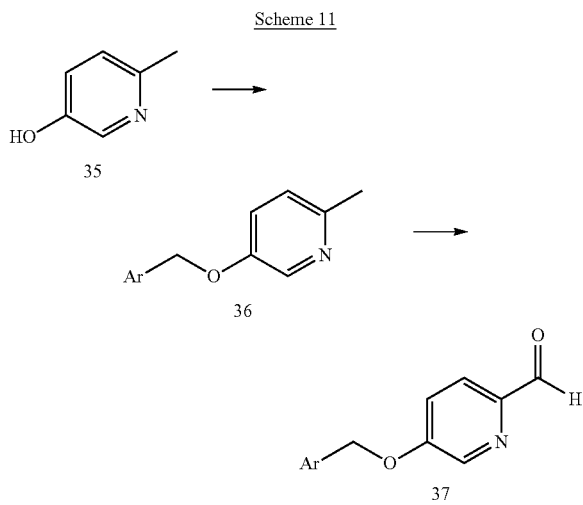

As shown in Scheme 11, aldehydes of formula 37 (that is, compounds of formula 2 where R1 represents —O—CH$_2$—Ar; R2 represents hydrogen; and A represents N) may be made in five steps from 5-hydroxy-2-methylpyridine (which has formula 35), which is commercially available from vendors such as Aldrich Chemical Company, Inc., 1001 West Saint Paul Avenue, Milwaukee, Wis. 53233, USA. The first step is conveniently carried out by treating the compound of formula 35 with an aryl chloride of formula ArCH$_2$Cl or an aryl bromide of formula ArCH$_2$Br in the presence of a base such as potassium carbonate and in the optional presence of a phase transfer catalyst such as tetrabutylammonium iodide in a solvent such as dimethylformamide or tetrahydrofuran at about room temperature. The methylpyridine of formula 36 may then be oxidized by treatment with meta-chloroperoxybenzoic acid (MCPBA) in chloroform at about 0° C. to give the pyridine N-oxide. Treatment with acetic anhydride at about 130° C. then gives the 2-acetoxypyridine derivative. The acetate group is then removed by treatment with sodium hydroxide in aqueous ethanol at the reflux temperature, and finally the benzylic alcohol is oxidized to the aldehyde of formula 37 using manganese dioxide in chloroform. An example of specific conditions to effect such a transformation may be found in the literature in Takeda et al. *Bioorg. Med. Chem.* 2003, 11, 4431-4447.

Many arylmethyl bromides of formula ArCH$_2$Br and arylmethyl chlorides of formula ArCH$_2$Cl are commercially available and examples are shown below.

From Acros Organics, Janssen Pharmaceuticalaan 3A, 2440 Geel, Belgium: 2-methylbenzyl bromide; 4-bromobenzyl bromide; 3-(trifluoromethyl)benzyl bromide; 2,4-dichlorobenzyl chloride; 3-(trifluoromethyl)benzyl chloride; 2,5-difluorobenzyl bromide; 4-(chloromethyl)pyridine hydrochloride; 4-(trifluoromethyl)benzyl chloride; 4-(bromomethyl)-2,6-dichloropyridine; and 3-methoxybenzyl bromide.

From Aldrich Chemical Company, Inc., 1001 West Saint Paul Avenue, Milwaukee, Wis. 53233, USA.: benzyl bromide; 3-bromobenzyl bromide; 3-fluorobenzyl bromide; 2-fluorobenzyl chloride; 2,6-dichlorobenzyl chloride; 2-iodobenzyl chloride; 2-cyanobenzyl bromide; 2-(chloromethyl)pyridine hydrochloride; 4-isopropylbenzyl chloride; 4-(chloromethyl)benzonitrile; and 4-iodobenzyl bromide.

From Alfa Aesar, 26 Parkridge Road, Ward Hill, Mass. 01835, USA: 2-bromobenzyl bromide; 3-methylbenzyl bromide; 4-fluorobenzyl bromide; 2-chlorobenzyl chloride; 3-chlorobenzyl chloride; 4-cyanobenzyl bromide; 3,5-dimethylbenzyl bromide; 4-ethylbenzyl chloride; 4-(trifluoromethoxy)benzyl chloride; and 2-(trifluoromethoxy)benzyl bromide.

From Chem-Impex International, Inc., 935 Dillon Drive, Wood Dale, Ill. 60191, USA: 4-methylbenzyl bromide; 2-chlorobenzyl bromide; 4-methoxybenzyl chloride; 4-methylbenzyl chloride; and 3,5-difluorobenzyl bromide.

From Combi-Blocks Inc., 7949 Silverton Avenue, Suite 915, San Diego, Calif. 92126, USA: 4-tert-butylbenzyl bromide; 2,6-dichlorobenzyl bromide; 3-methoxybenzyl chloride; 3-cyanobenzyl bromide; 2-(chloromethyl)benzonitrile; 4-chlorobenzyl bromide; 4-bromobenzyl chloride; 2-chloro-5-chloromethylpyridine; 2-iodobenzyl bromide; 2-(chloromethyl)-4,6-dimethoxypyrimidine.

From Matrix Scientific, P.O. Box 25067, Columbia, S.C. 29224-5067, USA: 2,6-difluorobenzyl bromide; 2,4,6-trimethylbenzyl chloride; 2,5-dimethylbenzyl chloride; 3,4-dimethylbenzyl chloride; 2-(trifluoromethyl)benzyl chloride; 2,4-dimethylbenzyl chloride; 2,3-dichlorobenzyl chloride; 2-bromobenzyl chloride; 3,4-difluorobenzyl chloride.

From Oakwood Products, Inc., 1741 Old Dunbar Road, West Columbia, S.C. 29172, USA: 2-fluorobenzyl bromide; 3-chlorobenzyl bromide; 3-fluorobenzyl chloride; 4-fluorobenzyl chloride; 2-(trifluoromethyl)benzyl bromide;

2-chloro-6-fluorobenzyl bromide; 3,4-dichlorobenzyl bromide; 4-methoxy-3-methylbenzyl chloride; and 4-(methylthio)benzyl chloride.

From TCI America, 9211 N. Harborgate Street, Portland, Oreg. 97203, USA: 4-(trifluoromethyl)benzyl bromide; benzyl chloride; 2-chloro-6-fluorobenzyl chloride; 2-methylbenzyl chloride; 3-methylbenzyl chloride; 3,4-difluorobenzyl bromide; 2,4-difluorobenzyl bromide; 3-(chloromethyl)pyridine hydrochloride; 3-iodobenzyl bromide; 3-bromobenzyl chloride; 2-chloro-4-fluorobenzyl chloride; and 2,6-dimethylbenzyl chloride.

In addition, there are several procedures that are well known to one of average skill in the art of organic synthesis that can be used to prepare arylmethyl bromides of formula $ArCH_2Br$ and arylmethyl chlorides of formula $ArCH_2Cl$. For example, an arylmethyl chloride of formula $ArCH_2Cl$, can be prepared from a compound of formula ArH by an electrophilic aromatic substitution reaction by treating the compound of formula ArH with formaldehyde and hydrogen chloride, in the presence of a Lewis acid catalyst, preferably zinc chloride, in a suitable inert solvent, for example, a halogenated alkane (such as methylene chloride, chloroform, 1,2-dichloroethane, or the like) at a temperature between about room temperature and the boiling point of the solvent, preferably at about 35 degrees celsius. Clearly this reaction is limited to cases where the compound of formula ArH is susceptible to electrophilic aromatic substitution at the desired point of attachment, and further, to cases where the compound of formula ArH is stable to mineral acids and to Lewis acids. Examples of compounds of formula ArH which fulfill these criteria will be known to one of average skill in the art. An example of such a reaction can be found in O. Moldenhauer et al. *Justus Liebigs Ann. Chem.* 1953, 580, 176.

Arylmethyl bromides of formula $ArCH_2Br$ can be prepared by treating a compound of formula $ArCH_3$ with N-bromosuccinimide or 3,3-dimethyl-N,N'-dibromohydantoin in an inert solvent such as a halogenated alkane (for example, carbon tetrachloride) or acetonitrile, in the optional additional presence of a catalyst such as azobis(isobutyronitrile) or benzoyl peroxide at a suitable temperature, conveniently at the boiling point of the solvent, and in the optional additional presence of a source of light; or by treating a compound of formula $ArCH_3$ with bromine in an inert solvent such as a mixture of water and an aromatic hydrocarbon (e.g., benzene) or a halogenated alkane (e.g., chloroform) under irradiation with an incandescent light. Arylmethyl chlorides of formula $ArCH_2Cl$ can be prepared by treating a compound of formula $ArCH_3$ with N-chlorosuccinimide or sulfuryl chloride in an inert solvent such as a halogenated alkane (for example, carbon tetrachloride) or acetonitrile in the optional additional presence of a catalyst such as azobis(isobutyronitrile) or benzoyl peroxide at a suitable temperature, conveniently at the boiling point of the solvent, and in the optional additional presence of a source of light; or by treating a compound of formula $ArCH_3$ with chlorine in an inert solvent such as a mixture of water and an aromatic hydrocarbon (e.g., benzene) or a halogenated alkane (e.g., chloroform or carbon tetrachloride) under irradiation with an incandescent light.

An arylmethyl bromide of formula $ArCH_2Br$ can be prepared by treating a compound of formula $ArCH_2OH$ with phosphorus tribromide or a mixture of N-bromosuccinimide and triphenylphosphine in an inert solvent such as a halogenated alkane (e.g., methylene chloride or carbon tetrachloride) at a temperature between about 0 degrees and the boiling point of the solvent, conveniently at about 0 degrees. An arylmethyl chloride of formula $ArCH_2Cl$ can be prepared by treating a compound of formula $ArCH_2OH$ with thionyl chloride or a mixture of N-chlorosuccinimide and triphenylphosphine in an inert solvent such as a halogenated alkane (e.g., methylene chloride or carbon tetrachloride) at a temperature between about 0 degrees and the boiling point of the solvent, conveniently at about 0 degrees.

Many hydroxyaromatic compounds of formula ArOH are commercially available and examples are shown below.

From Acros Organics, Janssen Pharmaceuticalaan 3A, 2440 Geel, Belgium: 4-hydroxythiophenol; 3-(trifluoromethoxy)phenol; 2,4-dichlorophenol; 2,5-dichlorophenol; 2-ethylphenol; m-cresol; 2,4-difluorophenol; 2-chloro-5-fluorophenol; 4-chloro-2-fluorophenol; 4-fluoro-2-methylphenol.

From Aldrich Chemical Company, Inc., 1001 West Saint Paul Avenue, Milwaukee, Wis. 53233, USA: 3,5-dichlorophenol; 4-cyanophenol; 4-isopropylphenol; 3,4-dimethoxyphenol; 4-bromo-2-fluorophenol; 5-chloro-2-methylphenol; 4-fluoro-2-methoxyphenol; 4-hydroxyphthalonitrile; 2-bromophenol; 2-fluorophenol; 2,3,5-trimethylphenol; 3-chlorophenol; 3-diethylaminophenol; 3-(trifluoromethyl)phenol; 3-tert-butylphenol; 3,4,5-trimethylphenol; 4-chloro-2-methylphenol; 4-propoxyphenol; 4-hydroxyphenylacetonitrile; 4-ethyl-2-methoxyphenol; 2-chloro-4-methylphenol; o-eugenol; 3,5-dimethyl-4-hydroxybenzonitrile; 2,4-diisopropylphenol; and 3-hydroxy-2-methylpyridine.

From Alfa Aesar, 26 Parkridge Road, Ward Hill, Mass. 01835, USA: 4-hydroxy-3-methoxybenzonitrile; 2-allylphenol; 2-n-propylphenol; propofol; 2,3,4-trifluorophenol; phenol; 3-dimethylaminophenol; 3-methoxyphenol; 4-methoxyphenol; p-cresol; 2-methoxy-4-methylphenol; 4-ethylphenol; 2,3-dimethoxyphenol; 3-ethoxyphenol; 2-chloro-6-methylphenol; 3-hydroxyphenylacetylene; 2,3-difluoro-4-hydroxybenzonitrile; 2,6-difluoro-3-methylphenol; 2,3-difluoro-4-methoxyphenol; 5-fluoro-2-hydroxy-n,n-dimethylbenzylamine; 2,3-difluoro-6-methoxyphenol; 1-hydroxy-4-ethoxy-2,3-difluorobenzene; 5-bromo-2-methylphenol; 2-methyl-3-(trifluoromethyl)phenol; and 3-hydroxy-5-methylpyridine; 6-(trifluoromethyl)pyridin-3-ol; and 2,4,5-trimethyl-3-pyridinol.

From Chem-Impex International, Inc., 935 Dillon Drive, Wood Dale, Ill. 60191, USA: 3,5-dimethoxyphenol; 4-(2-methoxy-ethoxy)-phenol; and 3-hydroxypyridine.

From Combi-Blocks Inc., 7949 Silverton Avenue, Suite 915, San Diego, Calif. 92126, USA: 3-fluoro-4-hydroxybenzonitrile; 4-(trifluoromethyl)phenol; 2-(methylsulfinyl)phenol; 3-fluoro-5-hydroxybenzonitrile; and 2-chloro-5-hydroxypyridine; 3-bromo-5-hydroxypyridine; 2-fluoro-5-hydroxypyridine; 3-fluoro-5-hydroxypyridine; and 5-chloro-2-methoxypyridin-3-ol.

From Matrix Scientific, P.O. Box 25067, Columbia, S.C. 29224-5067, USA: 4-bromo-3-methylphenol; 3-hydroxythiophenol; 3-bromo-5-fluorophenol; 2-bromo-4-methylphenol; 2-hydroxythioanisole; 3,4-difluorophenol; 3,4,5-trifluorophenol; 4-chloro-3-fluorophenol; 4-bromo-2-methylphenol; 2-fluoro-6-methoxyphenol; 2-fluoro-3-(trifluoromethyl)phenol; 2,6-diethylphenol; 2-[(dimethylamino)methyl]-4-ethylbenzenol; 3,5-diisopropylphenol; and 4-chloro-3-hydroxypyridine; 5-methoxypyridin-3-ol; 5-hydroxy-2-methoxypyridine; 5-iodopyridin-3-ol; 4-methoxypyridin-3-ol; 4-methyl-6-trifluoromethyl-pyridin-3-ol; 5,6-dimethoxypyridin-3-ol; and 2-methoxy-5-methylpyridin-3-ol.

From Oakwood Products, Inc., 1741 Old Dunbar Road, West Columbia, S.C. 29172, USA: 2-chloro-4-fluorophenol; 3,5-difluorophenol; 3-chloro-4-fluorophenol; 4-(methylsulfonyl)phenol; 2-fluoro-5-methylphenol; 2,6-difluorophenol; 4-(methylthio)phenol; 4-(trifluoromethoxy)phenol;

3-chloro-5-fluorophenol; 4-bromo-3-fluorophenol; 2-fluoro-5-(trifluoromethyl)phenol; 2-chloro-4-methoxyphenol; 5-fluoro-2-methoxyphenol; 2-(trifluoromethoxy)phenol; 2-chloro-6-fluoro-3-methylphenol; and 3-chloro-4-hydroxy-5-methoxybenzonitrile.

From TCI America, 9211 N. Harborgate Street, Portland, Oreg. 97203, USA: 2-hydroxybenzonitrile; 2,6-dichlorophenol; 3-cyanophenol; 3,4-dimethylphenol; 4-ethoxyphenol; 4-chloro-3-ethylphenol; 3-methyl-4-(methylthio)phenol; 2-chloro-6-fluorophenol; 2,3,5,6-tetrafluorophenol; 2,3-dimethylphenol; 2,3,6-trimethylphenol; 3,4-dichlorophenol; 6-tert-butyl-m-cresol; thymol; 4-tert-amylphenol; 2,3-difluorophenol; 2-bromo-4-fluorophenol; 4-isopropyl-3-methylphenol; 3-butoxyphenol; 2-tert-butyl-4-ethylphenol; 2-fluoro-4-methoxyphenol; 2,6-dichloro-4-methylphenol; and 5-hydroxy-2-methylpyridine; 5-chloro-3-pyridinol; 2-ethyl-3-hydroxy-6-methylpyridine; and 2-cyano-3-hydroxypyridine.

In addition, there are several procedures that are well known to one of average skill in the art of organic synthesis that can be used to prepare hydroxyaromatic compounds of formula ArOH. For example, an aryl ether of formula ArOMe may be treated with boron tribromide in dichloromethane at about −78° C. Examples of conditions that can be used for this reaction can be found in the literature, for example in Markworth, C. J. et al. WO2012004706 Page 67; in Cao, J. et al US 20120071516 Page 62; in Kelgtermans, H. et al. *Org. Lett.* 2012, 14, 1500-1503 Supporting Information Page S5; and in Neumeyer, J. L. et al. *J. Med. Chem.* 2012, 55, 3878-3890. Alternatively, an aryl ether of formula ArOMe may be heated with pyridine hydrochloride at a temperature between about 200° C. and about 250° C. to give the compound of formula ArOH. Examples of conditions that can be used for this reaction can be found in the literature, for example in Silver, G. C. and Trogler, W. C. *J. Am. Chem. Soc.* 1995, 117, 3983-3993; in Bisagni, E. et al. *Tetrahedron* 1980, 36, 1327-1330; in Hartmann, R. et al. WO 2012025638 Page 43; in Spadaro, A. et al. *J. Med. Chem.* 2012, 55, 2469-2473 Supporting Information Page S4. Alternatively, an aryl ether of formula ArOMe may be heated with hydrobromic acid in acetic acid at reflux to give the compound of formula ArOH. Examples of conditions that can be used for this reaction can be found in the literature, for example in Bao, X. et al. *J. Med. Chem.* 2012, 55, 2406-2415; in Wang, H. et al. US 20110288133 Page 10; and in Glossop, P. A. et al. US 20100303758 Page 41. Alternatively, an aryl ether of formula ArOMe may be heated with sodium thiomethoxide at a temperature between about 70° C. and about 140° C. in dimethylformamide to give the compound of formula ArOH. Examples of conditions that can be used for this reaction can be found in the literature, for example in Markworth, C. J. et al. WO 2012004706 Page 73; in Wempe, M. F. et al. *Nucleos. Nucleot. Nucl.* 2011, 30, 1312-1323; and in US 20110251173 Page 59.

The invention will now be illustrated with the following examples which have no limiting character.

EXAMPLES

Although certain exemplary embodiments are depicted and described herein, the compounds of the present invention can be prepared using appropriate starting materials according to the methods described generally herein and/or by methods available to one of ordinary skill in the art.

The following abbreviations are used in the experimental section
AcOH acetic acid
BBr$_3$ boron tribromide
Calcd. calculated
CH$_2$Cl$_2$ dichloromethane
CH$_3$CN acetonitrile
CH$_3$OH methanol
CHCl$_3$ chloroform
DMF dimethylformamide
DMSO dimethylsulfoxide
ESI electrospray ionization
Et$_2$O diethyl ether
EtOAc ethyl acetate
g grams
h hours
H$_2$O water
HCl hydrochloric acid
HF hydrogen fluoride
HRMS High-resolution mass spectrum
KF potassium fluoride
KHCO$_3$ potassium hydrogen carbonate
KOH potassium hydroxide
LRMS low-resolution mass spectrum
M molar
m/z mass divided by charge
M$^+$ positively charged molecular ion
MCPBA meta-chloroperoxybenzoic acid
MeOH methanol
mg milligrams
min minutes
mL milliliters
mmol millimoles
MnO$_2$ manganese dioxide
mp melting point
Na$_2$CO$_3$ sodium carbonate
Na$_2$SO$_3$ sodium thiosulfate
Na$_2$SO$_4$ sodium sulfate
NaH sodium hydride
NaHCO$_3$ sodium hydrogen carbonate
Na(OAc)$_3$BH sodium triacetoxyborohydride
NaOH sodium hydroxide
NH$_3$ ammonia
NH$_4$Cl ammonium chloride
NMR nuclear magnetic resonance
Rf retardation factor
THF tetrahydrofuran Preparation of Intermediate 1

3-(4-Hydroxy-phenyl)-isoxazole-5-carboxylic acid ethyl ester

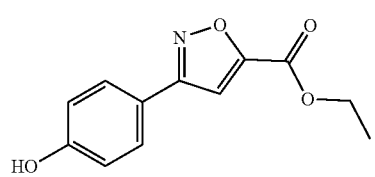 [SMILES: CCOC(=O)c1cc(-c2ccc(O)cc2)no1]

3-(4-Methoxy-phenyl)-isoxazole-5-carboxylic acid ethyl ester (available from ChemDiv Inc., 6605 Nancy Ridge Dr, San Diego, Calif., 92121, USA; 15 g, 60.1 mmol) was taken up in CH$_2$Cl$_2$ (30 mL) and 1 M BBr$_3$ (400 mL, 400 mmol) was added. The reaction mixture was stirred at room temperature overnight. The mixture was added to a beaker of ice-water and the solid was collected by filtration. The solid was taken up in EtOAc and the solution was washed with water to remove most of the undesired carboxylic acid side product. Yield: 1.9 g (14%).

Preparation of Intermediate 2

3-(4-Hydroxy-phenyl)-isoxazole-5-carboxylic acid amide

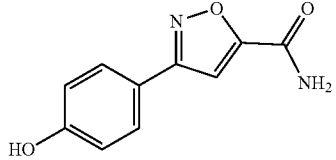 [SMILES: NC(=O)c1cc(-c2ccc(O)cc2)no1]

Crude 3-(4-hydroxy-phenyl)-isoxazole-5-carboxylic acid ethyl ester (which may be prepared as described in Preparation of Intermediate 1; 1.9 g, 8.15 mmol) was taken up in a solution of EtOH saturated with $NH_3$. The mixture was stirred overnight at room temperature under nitrogen. The solvent was evaporated to give 3-(4-hydroxy-phenyl)-isoxazole-5-carboxylic acid amide (1.17 g, 70%) as a flaky white powder.

Preparation of Intermediate 3

4-(3-Fluoro-benzyloxy)-benzaldehyde oxime

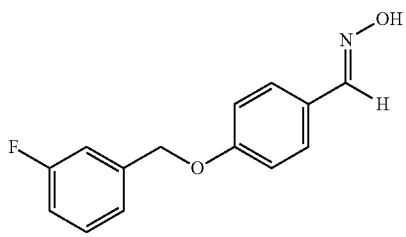 [SMILES: O/N=C/c1ccc(OCc2cccc(F)c2)cc1]

4-(3-Fluoro-benzyloxy)-benzaldehyde (which may be prepared as described in Brabanti, E. et al. WO 2007147491 or may be purchased from Matrix Scientific, Columbia, S.C. 29224-5067; 24 g, 78.2 mmol) was taken up in 9:1 EtOH/$H_2O$ (200 mL) and hydroxylamine hydrochloride (8.15 g, 117.3 mmol) was added. A solution of NaOH (7.51 g, 187.6 mmol) in 9:1 EtOH/$H_2O$ was added dropwise by addition funnel over 30 min. The mixture was heated at reflux for 4 h, then allowed to cool and acidified to pH 5 by adding glacial AcOH (17 mL). The solid was filtered off and dissolved in EtOAc. The organic solution was dried over $Na_2SO_4$, filtered, and evaporated to give 4-(3-fluoro-benzyloxy)-benzaldehyde oxime (6.6 g, 25%).

Preparation of Intermediate 4

3-[4-(3-Fluoro-benzyloxy)-phenyl]-isoxazole-5-carboxylic acid ethyl ester

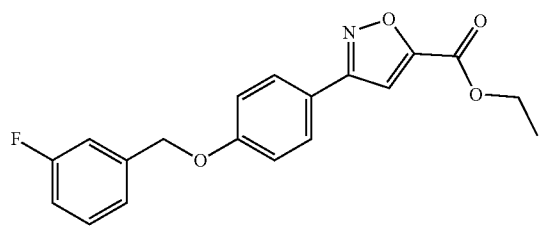 [SMILES: CCOC(=O)c1cc(-c2ccc(OCc3cccc(F)c3)cc2)no1]

4-(3-Fluoro-benzyloxy)-benzaldehyde oxime (which may be prepared as described in Preparation of Intermediate 3; 2 g, 8.2 mmol) was dissolved in DMF (4.8 mL) and the solution was cooled to 0° C. in an ice-water bath. N-Chlorosuccinimide (1.09 g, 8.2 mmol) was added slowly. The reaction mixture was stirred at 0° C. for 30 min, allowed to warm to room temperature and stirred at room temperature for 1 h. The reaction mixture was poured into ice-water (125 mL) and the resulting suspension was extracted with EtOAc (200 mL). The organic extract was dried over $Na_2SO_4$, filtered, and evaporated. The residue was dissolved in $Et_2O$ (20 mL). A mixture of ethyl propiolate (1.1 mL, 10.9 mmol) and triethylamine (1.5 mL) in $Et_2O$ (20 mL) was added dropwise, and the mixture was stirred at room temperature for 9 days. Silica gel was added and the solvent was evaporated. The resulting mixture was purified by chromatography (5-15% EtOAc/hexane) to give 3-[4-(3-fluoro-benzyloxy)-phenyl]-isoxazole-5-carboxylic acid ethyl ester (160 mg, 6%) as a white crystalline solid, which contained some of the undesired 4-carboxylic acid ethyl ester regioisomer.

Preparation of Intermediate 5

3-[4-(3-Fluoro-benzyloxy)-phenyl]-isoxazole-5-carboxylic acid

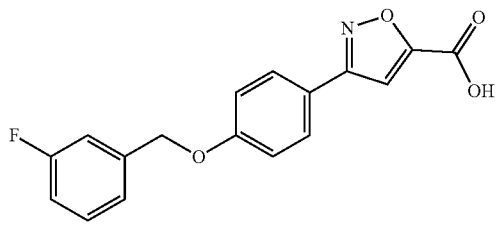 [SMILES: O=C(O)c1cc(-c2ccc(OCc3cccc(F)c3)cc2)no1]

3-[4-(3-Fluoro-benzyloxy)-phenyl]-isoxazole-5-carboxylic acid ethyl ester (which may be prepared as described in Preparation of Intermediate 4; 500 mg, 1.47 mmol) was dissolved in THF (5 mL), and 0.5 M aqueous KOH (12 mL, 1 mmol) was added. The reaction mixture was heated at reflux, cooled to room temperature, and then to 0° C. The mixture was acidified by the addition of 4 M aqueous HCl (10 mL). The resulting solid was filtered off and washed with cold $H_2O$ to give 3-[4-(3-fluoro-benzyloxy)-phenyl]-isoxazole-5-carboxylic acid (431 mg, 94%). HRMS Calcd. for $C_{17}H_{13}FNO_4$ $(M+H)^+$, 314.0823. Found: 314.0823.

Preparation of Intermediate 6

5-(2-Chloro-benzyloxy)-2-methyl-pyridine

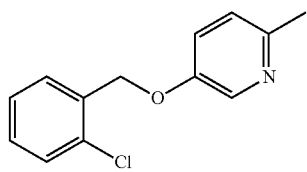 [SMILES: Cc1ccc(OCc2ccccc2Cl)cn1]

5-Hydroxy-2-methylpyridine (available from Aldrich Chemical Company, Inc., 1001 West Saint Paul Avenue, Milwaukee, Wis. 53233, USA; 5.00 g, 45.8 mmol) was dissolved in DMF (90 mL) and $K_2CO_3$ (6.9 g, 50 mmol) and tetrabutylammonium iodide (2 g, 5.4 mmol) were added. 2-Chlorobenzyl chloride (6.4 mL, 50.6 mmol) was added and the mixture was stirred at room temperature for 20 h. The reaction mixture was partitioned between EtOAc (300 mL) and H₂O (300 mL). The organic layer was dried (Na₂SO₄), filtered, evaporated, and purified by chromatography (30% EtOAc/hexane) to give 5-(2-chloro-benzyloxy)-2-methyl-pyridine (7.00 g, 66%) as a yellow oil.

Preparation of Intermediate 7

5-(2-Chloro-benzyloxy)-pyridine-2-carbaldehyde

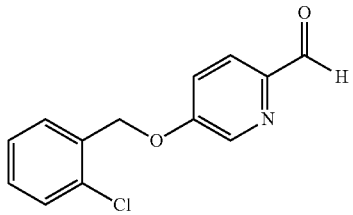 [SMILES: O=Cc1ccc(OCc2ccccc2Cl)cn1]

5-(2-Chloro-benzyloxy)-2-methyl-pyridine (which may be prepared as described in Preparation of Intermediate 6; 7.00 g, 30 mmol) was dissolved in CHCl₃ (200 mL) and the solution was cooled to 0° C. in an ice-water bath. MCPBA (6.21 g, 36 mmol) was added in 3 portions over 2 min. The reaction mixture was stirred in the ice-water bath for 1 h and then combined with 5% aqueous Na₂CO₃. The organic layer was dried (Na₂SO₄), filtered, and evaporated to give a yellow solid. Acetic anhydride (90 mL) was added and the mixture was heated at 130° C. for 30 min. The reaction mixture was allowed to cool to about 100° C. and then poured into ice-water and allowed to stand overnight. The mixture was extracted with EtOAc. The organic layer was dried (Na₂SO₄), filtered, evaporated, and purified by chromatography (25% EtOAc/hexane) to give a yellow oil. The oil was dissolved in EtOH (70 mL) and NaOH (2 g, 50 mmol) and H₂O (18 mL) were added. The mixture was heated at reflux for 1.5 h, then cooled to room temperature and concentrated under reduced pressure. The residue was partitioned between EtOAc and H₂O. The organic layer was dried (Na₂SO₄), filtered, evaporated, and purified by chromatography (25% EtOAc/hexane) to give a yellow oil (2.06 g). One half of the oil was dissolved in CHCl₃ (100 mL) and MnO₂ (11.25 g, 129 mmol) was added and the mixture was heated at reflux for 5 min. The reaction mixture was cooled to room temperature and filtered through celite. The celite was washed with CHCl₃ (50 mL). The combined filtrates were evaporated and purified by chromatography (25% EtOAc/hexanes) to give 5-(2-chloro-benzyloxy)-pyridine-2-carbaldehyde (2.06 g, 56%) as an off-white solid.

Preparation of Intermediate 8

5-(2-Chloro-benzyloxy)-pyridine-2-carbaldehyde oxime

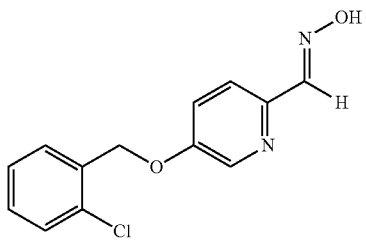 [SMILES: O/N=C/c1ccc(OCc2ccccc2Cl)cn1]

5-(2-Chloro-benzyloxy)-pyridine-2-carbaldehyde (which may be prepared as described in Preparation of Intermediate 7; 2.06 g, 8.3 mmol) was suspended in 9:1 EtOH/H₂O (20 mL) and hydroxylamine hydrochloride (1.45 g, 20.9 mmol) was added. A solution of 3.25 M NaOH in 9:1 EtOH/H₂O (6.5 mL, 21.1 mmol) was added slowly dropwise. The mixture was heated under reflux for 2.5 h and then cooled to 0° C. The pH was adjusted to 4 by the addition of glacial AcOH. The precipitate was filtered off to give 5-(2-chloro-benzyloxy)-pyridine-2-carbaldehyde oxime (1.5 g, 69%) as an off-white solid.

Preparation of Intermediate 9

3-[5-(2-Chloro-benzyloxy)-pyridin-2-yl]-isoxazole-5-carboxylic acid ethyl ester

5-(2-Chloro-benzyloxy)-pyridine-2-carbaldehyde oxime (which may be prepared as described in Preparation of Intermediate 8; 1.5 g, 5.7 mmol) was taken up in DMF (20 mL). The mixture was cooled to 0° C. and N-chlorosuccinimide (915 mg, 6.85 mmol) was added in portions. The reaction mixture was stirred for 3 h. The resulting solution was added to a separatory funnel containing ice-water and Et₂O. The organic layer was concentrated to give a white powder, which was stored under nitrogen in a freezer overnight. The white solid was taken up in 50% aqueous tert-butanol (20 mL) in a flask that was open to the air. Ethyl propiolate (0.7 mL, 6.85 mmol) was added, followed by 1 M sodium ascorbate (0.57 mL, 0.57 mmol) and 0.1 M copper(II) sulfate (5.7 mL, 0.57 mmol). NaHCO₃ (1.92 g, 22.8 mmol) was added in portions and the reaction mixture was stirred at room temperature for 3 h. The solid was filtered off to give a mixture of products favoring the desired regioisomer, 3-[5-(2-chloro-benzyloxy)-pyridin-2-yl]-isoxazole-5-carboxylic acid ethyl ester (328 mg, 16%).

Preparation of Intermediate 10

3-[5-(2-Chloro-benzyloxy)-pyridin-2-yl]-isoxazole-5-carboxylic acid

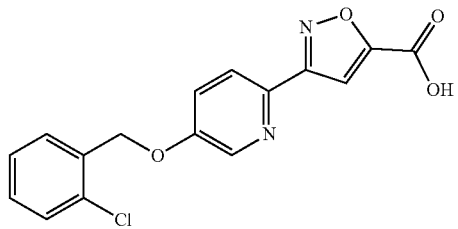 [SMILES: O=C(O)c1cc(-c2ccc(OCc3ccccc3Cl)cn2)no1]

Crude 3-[5-(2-Chloro-benzyloxy)-pyridin-2-yl]-isoxazole-5-carboxylic acid ethyl ester (which may be prepared as described in Preparation of Intermediate 9; 236 mg, 0.66 mmol assumed) was taken up in a mixture of 2 M KOH (12 mL) and THF (3 mL). The mixture was heated at 55° C. for 4 h and then stirred at room temperature overnight. The mixture was cooled to 0° C. and 4 M aqueous HCl (3 mL) was added. The mixture was extracted with EtOAc and the organic layer was dried ($Na_2SO_4$), filtered, and evaporated to give 3-[5-(2-chloro-benzyloxy)-pyridin-2-yl]-isoxazole-5-carboxylic acid (220 mg, 100%) as an off-white powder.

Preparation of Intermediate 11

3-[4-(2-Chloro-pyridin-3-ylmethoxy)-phenyl]-isoxazole-5-carboxylic acid ethyl ester

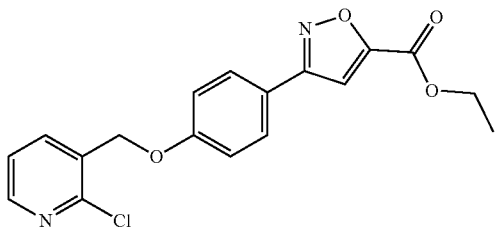 [SMILES: CCOC(=O)c1cc(-c2ccc(OCc3cccnc3Cl)cc2)no1]

3-(4-Hydroxy-phenyl)-isoxazole-5-carboxylic acid ethyl ester (which may be prepared as described in Preparation of Intermediate 1) and 3-bromomethyl-2-chloro-pyridine (which may be prepared as described in Selby, T. P. and Winters, M. P. U.S. Pat. No. 5,739,326 Column 19) were reacted using conditions similar to those described for Preparation of Intermediate 24 to give 3-[4-(2-chloro-pyridin-3-ylmethoxy)-phenyl]-isoxazole-5-carboxylic acid ethyl ester.

Preparation of Intermediate 12

3-[4-(tert-Butyl-dimethyl-silanyloxy)-phenyl]-isoxazole-5-carboxylic acid ethyl ester

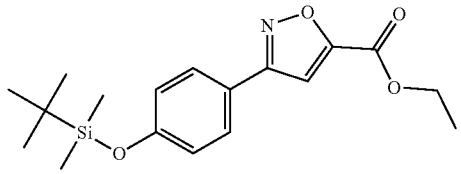 [SMILES: CCOC(=O)c1cc(-c2ccc(O[Si](C)(C)C(C)(C)C)cc2)no1]

4-(tert-Butyl-dimethyl-silanyloxy)-benzaldehyde oxime (which may be prepared according to the procedure described in Kao, Y. T. R. et al. US 20110212975 page 17; ~20 g, ~80 mmol) was dissolved in DMF (50 mL) and the solution was cooled to 0° C. N-Chlorosuccinimide (12.8 g, 96 mmol) was added in portions. The reaction mixture was stirred at 0° C. for 30 min, allowed to warm to room temperature and stirred at room temperature for 1.5 h. The reaction mixture was poured into ice-water (100 mL) and the resulting suspension was extracted with EtOAc (100 mL). The organic extract was dried over $Na_2SO_4$, filtered, and evaporated. $Et_2O$ (120 mL) was added to the residue, and then a solution of ethyl propiolate (16 mL, 158 mmol) and triethylamine (12 mL) in $Et_2O$ (120 mL) was added dropwise. The mixture was stirred at room temperature for 48 h. The reaction mixture was filtered and the filtrate was evaporated to give a brown oil which was purified by filtration through a silica gel plug (eluting with 12% EtOAc/hexanes) followed by silica gel chromatography. Final purification was accomplished using preparatory supercritical fluid chromatography (100 bar $CO_2$ modified with 10% MeOH, flow rate of 2 mL/min at 30° C.) to give 3-[4-(tert-butyl-dimethyl-silanyloxy)-phenyl]-isoxazole-5-carboxylic acid ethyl ester (600 mg, 2%).

Preparation of Intermediate 13

3-[4-(tert-Butyl-dimethyl-silanyloxy)-phenyl]-isoxazole-5-carboxylic acid amide

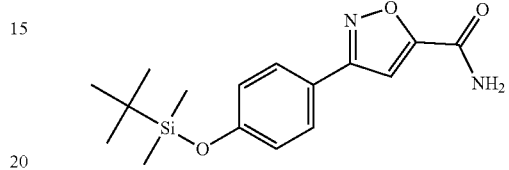

3-[4-(tert-butyl-dimethyl-silanyloxy)-phenyl]-isoxazole-5-carboxylic acid ethyl ester (which may be prepared as described in Preparation of Intermediate 12; 500 mg, 1.4 mmol) was dissolved in a saturated solution of $NH_3$ in EtOH (200 mL). The mixture was stirred at room temperature for 60 h. The solvent was evaporated and the residue was purified by chromatography (50-60% EtOAc/hexanes) to give 3-[4-(tert-butyl-dimethyl-silanyloxy)-phenyl]-isoxazole-5-carboxylic acid amide (160 mg, 35%) as a white solid.

Preparation of Intermediate 14

3-(4-Bromomethyl-phenyl)-isoxazole-5-carboxylic acid amide

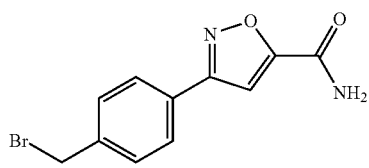 [SMILES: NC(=O)c1cc(-c2ccc(CBr)cc2)no1]

N-Chlorosuccinimide (624 mg, 4.7 mmol) was added in portions to a solution of 4-bromomethyl-benzaldehyde oxime (which may be prepared as described in Charrier, J.-D. et al. WO2011/143426 p 77; 1 g, 4.7 mmol) in DMF (9 mL) at room temperature. The reaction mixture was stirred for 2 h under argon. The mixture was poured into ice-water and this was extracted with $Et_2O$ (3×50 mL). The combined organic layers were washed with brine, dried ($Na_2SO_4$) and evaporated to give a solid (1.4 g). The solid was dissolved in 50% aqueous tert-butanol (20 mL) in a flask that was open to the air. Propiolamide (which may be prepared as described in Matsumoto, T. et al. U.S. Pat. No. 7,851,473 Column 128; 323 mg, 4.7 mmol) was added, followed by 1 M sodium ascorbate (0.47 mL, 0.47 mmol) and 0.1 M copper(II) sulfate (2.34 mL, 0.23 mmol). $KHCO_3$ (1.87 g, 18.7 mmol) was added in portions and the reaction mixture was stirred at room temperature for 3 h. $H_2O$ (25 mL) was added and the mixture was extracted with 85:15 $CHCl_3/CH_3OH$ (3×100 mL). The combined organic layers were washed with brine, dried ($Na_2SO_4$), filtered, evaporated, and purified by chromatography (16-20% acetone/$CH_2Cl_2$) to give 3-(4-bromomethyl-phenyl)-isoxazole-5-carboxylic acid amide (156 mg, 12%). Purification of mixed fractions by chromatography (16-20% acetone/$CH_2Cl_2$) provided a further 40 mg (3%) of 3-(4-bromomethyl-phenyl)-isoxazole-5-carboxylic acid amide.

Preparation of Intermediate 16

4-(tert-Butyl-dimethyl-silanyloxymethyl)-benzonitrile

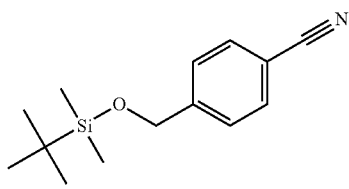 [SMILES: CC(C)(C)[Si](C)(C)OCc1ccc(C#N)cc1]

To a solution of 4-cyanobenzyl alcohol (5.0 g, 37.9 mmol) in DMF was added imidazole (2.79 g, 41 mmmol) and tert-butyldimethylsilyl chloride (6.2 g, 41 mmol). After stirring for 14 h, the reaction mixture was poured into 0.1M aqueous KHSO$_4$ and extracted three times with diethyl ether. The combined organic phases were washed twice with water, once with brine and dried over MgSO$_4$. Filtration followed by removal of volatiles under reduced pressure gave crude product. Flash chromatography (10% EtOAc in hexane) provided 4-(tert-butyl-dimethyl-silanyloxymethyl)-benzonitrile as a white solid (3.41 g, 36%). $^1$H NMR (300 MHz, CDCl$_3$) δ ppm 7.57 (d, 2H), 7.36 (d, 2H), 4.68 (d, 2H), 0.82 (s, 9H), 0.02 (2, 6H).

Preparation of Intermediate 17

4-(tert-Butyl-dimethyl-silanyloxymethyl)-benzaldehyde oxime

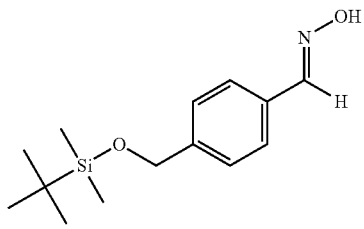 [SMILES: CC(C)(C)[Si](C)(C)OCc1ccc(/C=N/O)cc1]

To a solution of 4-(tert-butyl-dimethyl-silanyloxymethyl)-benzonitrile (which may be prepared as described in Preparation of Intermediate 16; 15.21 g, 61.5 mmol) in toluene (100 mL) at 0° C. under argon was added dropwise di-isobutyl-aluminum hydride (1.0 M in toluene, 15 mL, 15 mmol). The reaction mixture was warmed to room temperature and stirred for 2 h, after which it was cooled to 0° C. and charged with 100 mL of saturated aqueous Rochelle salt solution. The mixture was allowed to stir for 14 hours after which the mixture was extracted three times with EtOAc. The combined organic phases were washed with brine and dried over MgSO$_4$. Filtration followed by removal of volatiles under reduced pressure gave 4-(tert-butyl-dimethyl-silanyloxymethyl)-benzaldehyde which was used without further purification. To a solution of the aldehyde in ethanol was added hydroxylamine hydrochloride (4.66 g, 67 mmol) and pyridine (5.4 mL, 67 mmol). The reaction mixture was stirred until no starting material was observed by TLC and then all volatiles were removed under reduced pressure. The resulting product was suspended in water and the aqueous phase was extracted three times with diethyl ether. The combined organic phases were washed with brine and dried over MgSO$_4$. Filtration followed by removal of volatiles under reduced pressure gave 4-(tert-butyl-dimethyl-silanyloxymethyl)-benzaldehyde oxime (14.60 g, 90%) as a white solid. LRMS (ESI$^+$): m/z [M+H]$^+$ 266.1; $^1$H NMR (300 MHz, CDCl$_3$) δ ppm 11.12 (s, 1H), 8.05 (s, 1H), 7.50 (d, 2H), 7.24 (d, 1H), 4.64 (s, 2H), 0.82 (s, 9H), 0.03 (s, 6H).

Preparation of Intermediate 18

3-[4-(tert-Butyl-dimethyl-silanyloxymethyl)-phenyl]-isoxazole-5-carboxylic acid amide

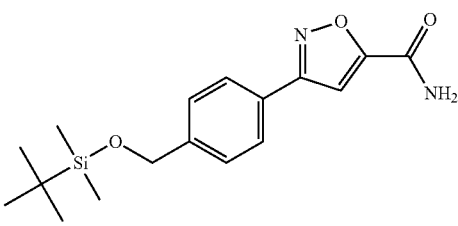 [SMILES: CC(C)(C)[Si](C)(C)OCc1ccc(-c2cc(C(N)=O)on2)cc1]

A solution of 4-(tert-butyl-dimethyl-silanyloxymethyl)-benzaldehyde oxime (which may be made as described in Preparation of Intermediate 17; 3 g, 11.3 mmol) in DMF (25 mL) was cooled to 0° C. and N-chlorosuccinimide (1.51 g, 11.3 mmol) was added in portions. The cooling bath was removed and the reaction mixture was stirred for 2.5 h. The mixture was poured into ice-water (75 mL) and this was extracted with Et$_2$O (3×100 mL). The combined organic layers were washed with brine, dried (Na$_2$SO$_4$) and evaporated to give a solid (3.5 g). The solid was dissolved in 50% aqueous tert-butanol (60 mL) in a flask that was open to the air. Propiolamide (which may be prepared as described in Matsumoto, T. et al. U.S. Pat. No. 7,851,473 Column 128; 0.7 mL, 6.85 mmol) was added, followed by 1 M sodium ascorbate (1.13 mL, 1.13 mmol) and 0.1 M copper(II) sulfate (5.65 mL, 0.565 mmol). KHCO$_3$ (4.52 g, 45.1 mmol) was added in portions and the reaction mixture was stirred at room temperature for 2.5 h. H$_2$O (100 mL) was added and a yellow solid was filtered off and dried under high vacuum overnight (3 g). This material was taken up in CH$_2$Cl$_2$/acetone and filtered. The filtrate was evaporated and the residue was purified by chromatography (9-20% acetone/CH$_2$Cl$_2$) to give 3-[4-(tert-butyl-dimethyl-silanyloxymethyl)-phenyl]-isoxazole-5-carboxylic acid amide (800 mg, 21%). Purification of mixed fractions by chromatography (50-60% EtOAc/toluene) provided a further 450 mg (12%) of 3-[4-(tert-butyl-dimethyl-silanyloxymethyl)-phenyl]-isoxazole-5-carboxylic acid amide.

Preparation of Intermediate 19

3-(4-Hydroxymethyl-phenyl)-isoxazole-5-carboxylic acid amide

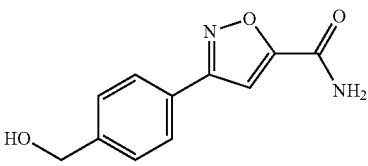 [SMILES: NC(=O)c1cc(-c2ccc(CO)cc2)no1]

A mixture of 3-[4-(tert-butyl-dimethyl-silanyloxymethyl)-phenyl]-isoxazole-5-carboxylic acid amide (which may be prepared as described in Preparation of Intermediate 18; 800 mg, 2.4 mmol) in THF (8 mL) and HF/pyridine (70%; 0.25 mL) was stirred at room temperature. After 30 min, an addition portion of THF (8 mL) was added and the mixture was stirred for 5 h. H$_2$O was added and the mixture was extracted four times with CHCl$_3$/CH$_3$OH (7:3). The organic layers were dried (Na$_2$SO$_4$), filtered and evaporated to give 3-(4-hydroxymethyl-phenyl)-isoxazole-5-carboxylic acid amide (300 mg, 57%).

Preparation of Intermediate 20

3-(4-Formyl-phenyl)-isoxazole-5-carboxylic acid amide

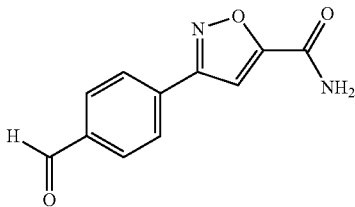 [SMILES: NC(=O)c1cc(-c2ccc(C=O)cc2)no1]

To a solution of 3-(4-hydroxymethyl-phenyl)-isoxazole-5-carboxylic acid amide (which may be prepared as described in Preparation of Intermediate 19; 100 mg, 0.46 mmol) in DMSO (1.5 mL) was added Dess-Martin periodinane (214 mg, 0.5 mmol). The mixture was stirred at room temperature for 2.5 h. Water (5 mL) was added and the mixture was filtered to give a white solid. The filtrate was extracted three times with EtOAc and the combined extracts were dried (Na$_2$SO$_4$), filtered and evaporated to give a residue. The white solid from the first filtration was triturated with MeOH and the mixture was filtered. The filtrate was evaporated to give a second residue. The two residues were combined and purified by chromatography (25% acetone/CH$_2$Cl$_2$) to give 3-(4-formyl-phenyl)-isoxazole-5-carboxylic acid amide (50 mg, 50%).

Preparation of Intermediate 21

4-(2-Trifluoromethyl-benzyloxy)-benzaldehyde oxime

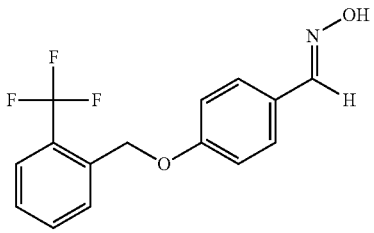 [SMILES: O/N=C/c1ccc(OCc2ccccc2C(F)(F)F)cc1]

4-(2-Trifluoromethyl-benzyloxy)-benzaldehyde (which may be prepared as described in Panetta, J. A. et al. U.S. Pat. No. 6,251,928 Column 25; 28.8 g, 102.7 mmol) was combined with 9:1 EtOH/H$_2$O (210 mL) and hydroxylamine hydrochloride (11 g, 158 mmol) was added. A solution of 3.15 M NaOH in 9:1 EtOH/H$_2$O (70 mL, 221 mmol) was added dropwise. The mixture was stirred at room temperature for 2 h and then heated at 50° C. for 1 h. The mixture was partitioned between EtOAc and H$_2$O, and the organic layer was dried, filtered, and evaporated to give 4-(2-trifluoromethyl-benzyloxy)-benzaldehyde oxime (14 g, 46%).

Example 1

3-[4-(2-Trifluoromethylsulfanyl-benzyloxy)-phenyl]-isoxazole-5-carboxylic acid amide

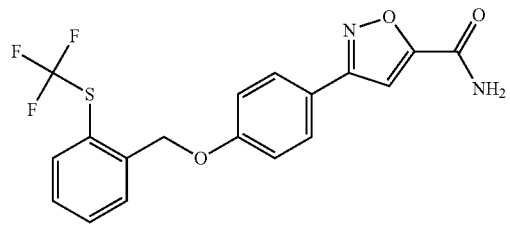 [SMILES: NC(=O)c1cc(-c2ccc(OCc3ccccc3SC(F)(F)F)cc2)no1]

3-(4-Hydroxy-phenyl)-isoxazole-5-carboxylic acid amide (which may be prepared as described in Preparation of Intermediate 2; 60 mg, 0.30 mmol) was dissolved in THF (1.5 mL). K$_2$CO$_3$ (41 mg, 0.30 mmol) and tetrabutylammonium iodide (15 mg, 0.04 mmol) were added. 2-(Trifluoromethylthio)benzyl bromide (available from Oakwood Products, Inc., 1741 Old Dunbar Road, West Columbia, S.C. 29172, USA; 88 µL, 0.30 mmol) was added and the reaction mixture was stirred at room temperature for 1.5 h. DMF (100 µL) was added and the mixture was heated at 45° C. for 4 h. The reaction mixture was cooled to room temperature and partitioned between EtOAc (5 mL) and H$_2$O (5 mL). The organic layer was evaporated and the residue was purified by chromatography (35-50% EtOAc/hexanes) to give 3-[4-(2-trifluoromethylsulfanyl-benzyloxy)-phenyl]-isoxazole-5-carboxylic acid amide (60 mg, 52%) as a white solid. HRMS Calcd. for C$_{18}$H$_{14}$F$_3$N$_2$O$_3$S (M+H)$^+$, 395.0672. Found: 395.0688.

Example 2

3-[4-(2-Trifluoromethanesulfinyl-benzyloxy)-phenyl]-isoxazole-5-carboxylic acid amide

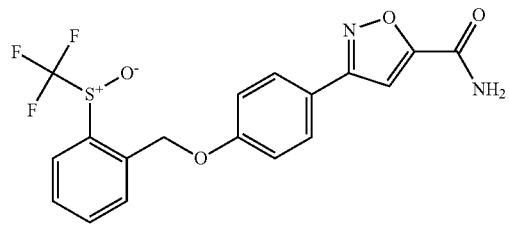 [SMILES: NC(=O)c1cc(-c2ccc(OCc3ccccc3[S+]([O-])C(F)(F)F)cc2)no1]

A suspension of 3-[4-(2-trifluoromethylsulfanyl-benzyloxy)-phenyl]-isoxazole-5-carboxylic acid amide (which may be prepared as described in Example 1; 60 mg, 0.153 mmol) in CH$_2$Cl$_2$ (8 mL) was cooled to 0° C. in an ice-water bath. MCPBA (130 mg, 5 equivalents) was added and the mixture was stirred at 0° C. for 1 h and then at room temperature overnight. The reaction mixture was washed with 10% aqueous Na$_2$SO$_3$ and saturated aqueous NaHCO$_3$, dried (Na$_2$SO$_4$), filtered, evaporated and purified by chromatography (35-45% EtOAc/hexanes) to give 3-[4-(2-trifluoromethanesulfinyl-benzyloxy)-phenyl]-isoxazole-5-carboxylic acid amide (16.2 mg, 26%) as a white solid. HRMS Calcd. for $C_{18}H_{14}F_3N_2O_4S$ (M+H)$^+$, 411.0621. Found: 411.0617.

Example 3

3-[4-(2-Methoxy-benzyloxy)-phenyl]-isoxazole-5-carboxylic acid amide

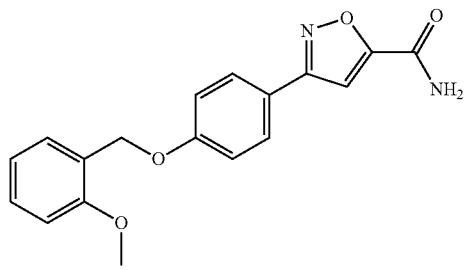 [SMILES: COc1ccccc1COc1ccc(-c2cc(C(N)=O)on2)cc1]

3-(4-Hydroxy-phenyl)-isoxazole-5-carboxylic acid amide (which may be prepared as described in Preparation of Intermediate 2; 50 mg, 0.24 mmol), $K_2CO_3$ (37 mg, 0.27 mmol) and tetrabutylammonium iodide (9 mg, 0.024 mmol) were taken up in DMF (2.4 mL). 2-Methoxybenzyl chloride (42 mg, 0.27 mmol) was added and the reaction mixture was stirred at room temperature overnight. The solvent was evaporated and the residue was purified by high-throughput purification to give 3-[4-(2-methoxy-benzyloxy)-phenyl]-isoxazole-5-carboxylic acid amide (10.5 mg, 13%). LRMS (ESI$^+$): m/z [M+H]$^+$ 325.0.

Example 4

3-[4-(3,4-Dimethyl-benzyloxy)-phenyl]-isoxazole-5-carboxylic acid amide

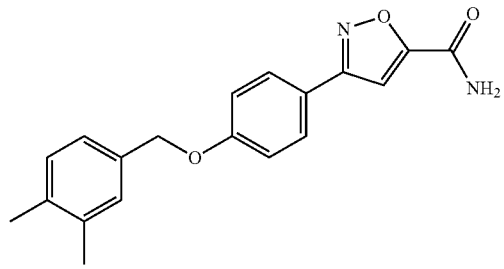 [SMILES: Cc1ccc(COc2ccc(-c3cc(C(N)=O)on3)cc2)cc1C]

3-(4-Hydroxy-phenyl)-isoxazole-5-carboxylic acid amide (which may be prepared as described in Preparation of Intermediate 2; 50 mg, 0.24 mmol), $K_2CO_3$ (37 mg, 0.27 mmol) and tetrabutylammonium iodide (9 mg, 0.024 mmol) were taken up in DMF (2.4 mL). 3,4-Dimethylbenzyl bromide (77 mg, 0.27 mmol) was added and the reaction mixture was stirred at room temperature overnight. The solvent was evaporated and the residue was purified by high-throughput purification to give 3-[4-(3,4-dimethyl-benzyloxy)-phenyl]-isoxazole-5-carboxylic acid amide (8.7 mg, 11%). LRMS (ESI$^+$): m/z [M+H+CH$_3$CN]$^+$ 364.2.

Example 5

3-[4-(2-Cyano-benzyloxy)-phenyl]-isoxazole-5-carboxylic acid amide

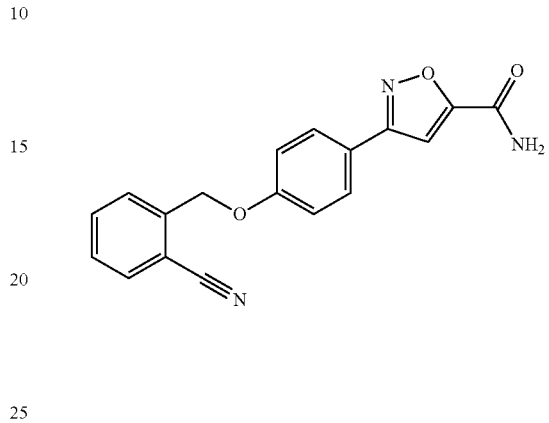

3-(4-Hydroxy-phenyl)-isoxazole-5-carboxylic acid amide (which may be prepared as described in Preparation of Intermediate 2; 50 mg, 0.24 mmol), $K_2CO_3$ (37 mg, 0.27 mmol) and tetrabutylammonium iodide (9 mg, 0.024 mmol) were taken up in DMF (2.4 mL). 2-Cyanobenzyl bromide (53 mg, 0.27 mmol) was added and the reaction mixture was stirred at room temperature overnight. The solvent was evaporated and the residue was purified by high-throughput purification to give 3-[4-(2-cyano-benzyloxy)-phenyl]-isoxazole-5-carboxylic acid amide (20.7 mg, 27%). LRMS (ESI$^+$): m/z [M+CH$_3$CN+H]$^+$ 361.1.

Example 6

3-[4-(2,6-Dichloro-benzyloxy)-phenyl]-isoxazole-5-carboxylic acid amide

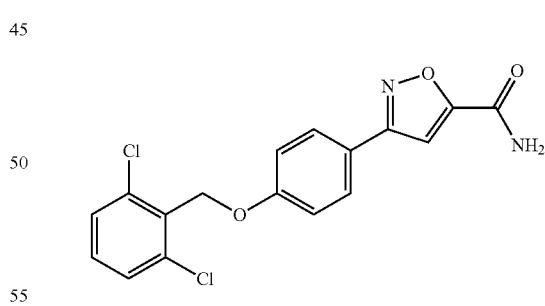

3-(4-Hydroxy-phenyl)-isoxazole-5-carboxylic acid amide (which may be prepared as described in Preparation of Intermediate 2; 50 mg, 0.24 mmol), $K_2CO_3$ (37 mg, 0.27 mmol) and tetrabutylammonium iodide (9 mg, 0.024 mmol) were taken up in DMF (2.4 mL). 2,6-Dichlorobenzyl bromide (65 mg, 0.27 mmol) was added and the reaction mixture was stirred at room temperature overnight. The solvent was evaporated and the residue was purified by high-throughput purification to give 3-[4-(2,6-dichloro-benzyloxy)-phenyl]- isoxazole-5-carboxylic acid amide (8.2 mg, 9%). LRMS (ESI⁺): m/z [M+CH₃CN+H]⁺ 404.0.

Example 7

3-[4-(3,4-Difluoro-benzyloxy)-phenyl]-isoxazole-5-carboxylic acid amide

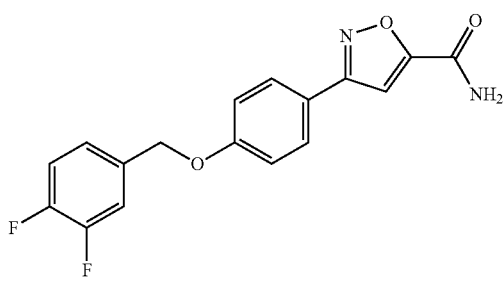 [SMILES: NC(=O)c1cc(-c2ccc(OCc3ccc(F)c(F)c3)cc2)no1]

3-(4-Hydroxy-phenyl)-isoxazole-5-carboxylic acid amide (which may be prepared as described in Preparation of Intermediate 2; 50 mg, 0.24 mmol), K₂CO₃ (37 mg, 0.27 mmol) and tetrabutylammonium iodide (9 mg, 0.024 mmol) were taken up in DMF (2.4 mL). 3,4-Difluorobenzyl bromide (56 mg, 0.27 mmol) was added and the reaction mixture was stirred at room temperature overnight. The solvent was evaporated and the residue was purified by high-throughput purification to give 3-[4-(3,4-difluoro-benzyloxy)-phenyl]-isoxazole-5-carboxylic acid amide (14 mg, 18%). HRMS Calcd. for C₁₇H₁₃F₂N₂O (M+H)⁺, 331.0889. Found: 331.0886.

Example 8

3-[4-(2-Fluoro-benzyloxy)-phenyl]-isoxazole-5-carboxylic acid amide

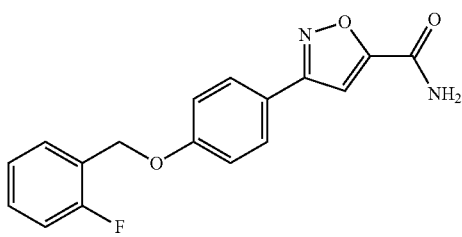 [SMILES: NC(=O)c1cc(-c2ccc(OCc3ccccc3F)cc2)no1]

3-(4-Hydroxy-phenyl)-isoxazole-5-carboxylic acid amide (which may be prepared as described in Preparation of Intermediate 2; 50 mg, 0.24 mmol), K₂CO₃ (37 mg, 0.27 mmol) and tetrabutylammonium iodide (9 mg, 0.024 mmol) were taken up in DMF (2.4 mL). 2-Fluorobenzyl bromide (51 mg, 0.27 mmol) was added and the reaction mixture was stirred at room temperature overnight. The solvent was evaporated and the residue was purified by high-throughput purification to give 3-[4-(2-fluoro-benzyloxy)-phenyl]-isoxazole-5-carboxylic acid amide (7.6 mg, 10%). LRMS (ESI⁺): m/z [2M+H]⁺ 625.1.

Example 9

3-[4-(2-Methyl-benzyloxy)-phenyl]-isoxazole-5-carboxylic acid amide

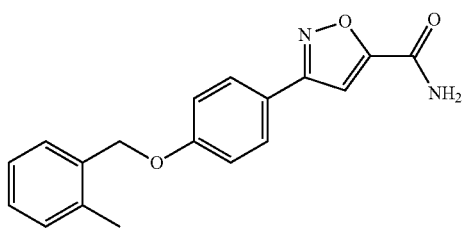 [SMILES: Cc1ccccc1COc1ccc(-c2cc(C(N)=O)on2)cc1]

3-(4-Hydroxy-phenyl)-isoxazole-5-carboxylic acid amide (which may be prepared as described in Preparation of Intermediate 2; 50 mg, 0.24 mmol), K₂CO₃ (37 mg, 0.27 mmol) and tetrabutylammonium iodide (9 mg, 0.024 mmol) were taken up in DMF (2.4 mL). 2-Methylbenzyl bromide (38 mg, 0.27 mmol) was added and the reaction mixture was stirred at room temperature overnight. The solvent was evaporated and the residue was purified by high-throughput purification to give 3-[4-(2-methyl-benzyloxy)-phenyl]-isoxazole-5-carboxylic acid amide (20.9 mg, 28%). HRMS Calcd. for C₁₈H₁₇N₂O₃ (M+H)⁺, 309.1234. Found: 309.1233.

Example 10

3-[4-(2-Trifluoromethoxy-benzyloxy)-phenyl]-isoxazole-5-carboxylic acid amide

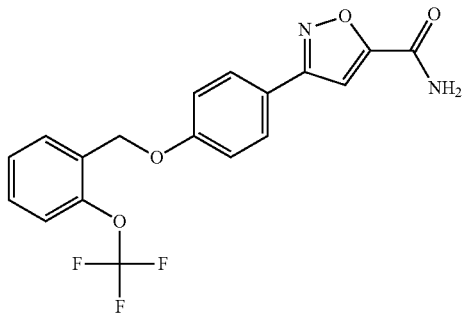 [SMILES: NC(=O)c1cc(-c2ccc(OCc3ccccc3OC(F)(F)F)cc2)no1]

3-(4-Hydroxy-phenyl)-isoxazole-5-carboxylic acid amide (which may be prepared as described in Preparation of Intermediate 2; 50 mg, 0.24 mmol), K₂CO₃ (37 mg, 0.27 mmol) and tetrabutylammonium iodide (9 mg, 0.024 mmol) were taken up in DMF (2.4 mL). 2-(Trifluoromethoxy)benzyl bromide (38 mg, 0.27 mmol) was added and the reaction mixture was stirred at room temperature overnight. The solvent was evaporated and the residue was purified by high-throughput purification to give 3-[4-(2-trifluoromethoxy-benzyloxy)- phenyl]-isoxazole-5-carboxylic acid amide (1.2 mg, 1.3%). HRMS Calcd. for $C_{18}H_{14}F_3N_2O_4$ (M+H)$^+$, 379.0900. Found: 379.0987.

Example 11

3-[4-(2-Iodo-benzyloxy)-phenyl]-isoxazole-5-carboxylic acid amide

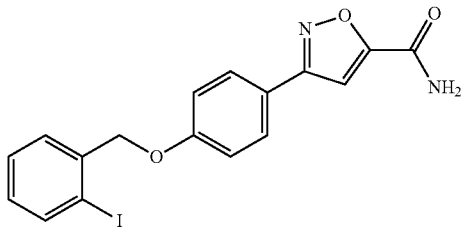 [SMILES: NC(=O)c1cc(-c2ccc(OCc3ccccc3I)cc2)no1]

3-(4-Hydroxy-phenyl)-isoxazole-5-carboxylic acid amide (which may be prepared as described in Preparation of Intermediate 2; 50 mg, 0.24 mmol), $K_2CO_3$ (37 mg, 0.27 mmol) and tetrabutylammonium iodide (9 mg, 0.024 mmol) were taken up in DMF (2.4 mL). 2-Iodobenzyl chloride (61 mg, 0.24 mmol) was added and the reaction mixture was stirred at room temperature overnight. The solvent was evaporated and the residue was purified by high-throughput purification to give 3-[4-(2-iodo-benzyloxy)-phenyl]-isoxazole-5-carboxylic acid amide (1.4 mg, 1.3%). HRMS Calcd. for $C_{17}H_{14}IN_2O_3$ (M+H)$^+$, 421.0044. Found: 421.0040.

Example 12

3-[4-(2-Chloro-6-fluoro-benzyloxy)-phenyl]-isoxazole-5-carboxylic acid amide

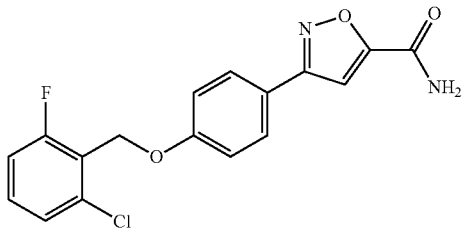 [SMILES: NC(=O)c1cc(-c2ccc(OCc3c(F)cccc3Cl)cc2)no1]

3-(4-Hydroxy-phenyl)-isoxazole-5-carboxylic acid amide (which may be prepared as described in Preparation of Intermediate 2; 50 mg, 0.24 mmol), $K_2CO_3$ (37 mg, 0.27 mmol) and tetrabutylammonium iodide (9 mg, 0.024 mmol) were taken up in DMF (2.4 mL). 2-Chloro-6-fluorobenzyl chloride (45 mg, 0.24 mmol) was added and the reaction mixture was stirred at room temperature overnight. The solvent was evaporated and the residue was purified by high-throughput purification to give 3-[4-(2-chloro-6-fluoro-benzyloxy)-phenyl]-isoxazole-5-carboxylic acid amide (12.3 mg, 15%). HRMS Calcd. for $C_{17}H_{13}ClFN_2O_3$ (M+H)$^+$, 347.0593. Found: 347.0591.

Example 13

3-[4-(2-Chloro-5-fluoro-benzyloxy)-phenyl]-isoxazole-5-carboxylic acid amide

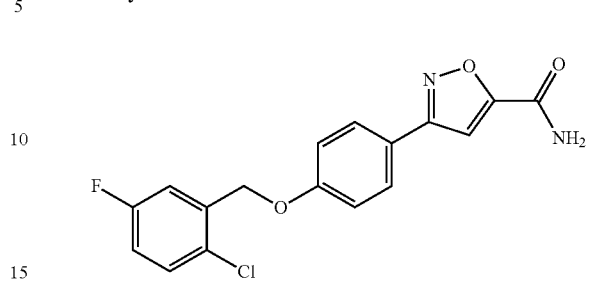

3-(4-Hydroxy-phenyl)-isoxazole-5-carboxylic acid amide (which may be prepared as described in Preparation of Intermediate 2; 50 mg, 0.24 mmol), $K_2CO_3$ (37 mg, 0.27 mmol) and tetrabutylammonium iodide (9 mg, 0.024 mmol) were taken up in DMF (2.4 mL). 2-Chloro-5-fluorobenzyl chloride (55 mg, 0.24 mmol) was added and the reaction mixture was stirred at room temperature overnight. The solvent was evaporated and the residue was purified by high-throughput purification to give 3-[4-(2-chloro-5-fluoro-benzyloxy)-phenyl]-isoxazole-5-carboxylic acid amide (3.8 mg, 4%). LRMS (ESI$^+$): m/z [M+CH$_3$CN+H]$^+$ 387.9.

Example 14

3-[5-(2-Chloro-benzyloxy)-pyridin-2-yl]-isoxazole-5-carboxylic acid amide

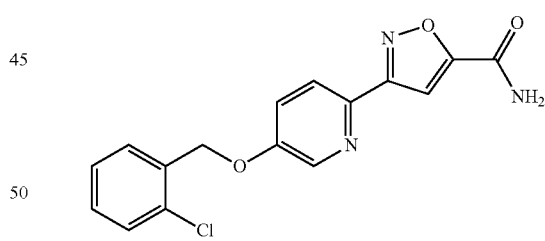

3-[5-(2-Chloro-benzyloxy)-pyridin-2-yl]-isoxazole-5-carboxylic acid (which may be prepared as described in Preparation of Intermediate 10; 220 mg, 0.67 mmol), NH$_4$Cl (71 mg, 1.33 mmol), N'-(3-dimethylaminopropyl)-N-ethyl-carbodiimide hydrochloride (258 mg, 1.33 mmol), and 1-hydroxybenzotriazole (183 mg, 1.33 mmol) were taken up in THF (8 mL). Diisopropylethylamine (235 µL, 1.33 mmol) was added and the mixture was stirred overnight under nitrogen. The solvent was evaporated and the residue was purified by flash chromatography on silica, eluting with 50% EtOAc/hexanes, to give 3-[5-(2-chloro-benzyloxy)-pyridin-2-yl]-

Example 15

3-[4-(2-Chloro-pyridin-3-ylmethoxy)-phenyl]-isoxazole-5-carboxylic acid amide

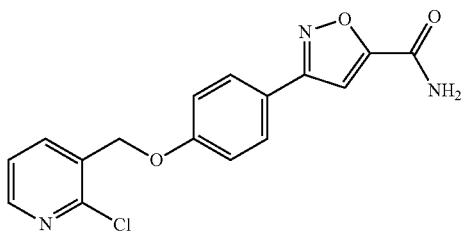 [SMILES: NC(=O)c1cc(-c2ccc(OCc3cccnc3Cl)cc2)no1]

3-[4-(2-Chloro-pyridin-3-ylmethoxy)-phenyl]-isoxazole-5-carboxylic acid ethyl ester (which may be prepared as described in Preparation of Intermediate 11; 57 mg, 0.16 mmol) was taken up in 2M $NH_3$ in EtOH. The mixture was stirred overnight, transferred to a 20 mL scintillation vial and evaporated after several hours at room temperature. The residue was purified twice by chromatography, eluting first with 35-80% EtOAc/hexanes and then with 50-90% EtOAc/hexanes to give 3-[4-(2-chloro-pyridin-3-ylmethoxy)-phenyl]-isoxazole-5-carboxylic acid amide (7.2 mg, 14%). HRMS Calcd. for $C_{16}H_{13}ClN_3O_3$ (M+H)$^+$, 330.0640. Found: 330.0637.

Example 16

3-[4-(3-Fluoro-benzyloxy)-phenyl]-isoxazole-5-carboxylic acid amide

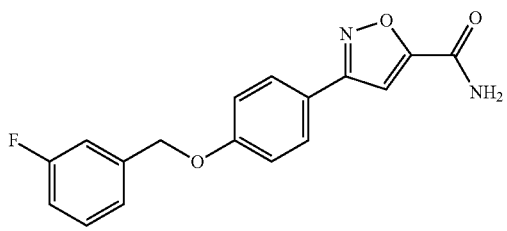 [SMILES: NC(=O)c1cc(-c2ccc(OCc3cccc(F)c3)cc2)no1]

3-[4-(3-Fluoro-benzyloxy)-phenyl]-isoxazole-5-carboxylic acid (which may be prepared as described in Preparation of Intermediate 5; 313 mg, 1.0 mmol) and diisopropylethylamine (275 µL, 1.6 mmol) were dissolved in $CH_2Cl_2$ (6 mL). N'-(3-dimethylaminopropyl)-N-ethylcarbodiimide hydrochloride (160 mg, 3 mmol), 1-hydroxybenzotriazole (180 mg, 1.16 mmol), and $NH_4Cl$ (53.5 mg, 3 mmol) were added. The reaction mixture was stirred at room temperature. DMF (6 mL) was added to the heterogeneous reaction mixture and the resulting solution was stirred at room temperature for 48 h. Additional equivalents of $NH_4Cl$, 1-hydroxybenzotriazole, N'-(3-dimethylaminopropyl)-N-ethylcarbodiimide hydrochloride, and diisopropylethylamine were added. The reaction mixture was stirred for an additional 48 h, and then purified by chromatography, eluting with 45% EtOAc/hexanes, to give 3-[4-(3-fluoro-benzyloxy)-phenyl]-isoxazole-5-carboxylic acid amide (65 mg, 21%), mp 221-222° C. LRMS (ESI$^+$): m/z [M+H]$^+$ 313.0. Impurity observed at m/z=423. $^1$H NMR (300 MHz, DMSO-d$_6$) δ ppm 8.34 (s, 1H), 7.98 (s, 1H), 7.84 (d, J=9.2 Hz, 2H), 7.52 (s, 1H), 7.42 (dd, J=8.1, 5.9 Hz, 1H), 7.29 (d, J=7.3 Hz, 2H), 7.15 (d, J=8.8 Hz, 3H), 5.20 (s, 2H).

Example 17

3-[4-(3-Trifluoromethyl-benzyloxy)-phenyl]-isoxazole-5-carboxylic acid amide

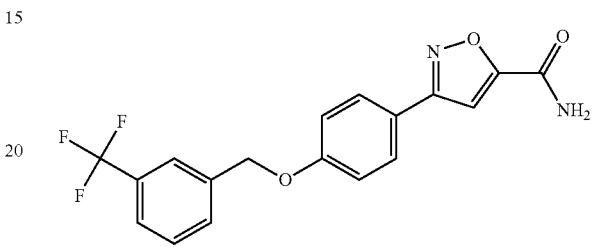

3-[4-(tert-Butyl-dimethyl-silanyloxy)-phenyl]-isoxazole-5-carboxylic acid amide (which may be prepared as described in Preparation of Intermediate 13; 40 mg, 0.126 mmol) was dissolved in DMF (1.5 mL). $K_2CO_3$ (19 mg, 0.14 mmol), 18-crown-6 (6 mg, 0.02 mmol), KF (8 mg, 0.14 mmol), and 3-(trifluoromethyl)benzyl chloride (20 µL, 0.129 mmol) were added. The reaction mixture was stirred at room temperature for 10 min and then at 40° C. for 12 h. $H_2O$ (2.5 mL) was added and the mixture was extracted with EtOAc. The organic layer was evaporated to give 3-[4-(3-trifluoromethyl-benzyloxy)-phenyl]-isoxazole-5-carboxylic acid amide (32.7 mg, 72%) as an off-white powder. HRMS Calcd. for $C_{18}H_{13}F_3N_2O_3$ (M$^+$), 362.0878. Found: 362.0872.

Example 18

3-[4-(3-Chloro-benzyloxy)-phenyl]-isoxazole-5-carboxylic acid amide

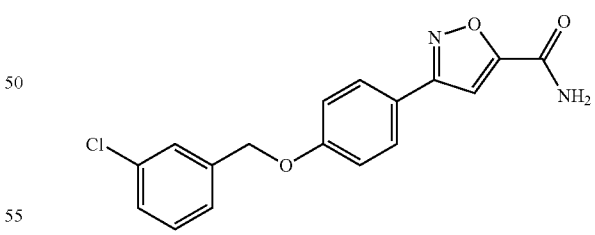

3-[4-(tert-Butyl-dimethyl-silanyloxy)-phenyl]-isoxazole-5-carboxylic acid amide (which may be prepared as described in Preparation of Intermediate 13; 40 mg, 0.126 mmol) was dissolved in DMF (1.5 mL). $K_2CO_3$ (19 mg, 0.14 mmol), 18-crown-6 (6 mg, 0.02 mmol), KF (8 mg, 0.14 mmol), and 3-chlorobenzyl chloride (20 µL, 0.129 mmol) were added. The reaction mixture was stirred at room temperature for 10 min and then at 40° C. for 12 h. $H_2O$ (2.5 mL) was added and the mixture was extracted with EtOAc. The organic layer was evaporated to give 3-[4-(3-chloro-benzyloxy)-phenyl]-isoxazole-5-carboxylic acid amide (31.8 mg, 77%) as an off-white powder. HRMS Calcd. for $C_{17}H_{13}ClN_2O_3$ (M+), 328.0615. Found: 328.0612.

Example 19

3-[4-(2-Chloro-benzyloxy)-phenyl]-isoxazole-5-carboxylic acid amide

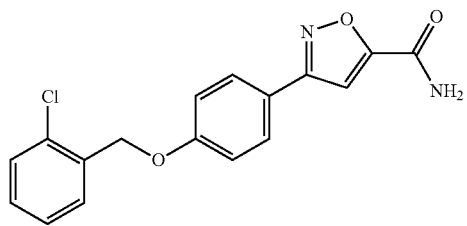

3-[4-(tert-Butyl-dimethyl-silanyloxy)-phenyl]-isoxazole-5-carboxylic acid amide (which may be prepared as described in Preparation of Intermediate 13; 40 mg, 0.126 mmol) was dissolved in DMF (1.5 mL). $K_2CO_3$ (19 mg, 0.14 mmol), 18-crown-6 (6 mg, 0.02 mmol), KF (8 mg, 0.14 mmol), and 2-chlorobenzyl chloride (20 μL, 0.158 mmol) were added. The reaction mixture was stirred at room temperature for 10 min and then at 40° C. for 12 h. $H_2O$ (2.5 mL) was added and the mixture was extracted with EtOAc. The organic layer was evaporated to give 3-[4-(2-chloro-benzyloxy)-phenyl]-isoxazole-5-carboxylic acid amide (29.2 mg, 71%) as a white powder. HRMS Calcd. for $C_{17}H_{13}ClN_2O_3$ (M+), 328.0615. Found: 328.0610.

Example 20

3-[4-(2-Bromo-benzyloxy)-phenyl]-isoxazole-5-carboxylic acid amide

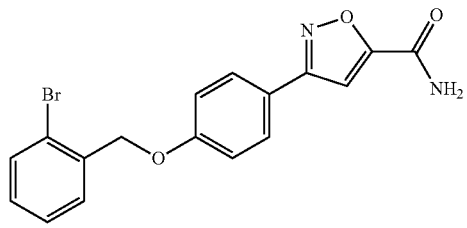 [SMILES: NC(=O)c1cc(-c2ccc(OCc3ccccc3Cl)cc2)no1]

3-[4-(tert-Butyl-dimethyl-silanyloxy)-phenyl]-isoxazole-5-carboxylic acid amide (which may be prepared as described in Preparation of Intermediate 13; 40 mg, 0.126 mmol) was dissolved in DMF (1.5 mL). $K_2CO_3$ (19 mg, 0.14 mmol), 18-crown-6 (5 mg, 0.02 mmol), KF (8 mg, 0.14 mmol), and 2-bromobenzyl bromide (20 mg, 0.10 mmol) were added. The reaction mixture was stirred at room temperature for 10 min and then at 40° C. for 12 h. $H_2O$ (2.5 mL) was added and the mixture was extracted with EtOAc. The organic layer was evaporated and purified by chromatography (35% EtOAc/hexanes) to give 3-[4-(2-bromo-benzyloxy)-phenyl]-isoxazole-5-carboxylic acid amide (7.5 mg, 16%) as a white powder. LRMS (ESI+): m/z [M+H]+ 376.1. $^1$H NMR (300 MHz, DMSO-$d_6$) δ ppm 8.35 (s, 1H), 7.98 (s, 1H), 7.85 (d, J=8.8 Hz, 2H), 7.64-7.72 (m, 1H), 7.59 (d, J=7.7 Hz, 1H), 7.53 (s, 1H), 7.39-7.48 (m, 1H), 7.26-7.36 (m, 1H), 7.16 (d, J=8.8 Hz, 2H), 5.19 (s, 2H).

Example 21

3-[4-(2-Trifluoromethyl-benzyloxy)-phenyl]-isoxazole-5-carboxylic acid amide

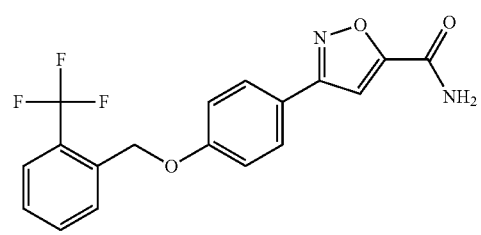 [SMILES: NC(=O)c1cc(-c2ccc(OCc3ccccc3C(F)(F)F)cc2)no1]

3-(4-Hydroxy-phenyl)-isoxazole-5-carboxylic acid amide (which may be prepared as described in Preparation of Intermediate 2; 40 mg, 0.196 mmol) was dissolved in DMF (1 mL). $K_2CO_3$ (19 mg, 0.14 mmol), tetrabutylammonium iodide (7 mg, 0.02 mmol), and 1-chloromethyl-2-trifluoromethyl-benzene (36 μL, 0.25 mmol) were added. The reaction mixture was heated at 40° C. for 14 h. The reaction mixture was partitioned between $H_2O$ (5 mL) and EtOAc (5 mL). The organic layer was dried ($Na_2SO_4$), filtered, evaporated, and purified by chromatography (30% EtOAc/hexanes) to give 3-[4-(2-trifluoromethyl-benzyloxy)-phenyl]-isoxazole-5-carboxylic acid amide (1.3 mg, 2%) as a white solid. HRMS Calcd. for $C_{18}H_{14}F_3N_2O_3$ (M+H)+, 363.0951. Found: 363.0950.

Example 22

3-[4-(2-Methanesulfonyl-benzyloxy)-phenyl]-isoxazole-5-carboxylic acid amide

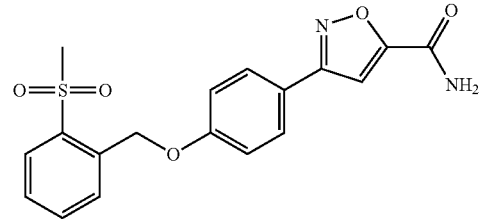 [SMILES: CS(=O)(=O)c1ccccc1COc1ccc(-c2cc(C(N)=O)on2)cc1]

3-(4-Hydroxy-phenyl)-isoxazole-5-carboxylic acid amide (which may be prepared as described in Preparation of Intermediate 2; 50 mg, 0.245 mmol) was dissolved in DMF (1.5 mL). $K_2CO_3$ (42 mg, 0.30 mmol), tetrabutylammonium iodide (14 mg, 0.038 mmol), and 1-bromomethyl-2-methylsulfonyl-benzene (which is available from Combi-Blocks; 62 mg, 0.25 mmol) were added. The reaction mixture was heated at 40° C. for 13 h. The reaction mixture was cooled to room temperature and partitioned between $H_2O$ (5 mL) and EtOAc (5 mL). The organic layer was dried ($Na_2SO_4$), filtered, evaporated, and purified twice by chromatography (40-60% EtOAc/hexanes) to give 3-[4-(2-methanesulfonyl-benzyloxy)-phenyl]-isoxazole-5-carboxylic acid amide (3 mg, 3%) as a white powder. HRMS Calcd. for $C_{18}H_{17}N_2O_5S$ (M+H)$^+$, 373.0853. Found: 373.0854.

Example 23

3-[4-(2-Chloro-phenoxymethyl)-phenyl]-isoxazole-5-carboxylic acid amide

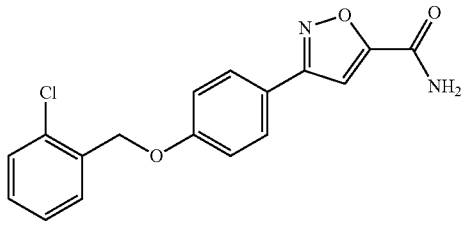 [SMILES: NC(=O)c1cc(-c2ccc(OCc3ccccc3Cl)cc2)no1]

To a mixture of 3-(4-bromomethyl-phenyl)-isoxazole-5-carboxylic acid amide (which may be prepared as described in Preparation of Intermediate 14; 40 mg, 0.142 mmol) in CH$_3$CN (2 mL) were added 2-chlorophenol (22 μL, 0.22 mmol) and K$_2$CO$_3$ (40 mg, 0.29 mmol). The mixture was heated at 90° C. for 4 h and then evaporated to dryness. The residue was purified by chromatography (66-75% EtOAc/hexanes) to give 3-[4-(2-chloro-phenoxymethyl)-phenyl]-isoxazole-5-carboxylic acid amide (37 mg, 79%) as a white solid. $^1$H NMR (300 MHz, DMSO-d$_6$) δ ppm 8.39 (br. s., 1H), 8.01 (br. s., 1H), 7.94 (d, J=8.1 Hz, 2H), 7.61 (d, J=9.5 Hz, 3H), 7.44 (dd, J=8.1, 1.5 Hz, 1H), 7.19-7.35 (m, 2H), 6.92-7.01 (m, 1H), 5.29 (s, 2H).

Example 24

3-[4-(3-Chloro-phenoxymethyl)-phenyl]-isoxazole-5-carboxylic acid amide

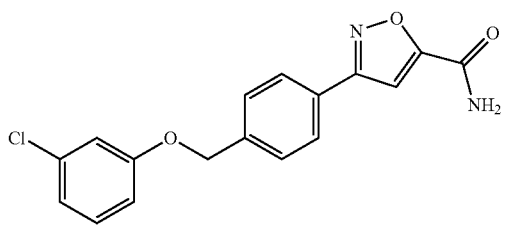 [SMILES: NC(=O)c1cc(-c2ccc(COc3cccc(Cl)c3)cc2)no1]

To a mixture of 3-(4-bromomethyl-phenyl)-isoxazole-5-carboxylic acid amide (which may be prepared as described in Preparation of Intermediate 14; 40 mg, 0.142 mmol) in CH$_3$CN (2 mL) were added 3-chlorophenol (28 mg, 0.22 mmol) and K$_2$CO$_3$ (40 mg, 0.29 mmol). The mixture was heated at 90° C. for 4 h and then evaporated to dryness. The residue was purified by chromatography (66-75% EtOAc/hexanes) to give 3-[4-(3-chloro-phenoxymethyl)-phenyl]-isoxazole-5-carboxylic acid amide (33 mg, 71%) as a white solid. $^1$H NMR (300 MHz, DMSO-d$_6$) δ ppm 8.38 (br. s., 1H), 8.01 (br. s., 1H), 7.92 (d, J=8.1 Hz, 2H), 7.55-7.66 (m, 3H), 7.23-7.36 (m, 1H), 7.09-7.15 (m, 1H), 6.95-7.05 (m, 2H), 5.21 (s, 2H).

Example 25

3-[4-(4-Chloro-phenoxymethyl)-phenyl]-isoxazole-5-carboxylic acid amide

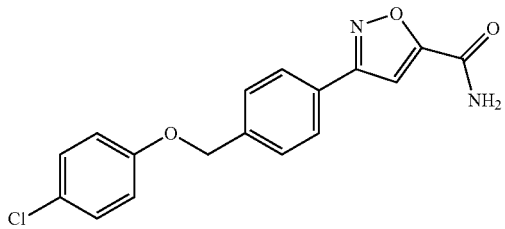 [SMILES: NC(=O)c1cc(-c2ccc(COc3ccc(Cl)cc3)cc2)no1]

To a mixture of 3-(4-bromomethyl-phenyl)-isoxazole-5-carboxylic acid amide (which may be prepared as described in Preparation of Intermediate 14; 30 mg, 0.107 mmol) in CH$_3$CN (2 mL) were added 4-chlorophenol (21 mg, 0.16 mmol) and K$_2$CO$_3$ (30 mg, 0.22 mmol). The mixture was heated at 90° C. for 4 h and then evaporated to dryness. The residue was purified by chromatography (66-75% EtOAc/hexanes) to give 3-[4-(4-chloro-phenoxymethyl)-phenyl]-isoxazole-5-carboxylic acid amide (29 mg, 82%) as a white solid. $^1$H NMR (300 MHz, DMSO-d$_6$) δ ppm 8.39 (s, 1H), 8.01 (s, 1H), 7.91 (d, J=8.2 Hz, 2H), 7.50-7.65 (m, 3H), 7.26-7.38 (m, 2H), 6.97-7.11 (m, 2H), 5.17 (s, 2H).

Example 26

3-(4-o-Tolyloxymethyl-phenyl)-isoxazole-5-carboxylic acid amide

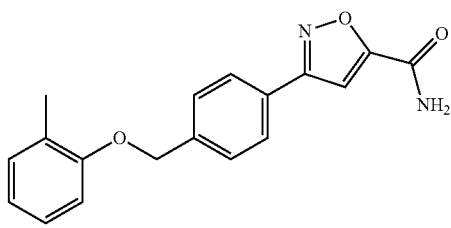 [SMILES: Cc1ccccc1OCc1ccc(-c2cc(C(N)=O)on2)cc1]

To a mixture of 3-(4-bromomethyl-phenyl)-isoxazole-5-carboxylic acid amide (which may be prepared as described in Preparation of Intermediate 14; 30 mg, 0.107 mmol) in CH$_3$CN (2 mL) were added o-cresol (20 mg, 0.185 mmol) and K$_2$CO$_3$ (30 mg, 0.22 mmol). The mixture was heated at 90° C. for 16 h and then evaporated to dryness. The residue was purified by chromatography (66-75% EtOAc/hexanes) to give 3-(4-o-tolyloxymethyl-phenyl)-isoxazole-5-carboxylic acid amide (21 mg, 64%) as a white powder. $^1$H NMR (300 MHz, DMSO-d$_6$) δ ppm 8.38 (br. s., 1H), 8.00 (br. s., 1H), 7.92 (d, J=8.1 Hz, 2H), 7.53-7.67 (m, 3H), 7.05-7.20 (m, 2H), 6.99 (d, J=7.7 Hz, 1H), 6.74-6.90 (m, 1H), 5.19 (s, 2H), 2.21 (s, 3H).

Example 27

3-(4-m-Tolyloxymethyl-phenyl)-isoxazole-5-carboxylic acid amide

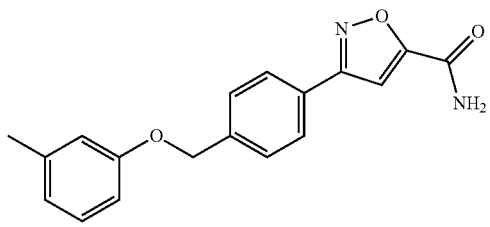 [SMILES: Cc1cccc(OCc2ccc(-c3cc(C(N)=O)on3)cc2)c1]

To a mixture of 3-(4-bromomethyl-phenyl)-isoxazole-5-carboxylic acid amide (which may be prepared as described in Preparation of Intermediate 14; 30 mg, 0.107 mmol) in CH$_3$CN (2 mL) were added m-cresol (20 mg, 0.185 mmol) and K$_2$CO$_3$ (30 mg, 0.22 mmol). The mixture was heated at 90° C. for 16 h and then evaporated to dryness. The residue was purified by chromatography (66-75% EtOAc/hexanes) to give 3-(4-m-tolyloxymethyl-phenyl)-isoxazole-5-carboxylic acid amide (20 mg, 61%) as a white powder. $^1$H NMR (300 MHz, DMSO-d$_6$) δ ppm 8.38 (br. s., 1H), 8.00 (br. s., 1H), 7.86-7.95 (m, 3H), 7.53-7.63 (m, 4H), 7.11-7.22 (m, 1H), 6.69-6.89 (m, 3H), 5.15 (s, 2H), 2.26 (s, 3H).

Example 28

3-[4-(2-Methoxy-phenoxymethyl)-phenyl]-isoxazole-5-carboxylic acid amide

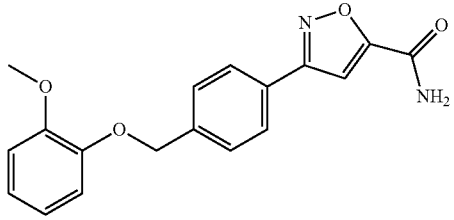 [SMILES: COc1ccccc1OCc1ccc(-c2cc(C(N)=O)on2)cc1]

To a mixture of 3-(4-bromomethyl-phenyl)-isoxazole-5-carboxylic acid amide (which may be prepared as described in Preparation of Intermediate 14; 30 mg, 0.107 mmol) in CH$_3$CN (2 mL) were added 2-methoxyphenol (21 μL, 0.19 mmol) and K$_2$CO$_3$ (30 mg, 0.22 mmol). The mixture was heated at 85° C. for 16 h and then evaporated to dryness. The residue was purified by chromatography (66-75% EtOAc/hexanes) to give 3-[4-(2-methoxy-phenoxymethyl)-phenyl]-isoxazole-5-carboxylic acid amide (12 mg, 35%) as a white powder. $^1$H NMR (300 MHz, DMSO-d$_6$) δ ppm 8.39 (br. s., 1H), 8.01 (br. s., 1H), 7.91 (d, J=8.4 Hz, 2H), 7.53-7.63 (m, 3H), 6.78-7.07 (m, 3H), 5.14 (s, 2H), 3.25-3.37 (m, 3H).

Example 29

3-[4-(3-Methoxy-phenoxymethyl)-phenyl]-isoxazole-5-carboxylic acid amide

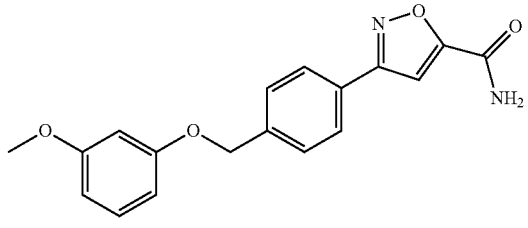 [SMILES: COc1cccc(OCc2ccc(-c3cc(C(N)=O)on3)cc2)c1]

To a mixture of 3-(4-bromomethyl-phenyl)-isoxazole-5-carboxylic acid amide (which may be prepared as described in Preparation of Intermediate 14; 30 mg, 0.107 mmol) in CH$_3$CN (2 mL) were added 3-methoxyphenol (21 μL, 0.19 mmol) and K$_2$CO$_3$ (30 mg, 0.22 mmol). The mixture was heated at 85° C. for 16 h and then evaporated to dryness. The residue was purified by chromatography (66-75% EtOAc/hexanes) to give 3-[4-(3-methoxy-phenoxymethyl)-phenyl]-isoxazole-5-carboxylic acid amide (20 mg, 58%) as a white powder. $^1$H NMR (300 MHz, DMSO-d$_6$) δ ppm 8.38 (br. s., 1H), 8.00 (br. s., 1H), 7.91 (d, J=8.1 Hz, 2H), 7.54-7.62 (m, 3H), 7.18 (t, J=7.9 Hz, 1H), 6.47-6.64 (m, 3H), 5.16 (s, 2H), 3.26-3.33 (m, 3H).

Example 30

3-[4-(4-Methoxy-phenoxymethyl)-phenyl]-isoxazole-5-carboxylic acid amide

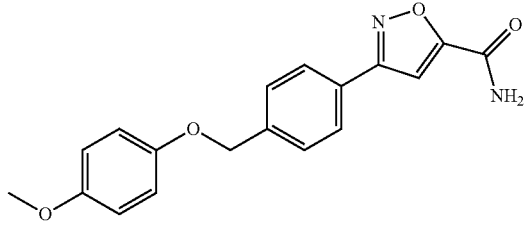 [SMILES: COc1ccc(OCc2ccc(-c3cc(C(N)=O)on3)cc2)cc1]

To a mixture of 3-(4-bromomethyl-phenyl)-isoxazole-5-carboxylic acid amide (which may be prepared as described in Preparation of Intermediate 14; 30 mg, 0.107 mmol) in CH$_3$CN (2 mL) were added 4-methoxyphenol (24 mg, 0.22 mmol) and K$_2$CO$_3$ (30 mg, 0.22 mmol). The mixture was heated at 85° C. for 16 h and then evaporated to dryness. The residue was purified by chromatography (66-75% EtOAc/hexanes) to give 3-[4-(4-methoxy-phenoxymethyl)-phenyl]-isoxazole-5-carboxylic acid amide (12 mg, 35%) as a white powder. $^1$H NMR (300 MHz, DMSO-d$_6$) δ ppm 8.38 (br. s., 1H), 8.00 (br. s., 1H), 7.90 (d, J=8.4 Hz, 2H), 7.52-7.64 (m, 3H), 6.90-7.00 (m, 1H), 6.81-6.89 (m, 1H), 5.11 (s, 1H), 3.26-3.34 (m, 3H).

Example 31

3-[4-(2,6-Dimethyl-phenoxymethyl)-phenyl]-isoxazole-5-carboxylic acid amide

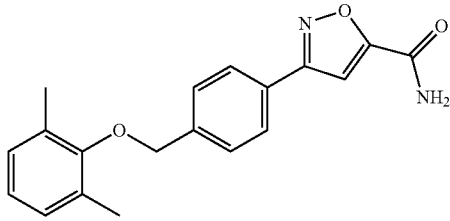 [SMILES: Cc1cccc(C)c1OCc1ccc(-c2cc(C(N)=O)on2)cc1]

To a mixture of 3-(4-bromomethyl-phenyl)-isoxazole-5-carboxylic acid amide (which may be prepared as described in Preparation of Intermediate 14; 30 mg, 0.107 mmol) in CH$_3$CN (2 mL) were added 2,6-dimethylphenol (22 mg, 0.18 mmol) and K$_2$CO$_3$ (30 mg, 0.22 mmol). The mixture was heated at 90° C. for 16 h and then evaporated to dryness. The residue was purified by chromatography (66-75% EtOAc/hexanes) to give 3-[4-(2,6-dimethyl-phenoxymethyl)-phenyl]-isoxazole-5-carboxylic acid amide (28 mg, 81%) as a white powder. $^1$H NMR (300 MHz, DMSO-d$_6$) δ ppm 8.39 (br. s., 1H), 8.01 (br. s., 1H), 7.94 (d, J=8.4 Hz, 2H), 7.55-7.69 (m, 3H), 7.00-7.09 (m, 2H), 6.88-6.98 (m, 1H), 4.86 (s, 2H), 2.25 (s, 6H).

Example 32

3-[4-(2-Isopropyl-phenoxymethyl)-phenyl]-isoxazole-5-carboxylic acid amide

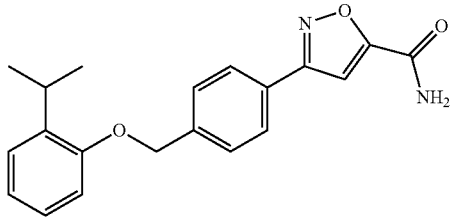 [SMILES: CC(C)c1ccccc1OCc1ccc(-c2cc(C(N)=O)on2)cc1]

To a mixture of 3-(4-bromomethyl-phenyl)-isoxazole-5-carboxylic acid amide (which may be prepared as described in Preparation of Intermediate 14; 30 mg, 0.107 mmol) in CH$_3$CN (2 mL) were added 2-isopropylphenol (25 μL, 0.185 mmol) and K$_2$CO$_3$ (30 mg, 0.22 mmol). The mixture was heated at 90° C. for 16 h and then evaporated to dryness. The residue was purified by chromatography (66-75% EtOAc/hexanes) to give 3-[4-(2-isopropyl-phenoxymethyl)-phenyl]-isoxazole-5-carboxylic acid amide (28 mg, 78%) as a white powder. $^1$H NMR (300 MHz, DMSO-d$_6$) δ ppm 8.39 (br. s., 1H), 8.01 (br. s., 1H), 7.93 (d, J=8.1 Hz, 2H), 7.55-7.65 (m, 3H), 7.21 (dd, J=7.5, 1.6 Hz, 1H), 7.06-7.17 (m, 1H), 7.01 (d, J=7.3 Hz, 1H), 6.84-6.96 (m, 1H), 5.18 (s, 2H), 3.22-3.39 (m, 3H, including water peak), 1.18 (d, J=7.0 Hz, 6H).

Example 33

3-[4-(2-Trifluoromethoxy-phenoxymethyl)-phenyl]-isoxazole-5-carboxylic acid amide

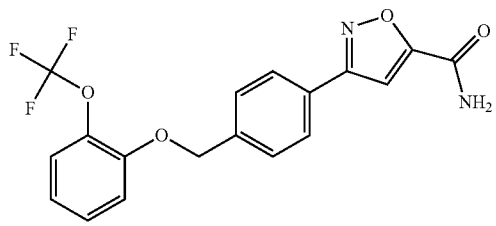 [SMILES: NC(=O)c1cc(-c2ccc(COc3ccccc3OC(F)(F)F)cc2)no1]

To a mixture of 3-(4-bromomethyl-phenyl)-isoxazole-5-carboxylic acid amide (which may be prepared as described in Preparation of Intermediate 14; 30 mg, 0.107 mmol) in CH$_3$CN (2 mL) were added 2-trifluoromethoxyphenol (25 μL, 0.187 mmol) and K$_2$CO$_3$ (30 mg, 0.22 mmol). The mixture was heated at 90° C. for 16 h and then evaporated to dryness. The residue was purified by chromatography (66-75% EtOAc/hexanes) to give 3-[4-(2-trifluoromethoxy-phenoxymethyl)-phenyl]-isoxazole-5-carboxylic acid amide (30 mg, 74%) as a white powder. $^1$H NMR (300 MHz, DMSO-d$_6$) δ ppm 8.39 (br. s., 1H), 8.01 (br. s., 1H), 7.94 (d, J=8.4 Hz, 2H), 7.54-7.63 (m, 3H), 7.26-7.41 (m, 3H), 6.97-7.07 (m, 1H), 5.29 (s, 2H).

Example 34

3-[4-(2-Ethyl-phenoxymethyl)-phenyl]-isoxazole-5-carboxylic acid amide

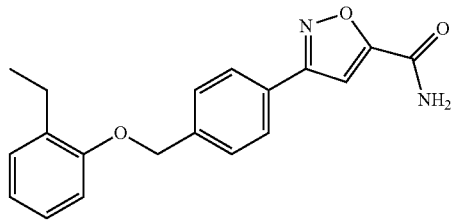 [SMILES: CCc1ccccc1OCc1ccc(-c2cc(C(N)=O)on2)cc1]

To a mixture of 3-(4-bromomethyl-phenyl)-isoxazole-5-carboxylic acid amide (which may be prepared as described in Preparation of Intermediate 14; 30 mg, 0.107 mmol) in CH$_3$CN (2 mL) were added 2-ethylphenol (21 μL, 0.178 mmol) and K$_2$CO$_3$ (30 mg, 0.22 mmol). The mixture was heated at 90° C. for 16 h and then evaporated to dryness. The residue was purified by chromatography (66-75% EtOAc/hexanes) to give 3-[4-(2-ethyl-phenoxymethyl)-phenyl]-isoxazole-5-carboxylic acid amide (20 mg, 58%) as a white powder. $^1$H NMR (300 MHz, DMSO-d$_6$) δ ppm 8.39 (br. s., 1H), 8.01 (br. s., 1H), 7.93 (d, J=8.1 Hz, 2H), 7.55-7.64 (m, 3H), 7.08-7.19 (m, 2H), 7.01 (d, J=8.1 Hz, 1H), 6.87 (t, J=7.3 Hz, 1H), 5.19 (s, 2H), 2.63 (q, J=7.4 Hz, 2H), 1.10-1.19 (m, 3H).

Example 35

3-[4-(2-tert-Butyl-phenoxymethyl)-phenyl]-isoxazole-5-carboxylic acid amide

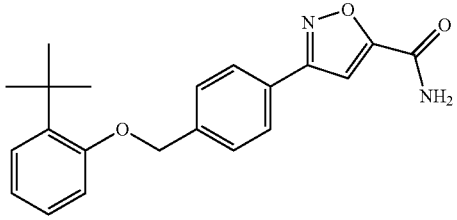 [SMILES: CC(C)(C)c1ccccc1OCc1ccc(-c2cc(C(N)=O)on2)cc1]

To a mixture of 3-(4-bromomethyl-phenyl)-isoxazole-5-carboxylic acid amide (which may be prepared as described in Preparation of Intermediate 14; 30 mg, 0.107 mmol) in $CH_3CN$ (2 mL) were added 2-tert-butylphenol (28 µL, 0.182 mmol) and $K_2CO_3$ (30 mg, 0.22 mmol). The mixture was heated at 90° C. for 16 h and then evaporated to dryness. The residue was purified by chromatography (66-75% EtOAc/hexanes) to give 3-[4-(2-tert-butyl-phenoxymethyl)-phenyl]-isoxazole-5-carboxylic acid amide (28 mg, 75%) as a white powder. $^1$H NMR (300 MHz, DMSO-$d_6$) δ ppm 8.39 (s, 1H), 8.02 (s, 1H), 7.95 (d, J=8.5 Hz, 2H), 7.57-7.67 (m, 2H), 7.12-7.28 (m, 2H), 7.00-7.09 (m, 1H), 6.82-6.94 (m, 1H), 5.20 (s, 2H), 1.34 (s, 9H).

Example 36

3-[4-(2-Trifluoromethyl-phenoxymethyl)-phenyl]-isoxazole-5-carboxylic acid amide

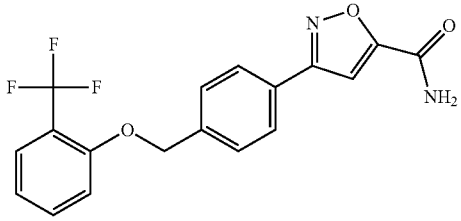

To a mixture of 3-(4-bromomethyl-phenyl)-isoxazole-5-carboxylic acid amide (which may be prepared as described in Preparation of Intermediate 14; 30 mg, 0.107 mmol) in $CH_3CN$ (2 mL) were added 2-hydroxybenzotrifluoride (29 mg, 0.179 mmol) and $K_2CO_3$ (30 mg, 0.22 mmol). The mixture was heated at 90° C. for 16 h and then evaporated to dryness. The residue was purified by chromatography (66-75% EtOAc/hexanes) to give 3-[4-(2-trifluoromethyl-phenoxymethyl)-phenyl]-isoxazole-5-carboxylic acid amide (30 mg, 77%) as a white powder. $^1$H NMR (300 MHz, DMSO-$d_6$) δ ppm 8.39 (s, 1H), 8.02 (s, 1H), 7.94 (d, J=8.5 Hz, 2H), 7.54-7.68 (m, 5H), 7.34 (d, J=8.5 Hz, 1H), 7.10 (t, J=7.7 Hz, 1H), 5.35 (s, 2H).

Example 37

3-[4-(2-Cyano-phenoxymethyl)-phenyl]-isoxazole-5-carboxylic acid amide

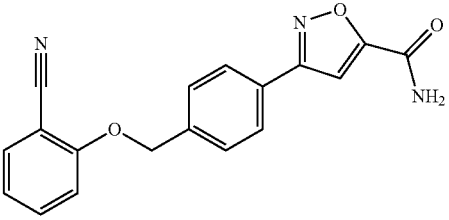 [SMILES: N#Cc1ccccc1OCc1ccc(-c2cc(C(N)=O)on2)cc1]

To a mixture of 3-(4-bromomethyl-phenyl)-isoxazole-5-carboxylic acid amide (which may be prepared as described in Preparation of Intermediate 14; 30 mg, 0.107 mmol) in $CH_3CN$ (2 mL) were added 2-hydroxybenzonitrile (22 mg, 0.184 mmol) and $K_2CO_3$ (30 mg, 0.22 mmol). The mixture was heated at 90° C. for 16 h and then evaporated to dryness. The residue was purified by chromatography (66-75% EtOAc/hexanes) to give 3-[4-(2-cyano-phenoxymethyl)-phenyl]-isoxazole-5-carboxylic acid amide (26 mg, 76%) as a white powder. $^1$H NMR (300 MHz, DMSO-$d_6$) δ ppm 8.39 (br. s., 1H), 8.00 (br. s., 1H), 7.95 (d, J=8.2 Hz, 2H), 7.75 (dd, J=7.5, 1.5 Hz, 1H), 7.54-7.65 (m, 3H), 7.33 (d, J=8.5 Hz, 1H), 7.11 (t, J=7.5 Hz, 1H), 5.37 (s, 2H).

Example 38

3-[4-(3-Methyl-pyridin-2-yloxymethyl)-phenyl]-isoxazole-5-carboxylic acid amide

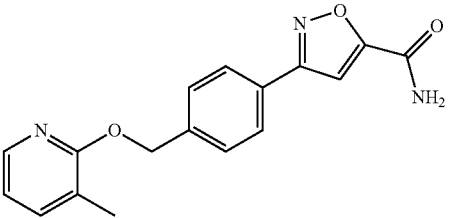 [SMILES: Cc1cccnc1OCc1ccc(-c2cc(C(N)=O)on2)cc1]

To a mixture of 3-(4-bromomethyl-phenyl)-isoxazole-5-carboxylic acid amide (which may be prepared as described in Preparation of Intermediate 14; 30 mg, 0.107 mmol) in $CH_3CN$ (2 mL) were added 3-methyl-2-pyridone (20 mg, 0.18 mmol) and $K_2CO_3$ (30 mg, 0.22 mmol). The mixture was heated at 90° C. for 16 h and then evaporated to dryness. The residue was purified by chromatography (66-75% EtOAc/hexanes) to give 3-[4-(3-methyl-pyridin-2-yloxymethyl)-phenyl]-isoxazole-5-carboxylic acid amide (20 mg, 60%) as a white powder. $^1$H NMR (300 MHz, DMSO-$d_6$) δ ppm 8.38 (br. s., 1H), 7.99 (br. s., 1H), 7.86 (d, J=8.5 Hz, 2H), 7.68 (d, J=6.9 Hz, 1H), 7.56 (d, J=1.2 Hz, 1H), 7.41 (d, J=8.2 Hz, 2H), 7.29 (dd, J=14.0, 6.2 Hz, 2H), 7.18 (d, J=6.6 Hz, 1H), 5.98-6.24 (m, 2H), 5.15 (s, 2H), 1.99 (s, 3H).

Example 39

3-[4-(2-Fluoro-phenoxymethyl)-phenyl]-isoxazole-5-carboxylic acid amide

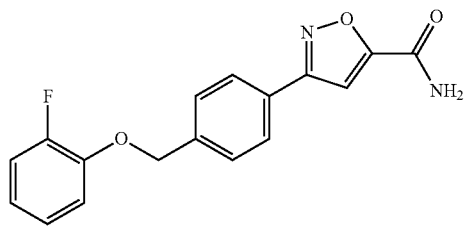 [SMILES: NC(=O)c1cc(-c2ccc(COc3ccccc3F)cc2)no1]

To a mixture of 3-(4-bromomethyl-phenyl)-isoxazole-5-carboxylic acid amide (which may be prepared as described in Preparation of Intermediate 14; 30 mg, 0.107 mmol) in CH$_3$CN (2 mL) were added 2-fluorophenol (16 μL, 0.18 mmol) and K$_2$CO$_3$ (30 mg, 0.22 mmol). The mixture was heated at 90° C. for 16 h and then evaporated to dryness. The residue was purified by chromatography (66-75% EtOAc/hexanes) to give 3-[4-(2-fluoro-phenoxymethyl)-phenyl]-isoxazole-5-carboxylic acid amide (28 mg, 84%) as a white powder. $^1$H NMR (300 MHz, DMSO-d$_6$) δ ppm 8.38 (br. s., 1H), 8.00 (br. s., 1H), 7.93 (d, J=8.2 Hz, 2H), 7.60 (d, J=7.2 Hz, 3H), 7.17-7.29 (m, 2H), 7.11 (t, J=7.7 Hz, 1H), 6.87-7.01 (m, 1H), 5.25 (s, 2H).

Example 40

3-[4-(5-Chloro-2-methyl-phenoxymethyl)-phenyl]-isoxazole-5-carboxylic acid amide

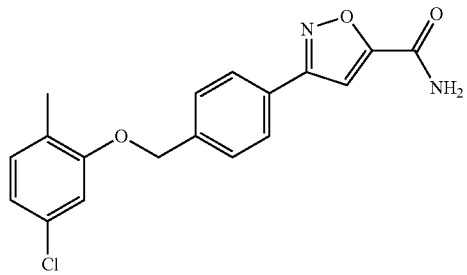

To a mixture of 3-(4-bromomethyl-phenyl)-isoxazole-5-carboxylic acid amide (which may be prepared as described in Preparation of Intermediate 14; 30 mg, 0.107 mmol) in CH$_3$CN (2 mL) were added 5-chloro-2-methyl-phenol (26 mg, 0.18 mmol) and K$_2$CO$_3$ (30 mg, 0.22 mmol). The mixture was heated at 90° C. for 16 h and then evaporated to dryness. The residue was purified by chromatography (66-75% EtOAc/hexanes) to give 3-[4-(5-chloro-2-methyl-phenoxymethyl)-phenyl]-isoxazole-5-carboxylic acid amide (20 mg, 55%) as a white powder. $^1$H NMR (300 MHz, DMSO-d$_6$) δ ppm 8.38 (br. s., 1H), 8.01 (br. s., 1H), 7.93 (d, J=8.2 Hz, 2H), 7.54-7.64 (m, 3H), 7.18 (d, J=7.8 Hz, 1H), 7.09 (d, J=1.8 Hz, 1H), 6.91 (dd, J=8.0, 2.0 Hz, 1H), 5.22 (s, 2H), 2.18 (s, 3H).

Example 41

3-[4-(3-Chloro-2-methyl-phenoxymethyl)-phenyl]-isoxazole-5-carboxylic acid amide

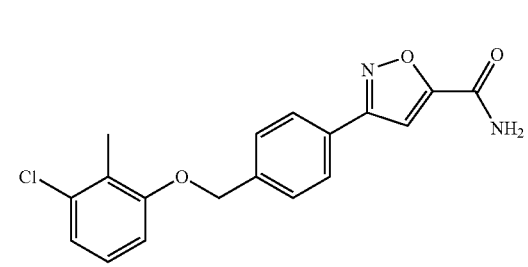 [SMILES: Cc1c(Cl)cccc1OCc1ccc(-c2cc(C(N)=O)on2)cc1]

To a mixture of 3-(4-bromomethyl-phenyl)-isoxazole-5-carboxylic acid amide (which may be prepared as described in Preparation of Intermediate 14; 30 mg, 0.107 mmol) in CH$_3$CN (2 mL) were added 3-chloro-2-methylphenol (26 mg, 0.18 mmol) and K$_2$CO$_3$ (30 mg, 0.22 mmol). The mixture was heated at 90° C. for 16 h and then evaporated to dryness. The residue was purified by chromatography (66-75% EtOAc/hexanes) to give 3-[4-(3-chloro-2-methyl-phenoxymethyl)-phenyl]-isoxazole-5-carboxylic acid amide (15 mg, 41%) as a white powder. $^1$H NMR (300 MHz, DMSO-d$_6$) δ ppm 8.38 (br. s., 1H), 8.00 (br. s., 1H), 7.93 (d, J=8.2 Hz, 2H), 7.55-7.65 (m, 3H), 7.16 (d, J=8.5 Hz, 1H), 7.02 (d, J=7.5 Hz, 2H), 5.22 (s, 2H), 2.26 (s, 3H).

Example 42

3-[4-(4-Fluoro-2-methyl-phenoxymethyl)-phenyl]-isoxazole-5-carboxylic acid amide

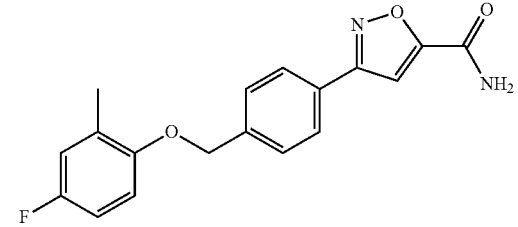 [SMILES: Cc1cc(F)ccc1OCc1ccc(-c2cc(C(N)=O)on2)cc1]

To a mixture of 3-(4-bromomethyl-phenyl)-isoxazole-5-carboxylic acid amide (which may be prepared as described in Preparation of Intermediate 14; 30 mg, 0.107 mmol) in CH$_3$CN (2 mL) were added 4-fluoro-2-methylphenol (20 μL, 0.18 mmol) and K$_2$CO$_3$ (30 mg, 0.22 mmol). The mixture was heated at 90° C. for 16 h and then evaporated to dryness. The residue was purified by chromatography (66-75% EtOAc/hexanes) to give 3-[4-(4-fluoro-2-methyl-phenoxymethyl)-phenyl]-isoxazole-5-carboxylic acid amide (28 mg, 80%) as a white powder. $^1$H NMR (300 MHz, DMSO-d$_6$) δ ppm 8.38

(br. s., 1H), 8.01 (br. s., 1H), 7.92 (d, J=8.2 Hz, 2H), 7.54-7.63 (m, 3H), 6.91-7.08 (m, 3H), 5.16 (s, 2H), 2.21 (s, 3H).

Example 43

3-[4-(5-Fluoro-2-methyl-phenoxymethyl)-phenyl]-isoxazole-5-carboxylic acid amide

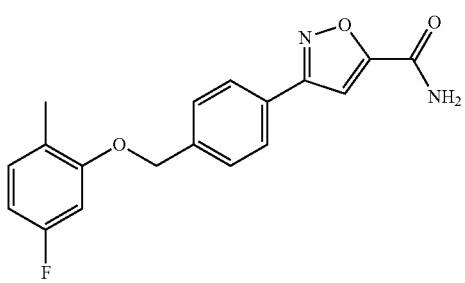 [SMILES: Cc1ccc(F)cc1OCc1ccc(-c2cc(C(N)=O)on2)cc1]

To a mixture of 3-(4-bromomethyl-phenyl)-isoxazole-5-carboxylic acid amide (which may be prepared as described in Preparation of Intermediate 14; 30 mg, 0.107 mmol) in CH$_3$CN (2 mL) were added 5-fluoro-2-methylphenol (20 µL. 0.18 mmoL) and K$_2$CO$_3$ (30 mg, 0.22 mmol). The mixture was heated at 90° C. for 16 h and then evaporated to dryness. The residue was purified by chromatography (66-75% EtOAc/hexanes) to give 3-[4-(5-fluoro-2-methyl-phenoxymethyl)-phenyl]-isoxazole-5-carboxylic acid amide (24 mg, 69%) as a white powder. $^1$H NMR (300 MHz, DMSO-d$_6$) δ ppm 8.38 (br. s., 1H), 8.01 (br. s., 1H), 7.93 (d, J=8.2 Hz, 2H), 7.52-7.65 (m, 3H), 7.16 (t, J=7.5 Hz, 1H), 6.92 (dd, J=11.3, 2.6 Hz, 1H), 6.67 (td, J=8.5, 2.7 Hz, 1H), 5.20 (s, 2H), 2.16 (s, 3H).

Example 44

3-[4-(2-Methyl-pyridin-3-yloxymethyl)-phenyl]-isoxazole-5-carboxylic acid amide

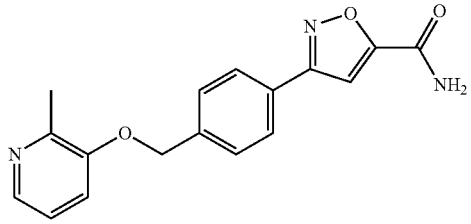 [SMILES: Cc1ncccc1OCc1ccc(-c2cc(C(N)=O)on2)cc1]

To a mixture of 3-(4-bromomethyl-phenyl)-isoxazole-5-carboxylic acid amide (which may be prepared as described in Preparation of Intermediate 14; 30 mg, 0.107 mmol) in CH$_3$CN (2 mL) were added 3-hydroxy-2-methylpyridine (20 mg, 0.18 mmol) and K$_2$CO$_3$ (30 mg, 0.22 mmol). The mixture was heated at 90° C. overnight and then evaporated to dryness. The residue was purified by chromatography (66-75% EtOAc/hexanes) to give 3-[4-(2-methyl-pyridin-3-yloxymethyl)-phenyl]-isoxazole-5-carboxylic acid amide (12 mg, 36%) as a white powder. $^1$H NMR (DMSO-d$_6$) δ ppm 8.37 (br. s., 1H), 8.00 (dd, J=4.7, 1.1 Hz, 2H), 7.93 (d, J=8.5 Hz, 2H), 7.54-7.65 (m, 3H), 7.34-7.43 (m, 1H), 7.17 (dd, J=8.5, 4.8 Hz, 1H), 5.23 (s, 2H), 2.41 (s, 3H).

Example 45

3-[4-(2,3-Dihydro-indol-1-ylmethyl)-phenyl]-isoxazole-5-carboxylic acid amide

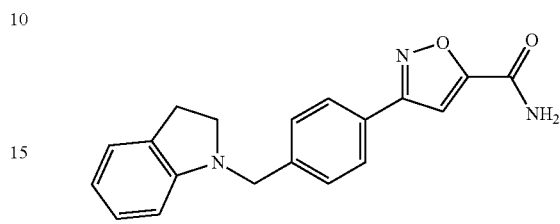

To a solution of indoline (13 µL, 0.116 mmol) in dichloroethane (1 mL) was added Na(OAc)$_3$BH (74 mg, 0.35 mmol). The mixture was stirred at room temperature under argon for 20 min. A slurry of 3-(4-formyl-phenyl)-isoxazole-5-carboxylic acid amide (which may be prepared as described in Preparation of Intermediate 20; 25 mg, 0.116 mmol) in dichloroethane (1 mL) was added, followed by AcOH (20 µL). The reaction mixture was stirred at room temperature overnight. 1 M Na$_2$CO$_3$ solution was added and the mixture was extracted with EtOAc (3×25 mL). The organic layer was washed with brine, dried (Na$_2$SO$_4$), evaporated, and purified by chromatography (12.5-20% acetone/CH$_2$Cl$_2$) to give 3-[4-(2,3-dihydro-indol-1-ylmethyl)-phenyl]-isoxazole-5-carboxylic acid amide (24 mg, 65%), as an off-white powder. $^1$H NMR (300 MHz, DMSO-d$_6$) δ ppm 8.27 (br. s., 1H), 7.90 (br. s., 1H), 7.79 (d, J=8.2 Hz, 2H), 7.48 (s, 1H), 7.41 (d, J=8.2 Hz, 2H), 6.95 (d, J=6.9 Hz, 1H), 6.88 (t, J=7.7 Hz, 1H), 6.42-6.55 (m, 2H), 4.23 (s, 2H), 3.14-3.21 (m, 2H), 2.75-2.87 (m, 2H).

Example 46

3-[4-(1,3-Dihydro-isoindol-2-ylmethyl)-phenyl]-isoxazole-5-carboxylic acid amide

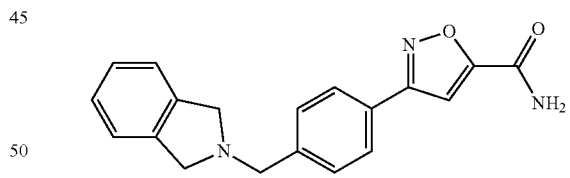

To a solution of isoindoline (11 µL, 0.097 mmol) in dichloroethane (1 mL) was added Na(OAc)$_3$BH (59 mg, 0.278 mmol). The mixture was stirred at room temperature under argon for 20 min. A slurry of 3-(4-formyl-phenyl)-isoxazole-5-carboxylic acid amide (which may be prepared as described in Preparation of Intermediate 20; 20 mg, 0.093 mmol) in dichloroethane (1 mL) was added, followed by AcOH (20 µL). The reaction mixture was stirred at room temperature overnight. 1 M Na$_2$CO$_3$ solution was added and the mixture was extracted with CHCl$_3$ (3×25 mL). The organic layer was washed with brine, dried (Na$_2$SO$_4$), evaporated, and purified by chromatography (20-25% acetone/CH$_2$Cl$_2$) to give 3-[4-(1,3-dihydro-indol-2-ylmethyl)-phenyl]-isoxazole-5-carboxylic acid amide (10 mg, 32%) as an off-white powder. $^1$H NMR (300 MHz, DMSO-d$_6$) δ ppm 8.36 (br. s., 1H), 7.99 (br.

s., 1H), 7.88 (d, J=8.2 Hz, 2H), 7.48-7.61 (m, 3H), 7.09-7.26 (m, 4H), 5.74 (s, 2H), 4.07 (br. s., 1H), 3.92 (s, 1H), 3.30 (d, J=3.0 Hz, 2H), 3.15 (d, J=4.8 Hz, 2H).

Example 47

3-(4-Indol-1-ylmethyl-phenyl)-isoxazole-5-carboxylic acid amide

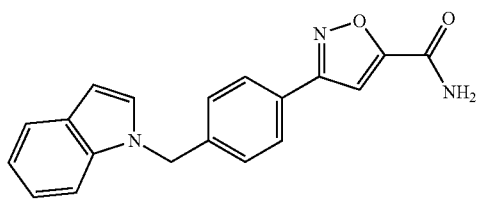 [SMILES: NC(=O)c1cc(-c2ccc(Cn3ccc4ccccc43)cc2)no1]

To a mixture of indole (13 mg, 0.11 mmol) in DMF (1 mL) was added NaH (60% dispersion; 5 mg, 0.125 mmol). The mixture was stirred for 20 min and then a solution of 3-(4-bromomethyl-phenyl)-isoxazole-5-carboxylic acid amide (which may be prepared as described in Preparation of Intermediate 14; 30 mg, 0.107 mmol) in DMF (1 mL) was added. The reaction mixture was stirred at room temperature overnight. $H_2O$ was added and the mixture was extracted with EtOAc (3×25 mL). The combined organic layers were washed three times with $H_2O$/brine, dried ($Na_2SO_4$), evaporated, and purified by chromatography (10-25% acetone/$CH_2Cl_2$) to give 3-(4-indol-1-ylmethyl-phenyl)-isoxazole-5-carboxylic acid amide (6 mg, 18%) as an off-white solid. $^1$H NMR (300 MHz, DMSO-$d_6$) δ ppm 8.34 (br. s., 1H), 7.97 (br. s., 1H), 7.82 (d, J=8.2 Hz, 2H), 7.48-7.61 (m, 3H), 7.43 (d, J=7.8 Hz, 1H), 7.30 (d, J=8.2 Hz, 2H), 6.94-7.14 (m, 2H), 6.49 (d, J=3.0 Hz, 1H), 5.49 (s, 2H).

Example 48

3-(4-Benzotriazol-1-ylmethyl-phenyl)-isoxazole-5-carboxylic acid amide

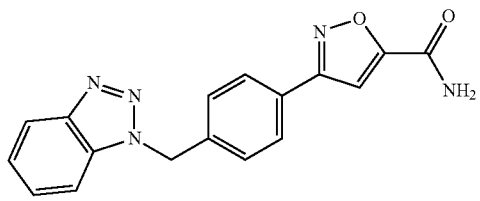 [SMILES: NC(=O)c1cc(-c2ccc(Cn3nnc4ccccc43)cc2)no1]

To a mixture of benzotriazole (13 mg, 0.11 mmol) in DMF (1 mL) was added NaH (60% dispersion; 5 mg, 0.125 mmol). The mixture was stirred for 20 min and then a solution of 3-(4-bromomethyl-phenyl)-isoxazole-5-carboxylic acid amide (which may be prepared as described in Preparation of Intermediate 14; 30 mg, 0.107 mmol) in DMF (1 mL) was added. The reaction mixture was stirred at room temperature overnight. $H_2O$ was added and the mixture was extracted with EtOAc (3×25 mL). The combined organic layers were washed three times with $H_2O$/brine, dried ($Na_2SO_4$), evaporated, and purified by chromatography (10-25% acetone/$CH_2Cl_2$) to give 3-(4-benzotriazol-1-ylmethyl-phenyl)-isoxazole-5-carboxylic acid amide (12 mg, 35%) as a white powder. $^1$H NMR (300 MHz, DMSO-$d_6$) δ ppm 8.36 (br. s., 1H) 8.06 (d, J=8.2 Hz, 1H) 7.98 (br. s., 1H) 7.81-7.91 (m, 3H) 7.49-7.59 (m, 2H) 7.34-7.48 (m, 3H) 6.06 (s, 2H).

Example 49

3-(4-Benzoimidazol-1-ylmethyl-phenyl)-isoxazole-5-carboxylic acid amide

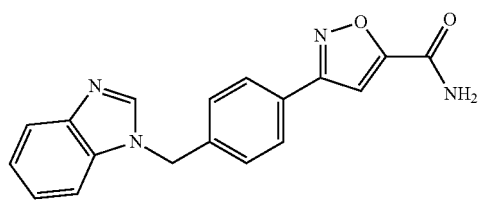 [SMILES: NC(=O)c1cc(-c2ccc(Cn3cnc4ccccc43)cc2)no1]

A mixture of benzimidazole (24 mg, 0.20 mmol), $K_2CO_3$ (0.2 mmol), and 3-(4-bromomethyl-phenyl)-isoxazole-5-carboxylic acid amide (which may be prepared as described in Preparation of Intermediate 14; 25 mg, 0.09 mmol) in $CH_3CN$ (1 mL) was heated overnight at 60° C. The mixture was filtered and the solvent was evaporated from the filtrate. The residue was purified by chromatography to give 3-(4-benzoimidazol-1-ylmethyl-phenyl)-isoxazole-5-carboxylic acid amide (13.6 mg, 48%). Based on the NMR, the purity was estimated as 80%.

Examples 50 and 51

3-(4-Indazol-1-ylmethyl-phenyl)-isoxazole-5-carboxylic acid amide and 3-(4-Indazol-2-ylmethyl-phenyl)-isoxazole-5-carboxylic acid amide

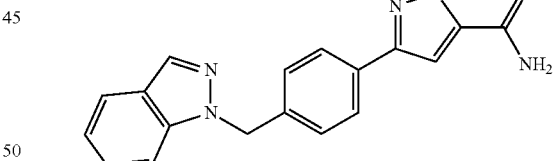

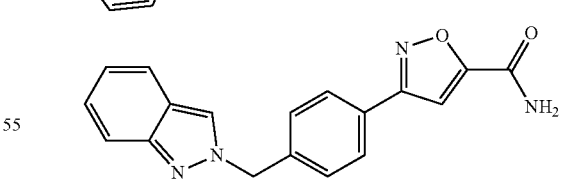

A mixture of indazole (24 mg, 0.20 mmol), $K_2CO_3$ (0.2 mmol), and 3-(4-bromomethyl-phenyl)-isoxazole-5-carboxylic acid amide (which may be prepared as described in Preparation of Intermediate 14; 25 mg, 0.09 mmol) in $CH_3CN$ (1 mL) was heated overnight at 60° C. The mixture was filtered and the solvent was evaporated from the filtrate. The residue was purified by chromatography to give two isomeric indazole products in yields of 4.6 mg (16%, higher Rf isomer) and 3.5 mg (12%, lower Rf isomer). It was not possible to assign the individual structures based on NMR.

Example 52

3-[4-(3,4-Dihydro-2H-quinolin-1-ylmethyl)-phenyl]-isoxazole-5-carboxylic acid amide

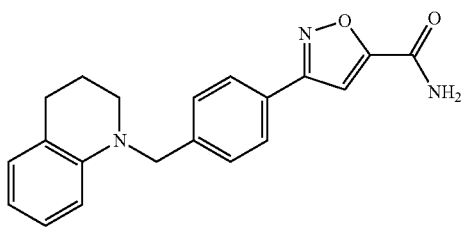 [SMILES: NC(=O)c1cc(-c2ccc(CN3CCCc4ccccc43)cc2)no1]

To a solution of tetrahydroquinoline (20 μL, 0.16 mmol) in dichloroethane (1 mL) was added Na(OAc)$_3$BH (88 mg, 0.415 mmol). The mixture was stirred at room temperature under argon for 20 min. A slurry of 3-(4-formyl-phenyl)-isoxazole-5-carboxylic acid amide (which may be prepared as described in Preparation of Intermediate 20; 20 mg, 0.093 mmol) in dichloroethane (1 mL) was added, followed by AcOH (20 μL). The reaction mixture was stirred at room temperature overnight. 1 M Na$_2$CO$_3$ solution was added and the mixture was extracted with CHCl$_3$ (3×25 mL). The combined organic layers were washed with brine, dried (Na$_2$SO$_4$), evaporated, and purified by chromatography (11-20% acetone/CH$_2$Cl$_2$) to give 3-[4-(3,4-dihydro-2H-quinolin-1-ylmethyl)-phenyl]-isoxazole-5-carboxylic acid amide (21 mg, 45%) as a white powder. $^1$H NMR (300 MHz, DMSO-d$_6$) δ ppm 8.35 (br. s., 1H), 7.97 (br. s., 1H), 7.84 (d, J=8.2 Hz, 2H), 7.47-7.57 (m, 1H), 7.38 (d, J=7.8 Hz, 2H), 6.72-6.93 (m, 2H), 6.36-6.50 (m, 2H), 4.53 (s, 2H), 3.34-3.43 (m, 2H), 2.73 (t, J=6.2 Hz, 2H), 1.93 (dt, J=11.2, 5.7 Hz, 2H).

Example 53

3-[4-(2-Methyl-2,3-dihydro-indol-1-ylmethyl)-phenyl]-isoxazole-5-carboxylic acid amide

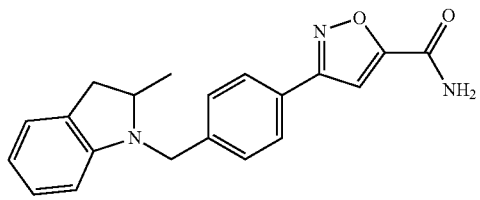 [SMILES: CC1Cc2ccccc2N1Cc1ccc(-c2cc(C(N)=O)on2)cc1]

To a solution of 2-methylindoline (21 μL, 0.16 mmol) in dichloroethane (1 mL) was added Na(OAc)$_3$BH (88 mg, 0.415 mmol). The mixture was stirred at room temperature under argon for 20 min. A slurry of 3-(4-formyl-phenyl)-isoxazole-5-carboxylic acid amide (which may be prepared as described in Preparation of Intermediate 20; 20 mg, 0.093 mmol) in dichloroethane (1 mL) was added, followed by AcOH (20 μL). The reaction mixture was stirred at room temperature overnight. 1 M Na$_2$CO$_3$ solution was added and the mixture was extracted with CHCl$_3$ (3×25 mL). The organic layer was washed with brine, dried (Na$_2$SO$_4$), evaporated, and purified by chromatography (11-20% acetone/CH$_2$Cl$_2$) to give 3-[4-(2-methyl-2,3-dihydro-indol-1-ylmethyl)-phenyl]-isoxazole-5-carboxylic acid amide (25 mg, 54%) as a white powder. $^1$H NMR (300 MHz, DMSO-d$_6$) δ ppm 8.36 (br. s., 1H), 7.98 (br. s., 1H), 7.85 (d, J=8.2 Hz, 2H), 7.56 (s, 1H), 7.48 (d, J=7.8 Hz, 2H), 6.99 (d, J=7.2 Hz, 1H), 6.84-6.94 (m, 1H), 6.53 (t, J=7.4 Hz, 1H), 6.31 (d, J=7.8 Hz, 1H), 4.45 (d, J=16.3 Hz, 1H), 4.14-4.27 (m, 1H), 3.57-3.76 (m, 1H), 3.12 (dd, J=15.8, 8.6 Hz, 1H), 2.56 (dd, J=16.0, 9.4 Hz, 1H), 1.25 (d, J=6.3 Hz, 3H).

Example 54

3-[4-(4-Methyl-indol-1-ylmethyl)-phenyl]-isoxazole-5-carboxylic acid amide

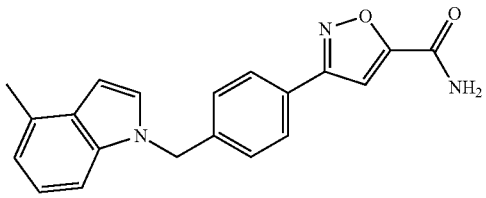 [SMILES: Cc1cccc2c1ccn2Cc1ccc(-c2cc(C(N)=O)on2)cc1]

To a mixture of 4-methylindole (20 mg, 0.15 mmol) in THF (1 mL) was added NaH (60% dispersion; 5 mg, 0.125 mmol). The mixture was stirred for 30 min and then a solution of 3-(4-bromomethyl-phenyl)-isoxazole-5-carboxylic acid amide (which may be prepared as described in Preparation of Intermediate 14; 35 mg, 0.125 mmol) in THF (1 mL) was added. The reaction mixture was stirred at room temperature overnight. The THF was evaporated and the residue was taken up in DMF (2 mL). The reaction mixture was stirred at room temperature for 8 days, then H$_2$O was added and the mixture was extracted with EtOAc (3×25 mL). The combined organic layers were washed three times with H$_2$O/brine, dried (Na$_2$SO$_4$), evaporated, and purified by chromatography (16-20% acetone/CH$_2$Cl$_2$) to give 3-[4-(4-methyl-indol-1-ylmethyl)-phenyl]-isoxazole-5-carboxylic acid amide (6 mg, 14%) as a white powder. $^1$H NMR (300 MHz, DMSO-d$_6$) δ ppm 8.35 (br. s., 1H), 7.97 (br. s., 1H), 7.81 (d, J=8.2 Hz, 2H), 7.43-7.56 (m, 2H), 7.17-7.34 (m, 3H), 6.91-7.03 (m, 1H), 6.80 (d, J=6.9 Hz, 1H), 6.51 (d, J=3.0 Hz, 1H), 5.47 (s, 2H), 2.45 (s, 2H).

Example 55

3-[3-Chloro-4-(2-trifluoromethyl-benzyloxy)-phenyl]-isoxazole-5-carboxylic acid amide

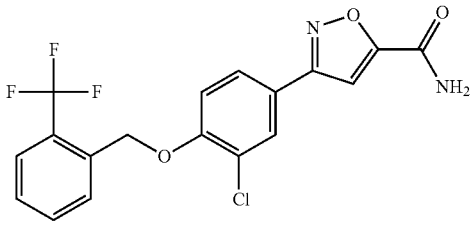 [SMILES: NC(=O)c1cc(-c2ccc(OCc3ccccc3C(F)(F)F)c(Cl)c2)no1]

N-Chlorosuccinimide (1.82 g, 13.7 mmol) was added in portions to a solution of 4-(2-trifluoromethyl-benzyloxy)- benzaldehyde oxime (which may be prepared as described in Preparation of Intermediate 21; 3.5 g, 11.9 mmol) in DMF (7 mL) at 0° C. The reaction mixture was allowed to warm to room temperature during the addition and then stirred for 2 h at room temperature. The mixture was poured into ice-water and extracted with EtOAc. The organic layer was dried (Na$_2$SO$_4$), filtered and evaporated. The residue was dissolved in 50% aqueous tert-butanol (90 mL). Ethyl propiolate (1.2 mL, 11.8 mmol) was added, followed by 1 M sodium ascorbate (1.23 mL, 1.23 mmol) and 0.1 M copper(II) sulfate (120 mL, 12 mmol). KHCO$_3$ (3.75 g, 37.5 mmol) was added and the reaction mixture was stirred at room temperature for 3 h. The solid was filtered off and dissolved in 2 M NH$_3$ in EtOH (15 mL). The resulting mixture was stirred at room temperature overnight. The solvent was evaporated and the residue was purified by chromatography (35-40% EtOAc/hexanes) to give 3-[3-chloro-4-(2-trifluoromethyl-benzyloxy)-phenyl]-isoxazole-5-carboxylic acid amide (158 mg, 6%) as a white solid. HRMS Calcd. for C$_{18}$H$_{13}$ClF$_3$N$_2$O$_3$ (M+H)$^+$, 397.0562. Found: 397.0558.

Example 56

Biological Assay of Compounds of the Invention In Vitro

Stearoyl CoA desaturase activity was monitored by a modification of the acyl carrier protein assay described by B. R. Talamo and K. Bloch in *Anal. Biochem.* 1968, 29, 300-304. The SCD assay monitors the release of tritiated water from the desaturation of 9,10-$^3$H-stearoyl CoA.

Mouse liver microsomes, prepared from mice fed a high-carbohydrate diet, were a source of the SCD and cyt b5 and cyt b5 reductase, necessary accessory proteins for the coupled reaction. Reaction mixtures for compound titrations contained 50 mM Tris HCl pH 7.5, 100 mM NaCl, 0.165 mg/ml BSA, 2.4% DMSO, 1 mM NADH, 0.03% T-20, and 300 nM (9,10)$^3$H-stearoyl CoA (Perkin-Elmer). Reactions were initiated upon the addition of 4 ug/ml SCD microsomes. Incubations were terminated after 25 minutes at room temperature with cold 6% TCA. After standing 10 minutes at 4° C., samples were centrifuged 15 minutes at 4000 rpm to pellet precipitated protein. Supernatants were added to microtiter plates containing suspensions of activated charcoal (Darco G-60, Fisher Scientific) and mixed by inversion. Plates were then centrifuged to separate $^3$H—H$_2$O product from charcoal-bound reactants. Supernatants were quantitated in a Perkin Elmer Topcount 384 after solubilization in ScintiSafe Plus 50% (Fisher Scientific).

Inhibition (%) of SCD activity by compounds was calculated according to the following formula:

% Inhibition=100*[1−(CPM$_{sample}$−CPM$_{blank}$)/(CPM$_{total}$−CPM$_{blank}$)]

The results of the in vitro inhibition of SCD1 by certain compounds of the present invention are shown in the following Table:

| Example | Name | IC50 (μM) |
|---|---|---|
| 1 | 3-[4-(2-Trifluoromethylsulfanyl-benzyloxy)-phenyl]-isoxazole-5-carboxylic acid amide | 0.48 |
| 2 | 3-[4-(2-Trifluoromethanesulfinyl-benzyloxy)-phenyl]-isoxazole-5-carboxylic acid amide | 0.58 |
| 3 | 3-[4-(2-Methoxy-benzyloxy)-phenyl]-isoxazole-5-carboxylic acid amide | 0.85 |
| 4 | 3-[4-(3,4-Dimethyl-benzyloxy)-phenyl]-isoxazole-5-carboxylic acid amide | 2.7 |
| 5 | 3-[4-(2-Cyano-benzyloxy)-phenyl]-isoxazole-5-carboxylic acid amide | 0.97 |
| 6 | 3-[4-(2,6-Dichloro-benzyloxy)-phenyl]-isoxazole-5-carboxylic acid amide | 2.6 |
| 7 | 3-[4-(3,4-Difluoro-benzyloxy)-phenyl]-isoxazole-5-carboxylic acid amide | 2.3 |
| 8 | 3-[4-(2-Fluoro-benzyloxy)-phenyl]-isoxazole-5-carboxylic acid amide | 0.56 |
| 9 | 3-[4-(2-Methyl-benzyloxy)-phenyl]-isoxazole-5-carboxylic acid amide | 0.46 |
| 10 | 3-[4-(2-Trifluoromethoxy-benzyloxy)-phenyl]-isoxazole-5-carboxylic acid amide | 0.21 |
| 11 | 3-[4-(2-Iodo-benzyloxy)-phenyl]-isoxazole-5-carboxylic acid amide | 0.41 |
| 12 | 3-[4-(2-Chloro-6-fluoro-benzyloxy)-phenyl]-isoxazole-5-carboxylic acid amide | 3.1 |
| 13 | 3-[4-(2-Chloro-5-fluoro-benzyloxy)-phenyl]-isoxazole-5-carboxylic acid amide | 0.42 |
| 14 | 3-[5-(2-Chloro-benzyloxy)-pyridin-2-yl]-isoxazole-5-carboxylic acid amide | 1.4 |
| 15 | 3-[4-(2-Chloro-pyridin-3-ylmethoxy)-phenyl]-isoxazole-5-carboxylic acid amide | 2.4 |
| 16 | 3-[4-(3-Fluoro-benzyloxy)-phenyl]-isoxazole-5-carboxylic acid amide | 0.45 |
| 17 | 3-[4-(3-Trifluoromethyl-benzyloxy)-phenyl]-isoxazole-5-carboxylic acid amide | 1.4 |
| 18 | 3-[4-(3-Chloro-benzyloxy)-phenyl]-isoxazole-5-carboxylic acid amide | 1.5 |
| 19 | 3-[4-(2-Chloro-benzyloxy)-phenyl]-isoxazole-5-carboxylic acid amide | 0.28 |
| 20 | 3-[4-(2-Bromo-benzyloxy)-phenyl]-isoxazole-5-carboxylic acid amide | 0.17 |
| 21 | 3-[4-(2-Trifluoromethyl-benzyloxy)-phenyl]-isoxazole-5-carboxylic acid amide | 0.18 |
| 22 | 3-[4-(2-Methanesulfonyl-benzyloxy)-phenyl]-isoxazole-5-carboxylic acid amide | 1.5 |
| 23 | 3-[4-(2-Chloro-phenoxymethyl)-phenyl]-isoxazole-5-carboxylic acid amide | 0.1 |
| 24 | 3-[4-(3-Chloro-phenoxymethyl)-phenyl]-isoxazole-5-carboxylic acid amide | 0.29 |
| 25 | 3-[4-(4-Chloro-phenoxymethyl)-phenyl]-isoxazole-5-carboxylic acid amide | 1.3 |
| 26 | 3-(4-o-Tolyloxymethyl-phenyl)-isoxazole-5-carboxylic acid amide | 0.066 |
| 27 | 3-(4-m-Tolyloxymethyl-phenyl)-isoxazole-5-carboxylic acid amide | 0.56 |
| 28 | 3-[4-(2-Methoxy-phenoxymethyl)-phenyl]-isoxazole-5-carboxylic acid amide | 0.17 |
| 29 | 3-[4-(3-Methoxy-phenoxymethyl)-phenyl]-isoxazole-5-carboxylic acid amide | 0.34 |
| 30 | 3-[4-(4-Methoxy-phenoxymethyl)-phenyl]-isoxazole-5-carboxylic acid amide | 3.3 |
| 31 | 3-[4-(2,6-Dimethyl-phenoxymethyl)-phenyl]-isoxazole-5-carboxylic acid amide | 1.9 |
| 32 | 3-[4-(2-Isopropyl-phenoxymethyl)-phenyl]-isoxazole-5-carboxylic acid amide | 0.38 |
| 33 | 3-[4-(2-Trifluoromethoxy-phenoxymethyl)-phenyl]-isoxazole-5-carboxylic acid amide | 0.47 |
| 34 | 3-[4-(2-Ethyl-phenoxymethyl)-phenyl]-isoxazole-5-carboxylic acid amide | 0.21 |
| 35 | 3-[4-(2-tert-Butyl-phenoxymethyl)-phenyl]-isoxazole-5-carboxylic acid amide | 0.65 |
| 36 | 3-[4-(2-Trifluoromethyl-phenoxymethyl)-phenyl]-isoxazole-5-carboxylic acid amide | 0.26 |
| 37 | 3-[4-(2-Cyano-phenoxymethyl)-phenyl]-isoxazole-5-carboxylic acid amide | 0.31 |
| 38 | 3-[4-(3-Methyl-pyridin-2-yloxymethyl)-phenyl]-isoxazole-5-carboxylic acid amide | 0.35 |
| 39 | 3-[4-(2-Fluoro-phenoxymethyl)-phenyl]-isoxazole-5-carboxylic acid amide | 0.51 |
| 40 | 3-[4-(5-Chloro-2-methyl-phenoxymethyl)-phenyl]-isoxazole-5-carboxylic acid amide | 0.14 |
| 41 | 3-[4-(3-Chloro-2-methyl-phenoxymethyl)-phenyl]-isoxazole-5-carboxylic acid amide | 0.39 |

-continued

| Example | Name | IC50 (μM) |
|---|---|---|
| 42 | 3-[4-(4-Fluoro-2-methyl-phenoxymethyl)-phenyl]-isoxazole-5-carboxylic acid amide | 0.28 |
| 43 | 3-[4-(5-Fluoro-2-methyl-phenoxymethyl)-phenyl]-isoxazole-5-carboxylic acid amide | 0.055 |
| 44 | 3-[4-(2-Methyl-pyridin-3-yloxymethyl)-phenyl]-isoxazole-5-carboxylic acid amide | 1.1 |
| 45 | 3-[4-(2,3-Dihydro-indol-1-ylmethyl)-phenyl]-isoxazole-5-carboxylic acid amide | 0.031 |
| 46 | 3-[4-(1,3-Dihydro-isoindol-2-ylmethyl)-phenyl]-isoxazole-5-carboxylic acid amide | 2.8 |
| 47 | 3-(4-Indol-1-ylmethyl-phenyl)-isoxazole-5-carboxylic acid amide | 0.017 |
| 48 | 3-(4-Benzotriazol-1-ylmethyl-phenyl)-isoxazole-5-carboxylic acid amide | 0.23 |
| 49 | 3-(4-Benzoimidazol-1-ylmethyl-phenyl)-isoxazole-5-carboxylic acid amide | 0.072 |
| 50 | 3-(4-Indazol-1-ylmethyl-phenyl)-isoxazole-5-carboxylic acid amide | 0.074 |
| 51 | 3-(4-Indazol-2-ylmethyl-phenyl)-isoxazole-5-carboxylic acid amide | 0.047 |
| 52 | 3-[4-(3,4-Dihydro-2H-quinolin-1-ylmethyl)-phenyl]-isoxazole-5-carboxylic acid amide | 0.024 |
| 53 | 3-[4-(2-Methyl-2,3-dihydro-indol-1-ylmethyl)-phenyl]-isoxazole-5-carboxylic acid amide | 0.1 |
| 54 | 3-[4-(4-Methyl-indol-1-ylmethyl)-phenyl]-isoxazole-5-carboxylic acid amide | 0.22 |
| 55 | 3-[3-Chloro-4-(2-trifluoromethyl-benzyloxy)-phenyl]-isoxazole-5-carboxylic acid amide | 2.7 |

Example A

Film coated tablets containing the following ingredients can be manufactured in a conventional manner:

| Ingredients | Per tablet | |
|---|---|---|
| Kernel: | | |
| Compound of formula (I) | 10.0 mg | 200.0 mg |
| Microcrystalline cellulose | 23.5 mg | 43.5 mg |
| Lactose hydrous | 60.0 mg | 70.0 mg |
| Povidone K30 | 12.5 mg | 15.0 mg |
| Sodium starch glycolate | 12.5 mg | 17.0 mg |
| Magnesium stearate | 1.5 mg | 4.5 mg |
| (Kernel Weight) | 120.0 mg | 350.0 mg |
| Film Coat: | | |
| Hydroxypropyl methyl cellulose | 3.5 mg | 7.0 mg |
| Polyethylene glycol 6000 | 0.8 mg | 1.6 mg |
| Talc | 1.3 mg | 2.6 mg |
| Iron oxide (yellow) | 0.8 mg | 1.6 mg |
| Titan dioxide | 0.8 mg | 1.6 mg |

The active ingredient is sieved and mixed with microcrystalline cellulose and the mixture is granulated with a solution of polyvinylpyrrolidone in water. The granulate is then mixed with sodium starch glycolate and magnesium stearate and compressed to yield kernels of 120 or 350 mg respectively. The kernels are lacquered with an aq. solution/suspension of the above mentioned film coat.

Example B

Capsules containing the following ingredients can be manufactured in a conventional manner:

| Ingredients | Per capsule |
|---|---|
| Compound of formula (I) | 25.0 mg |
| Lactose | 150.0 mg |
| Maize starch | 20.0 mg |
| Talc | 5.0 mg |

The components are sieved and mixed and filled into capsules of size 2.

Example C

Injection solutions can have the following composition:

| | |
|---|---|
| Compound of formula (I) | 3.0 mg |
| Polyethylene glycol 400 | 150.0 mg |
| Acetic acid | q.s. ad pH 5.0 |
| Water for injection solutions | ad 1.0 ml |

The active ingredient is dissolved in a mixture of Polyethylene glycol 400 and water for injection (part). The pH is adjusted to 5.0 by addition of acetic acid. The volume is adjusted to 1.0 ml by addition of the residual amount of water. The solution is filtered, filled into vials using an appropriate overage and sterilized.

The invention claimed is:

1. A compound of formula (I)

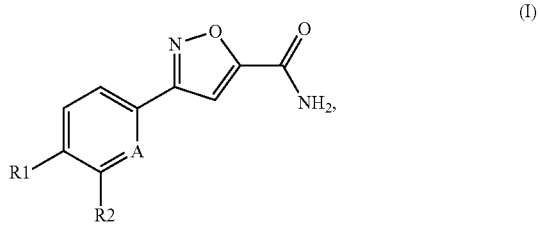

wherein:
A is —CH— or nitrogen;
R1 is —O—CH$_2$—R3, —CH$_2$—O—R3 or —CH$_2$—R4;
R2 is hydrogen or halogen;
R3 is -phenyl, optionally mono- or bi-substituted independently with lower alkyl, alkoxy, halogen, —CN, —CF$_3$, —OCF$_3$, —SCF$_3$, —S(=O)CF$_3$ or —SO$_2$CH$_3$, or -pyridinyl, optionally substituted with lower alkyl or halogen; and
R4 is indolyl, dihydroindolyl, isoindolyl, dihydroisoindolyl, benzotriazolyl, benzoimidazolyl, indazolyl, tetrahydroquinolinyl, methyldihydroindolyl or methylindolyl;
or a pharmaceutically acceptable salt thereof.

2. The compound according to claim 1, wherein A is —CH—.

3. The compound according to claim 1, wherein R1 is —O—CH$_2$—R3.

4. The compound according to claim 1, wherein R1 is —CH$_2$—O—R3.

5. The compound according to claim 1, wherein R1 is —CH$_2$—R4.

6. The compound according to claim 1, wherein R2 is hydrogen or chlorine.

7. The compound according to claim 1, wherein R3 is phenyl, mono- or bi-substituted independently with lower alkyl, alkoxy, halogen, —CN, —CF$_3$, —OCF$_3$, —SCF$_3$, —S(=O)CF$_3$, or —SO$_2$CH$_3$.

8. The compound according to claim 1, wherein R3 is pyridinyl substituted with lower alkyl or halogen.

9. The compound according to claim 1, wherein R4 is indolyl, dihydroindolyl, isoindolyl or dihydroisoindolyl.

10. The compound according to claim 1, wherein R4 is benzotriazolyl, benzoimidazolyl, indazolyl, tetrahydroquinolinyl, methyldihydroindolyl or methylindolyl.

11. The compound according to claim 1, wherein said compound is:
- 3-[4-(2-Trifluoromethylsulfanyl-benzyloxy)-phenyl]-isoxazole-5-carboxylic acid amide;
- 3-[4-(2-Trifluoromethanesulfinyl-benzyloxy)-phenyl]-isoxazole-5-carboxylic acid amide;
- 3-[4-(2-Methoxy-benzyloxy)-phenyl]-isoxazole-5-carboxylic acid amide;
- 3-[4-(3,4-Dimethyl-benzyloxy)-phenyl]-isoxazole-5-carboxylic acid amide;
- 3-[4-(2-Cyano-benzyloxy)-phenyl]-isoxazole-5-carboxylic acid amide;
- 3-[4-(2,6-Dichloro-benzyloxy)-phenyl]-isoxazole-5-carboxylic acid amide;
- 3-[4-(3,4-Difluoro-benzyloxy)-phenyl]-isoxazole-5-carboxylic acid amide;
- 3-[4-(2-Fluoro-benzyloxy)-phenyl]-isoxazole-5-carboxylic acid amide;
- 3-[4-(2-Methyl-benzyloxy)-phenyl]-isoxazole-5-carboxylic acid amide;
- 3-[4-(2-Trifluoromethoxy-benzyloxy)-phenyl]-isoxazole-5-carboxylic acid amide;
- 3-[4-(2-Iodo-benzyloxy)-phenyl]-isoxazole-5-carboxylic acid amide;
- 3-[4-(2-Chloro-6-fluoro-benzyloxy)-phenyl]-isoxazole-5-carboxylic acid amide;
- 3-[4-(2-Chloro-5-fluoro-benzyloxy)-phenyl]-isoxazole-5-carboxylic acid amide;
- 3-[5-(2-Chloro-benzyloxy)-pyridin-2-yl]-isoxazole-5-carboxylic acid amide;
- 3-[4-(2-Chloro-pyridin-3-ylmethoxy)-phenyl]-isoxazole-5-carboxylic acid amide;
- 3-[4-(3-Fluoro-benzyloxy)-phenyl]-isoxazole-5-carboxylic acid amide;
- 3-[4-(3-Trifluoromethyl-benzyloxy)-phenyl]-isoxazole-5-carboxylic acid amide;
- 3-[4-(3-Chloro-benzyloxy)-phenyl]-isoxazole-5-carboxylic acid amide;
- 3-[4-(2-Chloro-benzyloxy)-phenyl]-isoxazole-5-carboxylic acid amide;
- 3-[4-(2-Bromo-benzyloxy)-phenyl]-isoxazole-5-carboxylic acid amide;
- 3-[4-(2-Trifluoromethyl-benzyloxy)-phenyl]-isoxazole-5-carboxylic acid amide;
- 3-[4-(2-Methanesulfonyl-benzyloxy)-phenyl]-isoxazole-5-carboxylic acid amide;
- 3-[4-(2-Chloro-phenoxymethyl)-phenyl]-isoxazole-5-carboxylic acid amide;
- 3-[4-(3-Chloro-phenoxymethyl)-phenyl]-isoxazole-5-carboxylic acid amide;
- 3-[4-(4-Chloro-phenoxymethyl)-phenyl]-isoxazole-5-carboxylic acid amide;
- 3-(4-o-Tolyloxymethyl-phenyl)-isoxazole-5-carboxylic acid amide;
- 3-(4-m-Tolyloxymethyl-phenyl)-isoxazole-5-carboxylic acid amide;
- 3-[4-(2-Methoxy-phenoxymethyl)-phenyl]-isoxazole-5-carboxylic acid amide;
- 3-[4-(3-Methoxy-phenoxymethyl)-phenyl]-isoxazole-5-carboxylic acid amide;
- 3-[4-(4-Methoxy-phenoxymethyl)-phenyl]-isoxazole-5-carboxylic acid amide;
- 3-[4-(2,6-Dimethyl-phenoxymethyl)-phenyl]-isoxazole-5-carboxylic acid amide;
- 3-[4-(2-Isopropyl-phenoxymethyl)-phenyl]-isoxazole-5-carboxylic acid amide;
- 3-[4-(2-Trifluoromethoxy-phenoxymethyl)-phenyl]-isoxazole-5-carboxylic acid amide;
- 3-[4-(2-Ethyl-phenoxymethyl)-phenyl]-isoxazole-5-carboxylic acid amide;
- 3-[4-(2-tert-Butyl-phenoxymethyl)-phenyl]-isoxazole-5-carboxylic acid amide;
- 3-[4-(2-Trifluoromethyl-phenoxymethyl)-phenyl]-isoxazole-5-carboxylic acid amide;
- 3-[4-(2-Cyano-phenoxymethyl)-phenyl]-isoxazole-5-carboxylic acid amide;
- 3-[4-(3-Methyl-pyridin-2-yloxymethyl)-phenyl]-isoxazole-5-carboxylic acid amide;
- 3-[4-(2-Fluoro-phenoxymethyl)-phenyl]-isoxazole-5-carboxylic acid amide;
- 3-[4-(5-Chloro-2-methyl-phenoxymethyl)-phenyl]-isoxazole-5-carboxylic acid amide;
- 3-[4-(3-Chloro-2-methyl-phenoxymethyl)-phenyl]-isoxazole-5-carboxylic acid amide;
- 3-[4-(4-Fluoro-2-methyl-phenoxymethyl)-phenyl]-isoxazole-5-carboxylic acid amide;
- 3-[4-(5-Fluoro-2-methyl-phenoxymethyl)-phenyl]-isoxazole-5-carboxylic acid amide;
- 3-[4-(2-Methyl-pyridin-3-yloxymethyl)-phenyl]-isoxazole-5-carboxylic acid amide;
- 3-[4-(2,3-Dihydro-indol-1-ylmethyl)-phenyl]-isoxazole-5-carboxylic acid amide;
- 3-[4-(1,3-Dihydro-isoindol-2-ylmethyl)-phenyl]-isoxazole-5-carboxylic acid amide;
- 3-(4-Indol-1-ylmethyl-phenyl)-isoxazole-5-carboxylic acid amide;
- 3-(4-Benzotriazol-1-ylmethyl-phenyl)-isoxazole-5-carboxylic acid amide;
- 3-(4-Benzoimidazol-1-ylmethyl-phenyl)-isoxazole-5-carboxylic acid amide;
- 3-(4-Indazol-1-ylmethyl-phenyl)-isoxazole-5-carboxylic acid amide;
- 3-(4-Indazol-2-ylmethyl-phenyl)-isoxazole-5-carboxylic acid amide;
- 3-[4-(3,4-Dihydro-2H-quinolin-1-ylmethyl)-phenyl]-isoxazole-5-carboxylic acid amide;
- 3-[4-(2-Methyl-2,3-dihydro-indol-1-ylmethyl)-phenyl]-isoxazole-5-carboxylic acid amide;
- 3-[4-(4-Methyl-indol-1-ylmethyl)-phenyl]-isoxazole-5-carboxylic acid amide; or
- 3-[3-Chloro-4-(2-trifluoromethyl-benzyloxy)-phenyl]-isoxazole-5-carboxylic acid amide.

12. A pharmaceutical composition, comprising a therapeutically effective amount of a compound according to claim 1 and a pharmaceutically acceptable carrier.

13. A method for treating cancer, comprising the step of administering a therapeutically effective amount of a compound according to claim 1 to a subject in need thereof.

* * * * *

UNITED STATES PATENT AND TRADEMARK OFFICE
CERTIFICATE OF CORRECTION

| | |
|---|---|
| PATENT NO. | : 9,296,711 B2 |
| APPLICATION NO. | : 14/443823 |
| DATED | : March 29, 2016 |
| INVENTOR(S) | : Shawn David Erickson et al. |

Page 1 of 1

It is certified that error appears in the above-identified patent and that said Letters Patent is hereby corrected as shown below:

Title Page
    On Item 71, "Hoffman-La Roche Inc." should be replaced with "Hoffmann-La Roche Inc."
    On Item 73, "Hoffman-La Roche Inc." should be replaced with "Hoffmann-La Roche Inc."

Signed and Sealed this
Seventh Day of June, 2016

Michelle K. Lee
*Director of the United States Patent and Trademark Office*